(12) United States Patent
DeCorte et al.

(10) Patent No.: US 10,766,898 B2
(45) Date of Patent: *Sep. 8, 2020

(54) THERAPEUTIC COMPOUND FOR PAIN AND SYNTHESIS THEREOF

(71) Applicant: Janssen Pharmaceutica NV, Beerse (BE)

(72) Inventors: Bart DeCorte, Raritan, NJ (US); Jacob Cornelis Russcher, Nijmegen (NL); Menno Cornelis Franciscus Monnee, Nijmegen (NL)

(73) Assignee: Janssen Pharmaceutica NV, Beerse (BE)

(*) Notice: Subject to any disclaimer, the term of this patent is extended or adjusted under 35 U.S.C. 154(b) by 0 days.

This patent is subject to a terminal disclaimer.

(21) Appl. No.: 16/222,852

(22) Filed: Dec. 17, 2018

(65) Prior Publication Data

US 2019/0112311 A1  Apr. 18, 2019

Related U.S. Application Data

(62) Division of application No. 15/254,965, filed on Sep. 1, 2016, now Pat. No. 10,155,762.

(60) Provisional application No. 62/214,727, filed on Sep. 4, 2015, provisional application No. 62/214,734, filed on Sep. 4, 2015.

(51) Int. Cl.
| | |
|---|---|
| *C07D 471/18* | (2006.01) |
| *C07D 451/04* | (2006.01) |
| *C07D 451/06* | (2006.01) |
| *C07D 451/10* | (2006.01) |
| *C07D 451/12* | (2006.01) |
| *C07D 451/00* | (2006.01) |

(52) U.S. Cl.
CPC ......... *C07D 471/18* (2013.01); *C07D 451/00* (2013.01); *C07D 451/04* (2013.01); *C07D 451/06* (2013.01); *C07D 451/10* (2013.01); *C07D 451/12* (2013.01)

(58) Field of Classification Search
CPC ... C07D 471/18; C07D 451/00; C07D 451/04
USPC ....................................................... 514/292
See application file for complete search history.

(56) References Cited

U.S. PATENT DOCUMENTS

| | | | | |
|---|---|---|---|---|
| 9,994,572 B2* | 6/2018 | DeCorte | ............. | C07D 451/12 |
| 10,040,795 B2* | 8/2018 | DeCorte | ............. | C07D 451/00 |
| 10,040,796 B2* | 8/2018 | DeCorte | ............. | C07D 451/06 |
| 10,351,565 B2* | 7/2019 | DeCorte | ............. | C07D 451/00 |
| 10,351,566 B2* | 7/2019 | DeCorte | ............. | C07D 451/04 |
| 10,358,448 B2* | 7/2019 | DeCorte | ............. | C07D 451/10 |
| 2008/0188452 A1 | 8/2008 | Altenbach et al. | | |

FOREIGN PATENT DOCUMENTS

| | | |
|---|---|---|
| CN | 101768158 A | 7/2010 |
| CN | 102579458 A | 7/2012 |
| GB | 1469781 A | 4/1977 |
| WO | 9201688 A1 | 2/1992 |
| WO | 2007024814 A1 | 3/2007 |
| WO | 2008112734 A1 | 9/2008 |

OTHER PUBLICATIONS

International Search Report, dated Dec. 23, 2016 for PCT/US2016/049885 filed Sep. 1, 2016 (WO2017/040772, published Mar. 9, 2017).
International Search Report, dated Dec. 23, 2016 for PCT/US2016/049871 filed Sep. 1, 2016 (WO2017/040764, published Mar. 9, 2017).
International Search Report, dated Dec. 23, 2016 for PCT/US2016/049877 filed Sep. 1, 2016 (WO2017/040767, published Mar. 9, 2017).
International Search Report, dated Dec. 20, 2016 for PCT/US2016/049881 filed Sep. 1, 2016 (WO2017/040770, published Mar. 9, 2017).
Max Polonovski et al, "Psi-scopine et scopoline", Comptes Rendus Hebdomadaries Des Séances De L'Académie De Sciences, (19280101), pp. 147-149.
Extended European Search Report and European Search Opinion for European Patent Application No. 16842981.9, dated Feb. 25, 2019.

* cited by examiner

*Primary Examiner* — Rita J Desai

(57) ABSTRACT

The invention provides compounds of Formula XXIII:

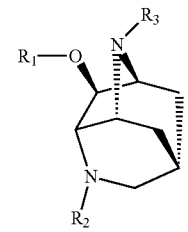

wherein $R_1$ is hydrogen, alkyl, acyl, or silyl, $R_2$ is hydrogen, alkyl, benzyl, acyl, or ester, and $R_3$ is hydrogen, alkyl, an aromatic group, azacyclic, carbocycle, aryl, cycloalkyl, heterocycloalkyl, heterocycle, heteroaryl, heteroalkyl, acyl, or ester, as well as derivatives and stereoisomers, pharmaceutically acceptable salts and derivatives thereof; and methods of making and using such compounds. The invention includes pharmaceutical compositions containing such compounds, and the use of such compounds in methods of treating conditions, diseases, or disorders.

28 Claims, 28 Drawing Sheets

THERAPEUTIC COMPOUND FOR PAIN AND SYNTHESIS THEREOF

RELATED APPLICATIONS

This patent application is a divisional of U.S. application Ser. No. 15/254,965, filed Sep. 1, 2016 (now U.S. Pat. No. 10,155,762, issued Dec. 18, 2018), which claims the benefit of U.S. Provisional Application Ser. No. 62/214,727, filed Sep. 4, 2015, and U.S. Provisional Application Ser. No. 62/214,734, filed Sep. 4, 2015, each of which is incorporated by reference herein in its entirety.

FIELD OF THE INVENTION

The invention provides new pharmaceutically active chemical compounds, which can be used for treating conditions and disorders in animals, mammals, and humans.

BACKGROUND

New chemical compounds having pharmaceutical activity can be indicated for the treatment of previously untreatable conditions, better treatment of conditions than can be achieved with conventional pharmaceutical compounds, and treatment of conditions that were previously treatable with conventional pharmaceutical compounds, but now are no longer effectively treatable.

SUMMARY OF THE INVENTION

The present invention provides compounds of Formula XXIII:

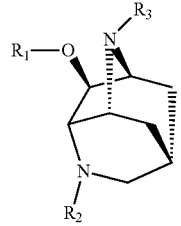

wherein $R_1$ is hydrogen, alkyl, acyl, or silyl, $R_2$ is hydrogen, alkyl, benzyl, acyl, or ester, and $R_3$ is hydrogen, alkyl, an aromatic group, azacyclic, carbocycle, aryl, cycloalkyl, heterocycloalkyl, heterocycle, heteroaryl, heteroalkyl, acyl, or ester, as well as derivatives and stereoisomers thereof.

In some embodiments, one or more of the $R_1$, $R_2$ and $R_3$ groups are optionally substituted with one or more substituents. In various embodiments, the optional substituents are selected from halo, $=O$, $=N-CN$, $=N-OR'$, $=NR'$, $OR'$, $N(R')_2$, $SR'$, $SO_2R'$, $SO_2NR'_2$, $NR'SO_2R'$, $NR'CONR'_2$, $NR'COOR'$, $NR'COR'$, $CN$, $COOR'$, $CON(R')_2$, $OOCR'$, $COR'$, and $NO_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and $=O$; wherein two R' can be linked to form a 3-7 membered ring optionally containing up to three heteroatoms selected from N, O and S.

In specific embodiments, $R_3$ is an optionally substituted aryl methyl group or an optionally substituted heteroaryl methyl group.

In certain embodiments, the invention includes a pharmaceutical composition containing a compound of Formula XXIII and/or a derivative thereof. In one embodiment, the invention includes a pharmaceutical composition comprising a compound of Formula XXIII and/or a derivative along with a pharmaceutically acceptable carrier or diluent. In another embodiment, the invention provides a method for treating a subject (a human or an animal) suffering from a condition, disease, or disorder, comprising administering to the subject an effective amount of a compound of Formula XXIII or a derivative thereof. In one embodiment, the compound is administered to effect localized delivery to the subject. In another embodiment, the compound is administered to effect systemic delivery to the subject. In a further embodiment, a compound of Formula XXIII, or a derivative thereof, is used as a medicament, or used in the manufacture of a medicament. In some embodiments, the condition or disorder is pain. In specific embodiments, the pain is neuropathic pain or chronic pain.

In certain embodiments, $R_3$ is trifluoroacyl.

In certain embodiments $R_1$ is tert-butyldiphenylsylyl, $R_2$ is hydrogen, and $R_3$ is $-COOR_4$, where $R_4$ is selected from the group consisting of alkyl and benzyl. In further embodiments, $R_4$ is benzyl, in other embodiments, $R_4$ is alkyl having 1 to 8 carbon atoms. In still further embodiments, $R_4$ is ethyl. In other embodiments, $R_4$ is tert-butyl.

The present invention provides compounds of Formula XXIII(A):

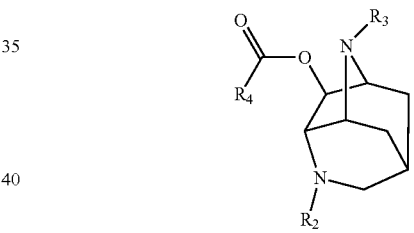

wherein $R_4$ is hydrogen, alkyl, an aromatic group, azacyclic, carbocycle, aryl, cycloalkyl, heterocycloalkyl, heterocycle, heteroaryl, heteroalkyl, acyl, or ester; $R_2$ is hydrogen, alkyl, benzyl, acyl, or ester, and $R_3$ is hydrogen, alkyl, an aromatic group, azacyclic, carbocycle, aryl, cycloalkyl, heterocycloalkyl, heterocycle, heteroaryl, heteroalkyl, acyl, or ester, as well as derivatives and stereoisomers thereof.

In some embodiments, $R_4$ is optionally substituted with one or more substituents selected from halo, $=O$, $=N-CN$, $=N-OR'$, $=NR'$, $OR'$, $N(R')_2$, $SR'$, $SO_2R'$, $SO_2NR'_2$, $NR'SO_2R'$, $NR'CONR'_2$, $NR'COOR'$, $NR'COR'$, $CN$, $COOR'$, $CON(R')_2$, $OOCR'$, $COR'$, and $NO_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and $=O$; wherein two R' can be linked to form a 3-7 membered ring optionally containing up to three heteroatoms selected from N, O and S.

In some embodiments, $R_2$ is optionally substituted with one or more substituents selected from halo, $=O$, $=N-CN$, $=N-OR'$, $=NR'$, $OR'$, $N(R')_2$, $SR'$, $SO_2R'$, SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, C$_1$-C$_6$ alkyl, C$_2$-C$_6$ heteroalkyl, C$_1$-C$_6$ acyl, C$_2$-C$_6$ heteroacyl, C$_6$-C$_{10}$ aryl, C$_5$-C$_{10}$ heteroaryl, C$_7$-C$_{12}$ arylalkyl, or C$_6$-C$_{12}$ heteroarylalkyl, each of which is optionally substituted with one or more groups selected from halo, C$_1$-C$_4$ alkyl, C$_1$-C$_4$ heteroalkyl, C$_1$-C$_6$ acyl, C$_1$-C$_6$ heteroacyl, hydroxy, amino, and =O; wherein two R' can be linked to form a 3-7 membered ring optionally containing up to three heteroatoms selected from N, O and S.

In some embodiments, R$_3$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, C$_1$-C$_6$ alkyl, C$_2$-C$_6$ heteroalkyl, C$_1$-C$_6$ acyl, C$_2$-C$_6$ heteroacyl, C$_6$-C$_{10}$ aryl, C$_5$-C$_{10}$ heteroaryl, C$_7$-C$_{12}$ arylalkyl, or C$_6$-C$_{12}$ heteroarylalkyl, each of which is optionally substituted with one or more groups selected from halo, C$_1$-C$_4$ alkyl, C$_1$-C$_4$ heteroalkyl, C$_1$-C$_6$ acyl, C$_1$-C$_6$ heteroacyl, hydroxy, amino, and =O; wherein two R' can be linked to form a 3-7 membered ring optionally containing up to three heteroatoms selected from N, O and S.

The present invention provides compounds of Formula XXIII(B):

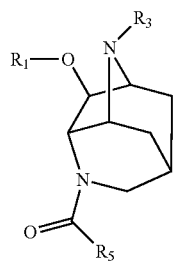

wherein R$_5$ is hydrogen, alkyl, an aromatic group, azacyclic, carbocycle, aryl, cycloalkyl, heterocycloalkyl, heterocycle, heteroaryl, heteroalkyl, acyl, or ester; R$_1$ is hydrogen, alkyl, benzyl, acyl, or ester, and R$_3$ is hydrogen, alkyl, an aromatic group, azacyclic, carbocycle, aryl, cycloalkyl, heterocycloalkyl, heterocycle, heteroaryl, heteroalkyl, acyl, or ester, as well as derivatives and stereoisomers thereof.

In some embodiments, R$_5$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, C$_1$-C$_6$ alkyl, C$_2$-C$_6$ heteroalkyl, C$_1$-C$_6$ acyl, C$_2$-C$_6$ heteroacyl, C$_6$-C$_{10}$ aryl, C$_5$-C$_{10}$ heteroaryl, C$_7$-C$_{12}$ arylalkyl, or C$_6$-C$_{12}$ heteroarylalkyl, each of which is optionally substituted with one or more groups selected from halo, C$_1$-C$_4$ alkyl, C$_1$-C$_4$ heteroalkyl, C$_1$-C$_6$ acyl, C$_1$-C$_6$ heteroacyl, hydroxy, amino, and =O; wherein two R' can be linked to form a 3-7 membered ring optionally containing up to three heteroatoms selected from N, O and S.

In some embodiments, R$_1$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, C$_1$-C$_6$ alkyl, C$_2$-C$_6$ heteroalkyl, C$_1$-C$_6$ acyl, C$_2$-C$_6$ heteroacyl, C$_6$-C$_{10}$ aryl, C$_5$-C$_{10}$ heteroaryl, C$_7$-C$_{12}$ arylalkyl, or C$_6$-C$_{12}$ heteroarylalkyl, each of which is optionally substituted with one or more groups selected from halo, C$_1$-C$_4$ alkyl, C$_1$-C$_4$ heteroalkyl, C$_1$-C$_6$ acyl, C$_1$-C$_6$ heteroacyl, hydroxy, amino, and =O; wherein two R' can be linked to form a 3-7 membered ring optionally containing up to three heteroatoms selected from N, O and S.

In some embodiments, R$_3$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, C$_1$-C$_6$ alkyl, C$_2$-C$_6$ heteroalkyl, C$_1$-C$_6$ acyl, C$_2$-C$_6$ heteroacyl, C$_6$-C$_{10}$ aryl, C$_5$-C$_{10}$ heteroaryl, C$_7$-C$_{12}$ arylalkyl, or C$_6$-C$_{12}$ heteroarylalkyl, each of which is optionally substituted with one or more groups selected from halo, C$_1$-C$_4$ alkyl, C$_1$-C$_4$ heteroalkyl, C$_1$-C$_6$ acyl, C$_1$-C$_6$ heteroacyl, hydroxy, amino, and =O; wherein two R' can be linked to form a 3-7 membered ring optionally containing up to three heteroatoms selected from N, O and S.

The present invention provides compounds of Formula XXIII(C):

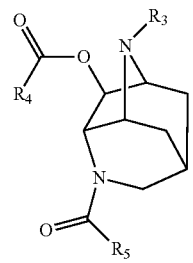

wherein R$_4$ is hydrogen, alkyl, an aromatic group, azacyclic, carbocycle, aryl, cycloalkyl, heterocycloalkyl, heterocycle, heteroaryl, heteroalkyl, acyl, or ester; R$_5$ is hydrogen, alkyl, benzyl, acyl, or ester, and R$_3$ is hydrogen, alkyl, an aromatic group, azacyclic, carbocycle, aryl, cycloalkyl, heterocycloalkyl, heterocycle, heteroaryl, heteroalkyl, acyl, or ester, as well as derivatives and stereoisomers thereof.

In some embodiments, R$_4$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, C$_1$-C$_6$ alkyl, C$_2$-C$_6$ heteroalkyl, C$_1$-C$_6$ acyl, C$_2$-C$_6$ heteroacyl, C$_6$-C$_{10}$ aryl, C$_5$-C$_{10}$ heteroaryl, C$_7$-C$_{12}$ arylalkyl, or C$_6$-C$_{12}$ heteroarylalkyl, each of which is optionally substituted with one or more groups selected from halo, C$_1$-C$_4$ alkyl, C$_1$-C$_4$ heteroalkyl, C$_1$-C$_6$ acyl, C$_1$-C$_6$ heteroacyl, hydroxy, amino, and =O; wherein two R' can be linked to form a 3-7 membered ring optionally containing up to three heteroatoms selected from N, O and S.

In some embodiments, R$_5$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, C$_1$-C$_6$ alkyl, C$_2$-C$_6$ heteroalkyl, C$_1$-C$_6$ acyl, C$_2$-C$_6$ heteroacyl, C$_6$-C$_{10}$ aryl, C$_5$-C$_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, $R_3$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

The present invention provides compounds of Formula XXIII(D):

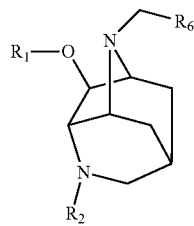

wherein $R_1$ is hydrogen, alkyl, an aromatic group, azacyclic, carbocycle, aryl, cycloalkyl, heterocycloalkyl, heterocycle, heteroaryl, heteroalkyl, acyl, or ester; $R_2$ is hydrogen, alkyl, benzyl, acyl, or ester, and $R_6$ is hydrogen, alkyl, an aromatic group, azacyclic, carbocycle, aryl, cycloalkyl, heterocycloalkyl, heterocycle, heteroaryl, heteroalkyl, acyl, or ester, as well as derivatives and stereoisomers thereof.

In some embodiments, $R_4$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, $R_5$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, $R_6$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

The present invention provides compounds of Formula XXIII(E):

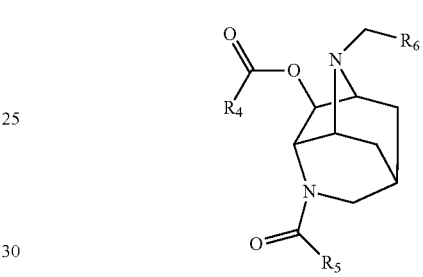

wherein $R_4$ is hydrogen, alkyl, an aromatic group, azacyclic, carbocycle, aryl, cycloalkyl, heterocycloalkyl, heterocycle, heteroaryl, heteroalkyl, acyl, or ester; $R_5$ is hydrogen, alkyl, benzyl, acyl, or ester, and $R_6$ is hydrogen, alkyl, an aromatic group, azacyclic, carbocycle, aryl, cycloalkyl, heterocycloalkyl, heterocycle, heteroaryl, heteroalkyl, acyl, or ester, as well as derivatives and stereoisomers thereof.

In some embodiments, $R_4$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, $R_5$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, $R_6$ is optionally substituted with one or more substituents selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

The present invention provides compounds of the Formula I:

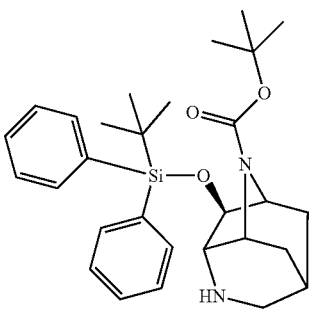 [SMILES: CC(C)(C)OC(=O)N1C2CC3CNC2[C@@H](O[Si](c2ccccc2)(c2ccccc2)C(C)(C)C)C1C3]

(2R,3S,6S,7aS)-tert-butyl 3-((tert-butyldiphenylsilyl)oxy) octahydro-1H-2,6-methanopyrrolo [3,2-b]pyridine-1-carboxylate and stereoisomers thereof. That is, a compound of Formula I can have the Formula I.a:

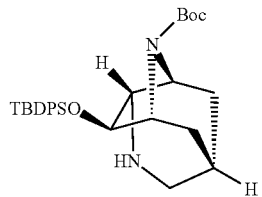

((2R*,3R*,3aS*,6S*,7aS*)-)-tert-butyl 3-((tert butyldiphenylsilyl)oxy)-octahydro-1H-2,6-methanopyrrolo[3,2-b] pyridine-1-carboxylate) or the Formula I.b:

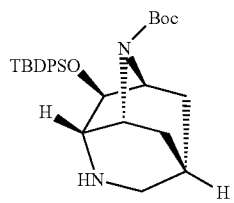

((2S*,3R*,3aS*,6R*,7aR*)-tert-butyl 3-((tertbutyldiphenylsilyl)oxy)octahydro-1H-2,6-methanopyrrolo[3,2-b]pyridine-1-carboxylate) where Boc is tert-butyloxycarbonyl and TBDPS is tert-butyldiphenylsilane.

A quantity of a compound of Formula I can be enantiomerically pure and consist entirely of the enantiomers of Formula I.a or the enantiomer of Formula I.b. Alternatively, it can comprise a mixture of the enantiomers, which may contain equal amounts of the enantiomer of Formula I.a and the enantiomer of Formula I.b, or be a mixture having differing amounts of each of the enantiomer of Formula I.a or the enantiomer of Formula I.b.

In certain embodiments, the invention includes a pharmaceutical composition containing a compound of Formula I and/or a derivative thereof. In one embodiment, the invention includes a pharmaceutical composition comprising a compound of Formula I and/or derivative thereof and a pharmaceutically acceptable carrier or diluent. In another embodiment, the invention provides a method for treating a subject (a human or an animal) suffering from a condition, disease, or disorder, comprising administering to the subject an effective amount of a compound of Formula I and/or derivative thereof. In one embodiment, the compound is administered to effect localized delivery to the subject. In another embodiment, the compound is administered to effect systemic delivery to the subject. In a further embodiment, a compound of Formula I, and/or derivative thereof is used as a medicament, or used in the manufacture of a medicament. In some embodiments, the condition or disorder is pain. In specific embodiments, the pain is neuropathic pain or chronic pain.

The present invention also provides methods of making a compound of Formula I.a or Formula I.b by chirally separating a racemic mixture of compounds of Formula I.

In other embodiments, the method includes making the compound of Formula I. In one such embodiment, the method of making the compound of Formula I includes reacting a compound of Formula II:

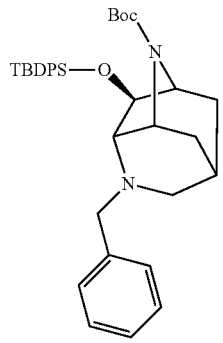

rac-(2R,3R,6S,7aS)-tert-butyl 4-benzyl-3-((tert-butyldiphenylsilyl)oxy)octahydro-1H-2,6-methanopyrrolo[3,2-b]pyridine-1-carboxylate with hydrogen. The reaction may be performed in the presence of a catalyst. In a preferred embodiment, the catalyst includes palladium. For example, the catalyst can be palladium on carbon.

In other embodiments, the method includes making the compound of Formula II. In one such embodiment, the method of making the compound of Formula II includes reacting a compound of Formula III:

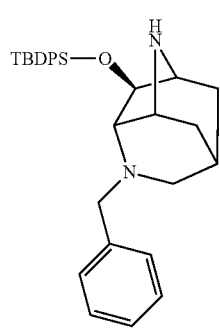

rac-(2R,3R,6S,7aS)-4-benzyl-3-((tert-butyldiphenylsilyl) oxy)octahydro-1H-2,6-methanopyrrolo[3,2-b]pyridine with di-tert-butyl dicarbonate (Boc$_2$O) to add a tert-butyloxycarbonyl (Boc) protecting group. In a preferred embodiment the reaction further comprises triethylamine (Et$_3$N).

In other embodiments, the method also includes making the compound of Formula III. In one such embodiment, the method of making the compound of Formula III includes reacting a compound of Formula IV:

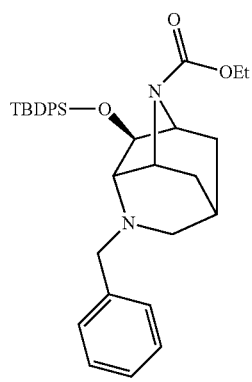

(2R,3R,6S,7aS)-ethyl 4-benzyl-3-((tert-butyldiphenylsilyl) oxy)octahydro-1H-2,6-methanopyrrolo[3,2-b]pyridine-1-carboxylate with iodotrimethylsilane.

In other embodiments, the method also includes making the compound of Formula IV. In one such embodiment, the method of making the compound of Formula IV includes reacting a compound of Formula V:

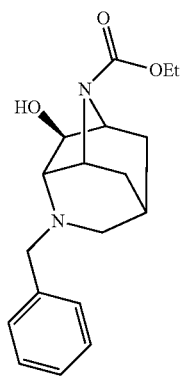 [SMILES: CCOC(=O)N1C2CC3CC1[C@H](O)C2N(Cc1ccccc1)C3]

(2R,3S,6S,7aS)-ethyl-4-benzyl-3-hydroxyoctahydro-1H-2,6-methanopyrrolo[3,2-b]pyridine-1-carboxylate with TBDPS. In a preferred embodiment the reaction further comprises imidazole.

In other embodiments, the method also includes making the compound of Formula V. In one such embodiment, the method of making the compound of Formula V includes reacting a compound of Formula VI:

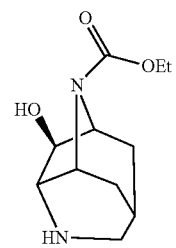

(2R,3S,6S,7aS)-ethyl 3-hydroxyoctahydro-1H-2,6-methanopyrrolo[3,2-b]pyridine-1-carboxylate with benzaldehyde. In a preferred embodiment the reaction further comprises sodium triacetoxyborohydride (STAB).

In other embodiments, the method also includes making the compound of Formula VI. In one such embodiment, the method of making the compound of Formula VI includes cyclizing a compound of Formula VI.a:

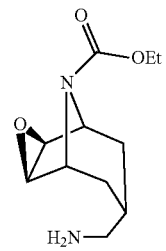 [SMILES: CCOC(=O)N1C2CC(CN)CC1[C@@H]1O[C@H]21]

(1R,2R,4S,5S,7s)-ethyl 7-(aminomethyl)-3-oxa-9-azatricyclo[3.3.1.0$^{2,4}$]nonane-9-carboxylate in a solvent. The solvent can be ethanol (EtOH).

In other embodiments, the method also includes making the compound of Formula VI.a. In one such embodiment, the method of making the compound of Formula VI.a includes reacting a compound of Formula VII:

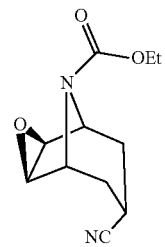 [SMILES: CCOC(=O)N1C2CC(C#N)CC1[C@@H]1O[C@H]21]

(1R,2R,4S,5S,7s)-ethyl 7-cyano-3-oxa-9-azatricyclo[3.3.1.0$^{2,4}$]nonane-9-carboxylate with hydrogen. The reaction may be performed in the presence of a catalyst. In one embodiment, the catalyst includes nickel. For example, the catalyst can be Raney-nickel.

In other embodiments, the method also includes making the compound of Formula VII. In one such embodiment, the method of making the compound of Formula VII includes reacting a compound of Formula VIII:

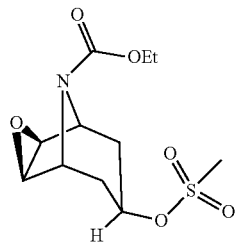 [SMILES: CCOC(=O)N1C2CC(OS(C)(=O)=O)CC1[C@@H]1O[C@H]21]

(1R,2R,4S,5S,7r)-ethyl 7-((methylsulfonyl)oxy)-3-oxa-9-azatricyclo[3.3.1.0²,⁴]nonane-9-carboxylate with potassium cyanide. In other embodiments the reaction further comprises 18-crown-6 (1,4,7,10,13,16-hexaoxacyclooctadecane).

In other embodiments, the method also includes making the compound of Formula VIII. In one such embodiment, the method of making the compound of Formula VIII includes reacting a compound of Formula IX:

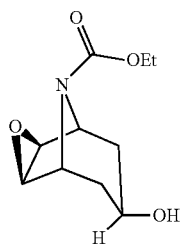 [SMILES: CCOC(=O)N1C2CC(O)CC1[C@@H]1O[C@H]21]

(1R,2R,4S,5S,7r)-ethyl 7-hydroxy-3-oxa-9-azatricyclo[3.3.1.0²,⁴]nonane-9-carboxylate with mesyl chloride. In a preferred embodiment the reaction further comprises triethylamine ($ET_3N$).

In other embodiments, the method also includes making the compound of Formula IX. In one such embodiment, the method of making the compound of Formula IX includes reacting a compound of Formula X:

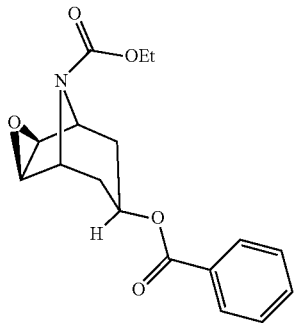 [SMILES: CCOC(=O)N1C2CC(OC(=O)c3ccccc3)CC1[C@@H]1O[C@H]21]

(1R,2R,4S,5S,7r)-ethyl 7-(benzoyloxy)-3-oxa-9-azatricyclo[3.3.1.0²,⁴]nonane-9-carboxylate with a reducing agent. The reducing agent can be sodium borohydride.

In other embodiments, the method also includes making the compound of Formula X. In one such embodiment, the method of making the compound of Formula X includes reacting a compound of Formula XI:

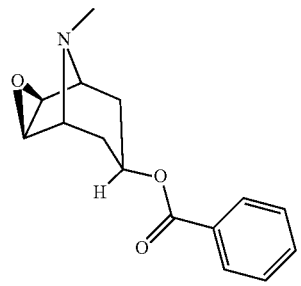 [SMILES: CN1C2CC(OC(=O)c3ccccc3)CC1[C@@H]1O[C@H]21]

(1R,2R,4S,5S,7r)-9-methyl-3-oxa-9-azatricyclo[3.3.1.0²,⁴]nonan-7-yl benzoate with ethyl chloroformate. In a preferred embodiment the reaction further comprises a base. The base can be potassium carbonate.

In other embodiments, the method also includes making the compound of Formula XI. In one such embodiment, the method of making the compound of Formula XI includes reacting a compound of Formula XII:

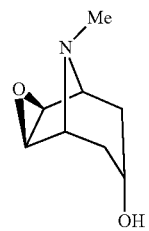 [SMILES: CN1C2CC(O)CC1[C@@H]1O[C@H]21]

(1R,2R,4S,5S)-9-methyl-3-oxa-9-azatricyclo[3.3.1.0²,⁴]nonan-7-ol) with benzoic acid in the presence of an activating agent. The activating agent can be diethylazodicaroxylate (DEAD) with triphenylphosphine ($PPh_3$) or diisopropyl azodicarboxylate (DIAD) with $PPh_3$.

In other embodiments, the method also includes making the compound of Formula XII. In one such embodiment, the method of making the compound of Formula XII includes reacting a compound of Formula XIII:

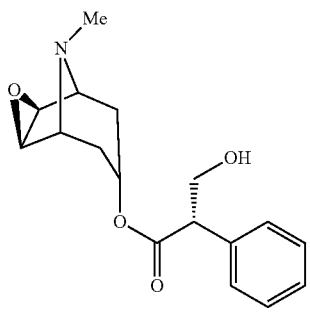 [SMILES: CN1C2CC(OC(=O)[C@H](CO)c3ccccc3)CC1[C@@H]1O[C@H]21]

(2S)-(1R,2R,4S,5S)-9-methyl-3-oxa-9-azatricyclo[3.3.1.02,4]nonan-7-yl-3-hydroxy-2-phenylpropanoate hydrobromide trihydrate (scopolamine) with a reducing agent. The reducing agent can be sodium borohydride. In a preferred embodiment the reaction further comprises HCl in isopropyl alcohol.

In a further embodiment the invention provides a compound of Formula XVIII:

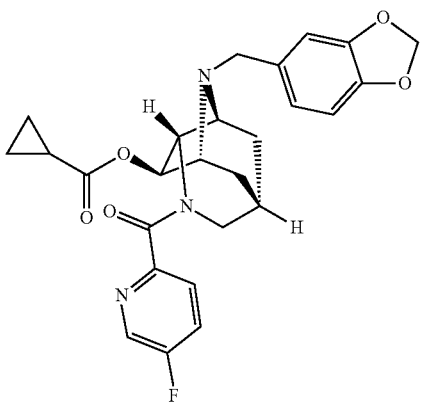 [SMILES: O=C(O[C@H]1[C@@H]2[C@@H]3C[C@@H](C[C@H]1N3Cc1ccc3c(c1)OCO3)CN2C(=O)c1ccc(F)cn1)C1CC1]

((2R*,3R*,3aS*,6S*,7aS*)-1-(benzo[d][1,3]dioxol-5-ylmethyl)-4-(5-fluoropicolinoyl)octahydro-1H-2,6-methanopyrrolo[3,2-b]pyridin-3-yl cyclopropanecarboxylate).

In certain embodiments, the invention includes a pharmaceutical composition containing a compound of Formula XVIII and/or a derivative thereof. In one embodiment, the invention includes a pharmaceutical composition comprising a compound of Formula XVIII and a pharmaceutically acceptable carrier or diluent. In another embodiment, the invention provides a method for treating a subject (a human or an animal) suffering from a condition, disease, or disorder, comprising administering to the subject an effective amount of a compound of Formula XVIII. In one embodiment, the compound is administered to effect localized delivery to the subject. In another embodiment, the compound is administered to effect systemic delivery to the subject. In a further embodiment, a compound of Formula XVIII is used as a medicament, or used in the manufacture of a medicament. In some embodiments, the condition or disorder is pain, including but not limited to neuropathic pain and chronic pain.

An embodiment of the invention provides a method of making a compound of Formula XVIII including reacting a compound of Formula XVII:

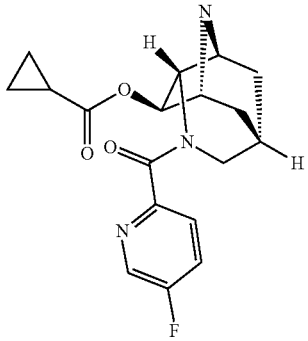 [SMILES: O=C(O[C@H]1[C@@H]2[C@@H]3C[C@@H](C[C@H]1N3)CN2C(=O)c1ccc(F)cn1)C1CC1]

((2R*,3R*,3aS*,6S*,7aS*)-1-(benzo[d][1,3]dioxol-5-ylmethyl)-4-(5-fluoropicolinoyl)octahydro-1H-2,6-methanopyrrolo[3,2-b]pyridin-3-yl cyclopropanecarboxylate) with piperonal. The reaction can be performed in the presence of a reducing agent. For example, the reducing agent can be STAB.

The method can also include making the compound of Formula XVII. In an embodiment, the method of making the compound of Formula XVII includes removing and replacing the Boc group from a compound of Formula XVI, with hydrogen:

Formula XVI

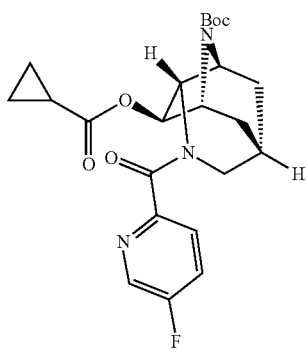

((2R*,3R*,3aS*,6S*,7aS*)-4-(5-fluoropicolinoyl)octahydro-1H-2,6-methanopyrrolo[3,2-b]pyridin-3-yl cyclopropanecarboxylate). The Boc group can be removed with an acid. For example, the acid can be trifluoracetic acid (TFA).

The method can also include making the compound of Formula XVI. In an embodiment, the method of making the compound of Formula XVI includes reacting a compound of Formula XV:

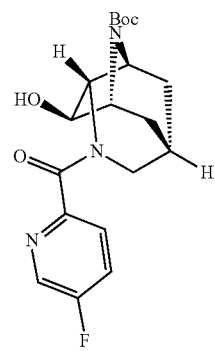 [SMILES: CC(C)(C)OC(=O)N1[C@@H]2C[C@@H]3C[C@H]1[C@@H]([C@@H]2O)N(C(=O)c1ccc(F)cn1)C3]

((2R*,3R*,3aS*,6S*,7aS*)-tert-butyl 4-(5-fluoropicolinoyl)-3-hydroxyoctahydro-1H-2,6-methanopyrrolo[3,2-b]pyridine-1-carboxylate) with cyclopropanecarbonyl chloride. The reaction can be performed in the presence of a nucleophilic catalyst. For example, the nucleophilic catalyst can be 4-dimethyl aminopyridine (DMAP).

The method can also include making the compound of Formula XV. In an embodiment, the method of making the compound of Formula XV includes removing the TBDPS group from a compound of Formula XIV, and replacing it with a hydrogen:

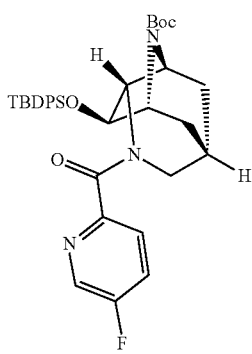

((2R*,3R*,3aS*,6S*,7aS*)-tert-butyl 3-((tert-butyldiphenylsilyl)oxy)-4-(5-fluoropicolinoyl)octahydro-1H-2,6-methanopyrrolo[3,2-b]pyridine-1-carboxylate). For example, the TBPDS group can be removed with tetrabutylammonium fluoride (TBAF).

The method can also include making the compound of Formula XIV. In an embodiment, the method of making the compound of Formula XIV includes reacting a compound of Formula I.a, with 5-fluoropicolinic acid. In a preferred embodiment the reaction further comprises 1-[Bis (dimethylamino)methylene]-1H-1,2,3-triazolo[4,5-b]pyridinium 3-oxid hexafluorophosphate (HATU) and N,N-diisopropylethylamine (DIPEA).

In a further embodiment the invention provides a compound of Formula XXII:

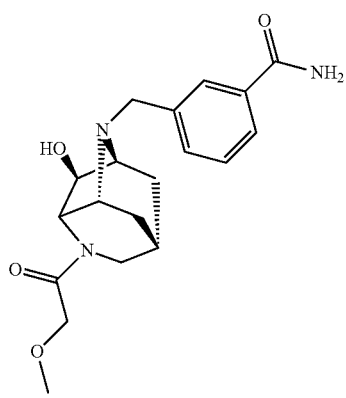 [SMILES: COCC(=O)N1C[C@@H]2C[C@@H]3C1[C@@H](O)[C@H](C2)N3Cc1cccc(C(N)=O)c1]

3-(((2S*,3S*,6R*,7aR*)-3-hydroxy-4-(2-methoxyacetyl) octahydro-1H-2,6-methanopyrrolo[3,2-b]pyridin-1-yl) methyl)benzamide.

In certain embodiments, the invention includes a pharmaceutical composition containing a compound of Formula XXII and/or a derivative thereof. In one embodiment, the invention includes a pharmaceutical composition comprising a compound of Formula XXII and a pharmaceutically acceptable carrier or diluent. In another embodiment, the invention provides a method for treating a subject (a human or an animal) suffering from a condition, disease, or disorder, comprising administering to the subject an effective amount of a compound of Formula XXII. In one embodiment, the compound is administered to effect localized delivery to the subject. In another embodiment, the compound is administered to effect systemic delivery to the subject. In a further embodiment, a compound of Formula XXII is used as a medicament, or used in the manufacture of a medicament. In some embodiments, the condition or disorder is pain. In specific embodiments, the pain is neuropathic pain or chronic pain.

An embodiment of the invention provides a method of making a compound of Formula XXII including reacting a compound of Formula XXI:

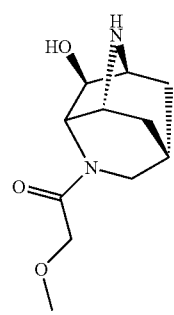 [SMILES: COCC(=O)N1C[C@H]2C[C@@H]3N[C@H](C2)C1[C@H]3O]

1-((2S*,3S*,3aS*,6R*,7aR*)-3-hydroxyhexahydro-1H-2,6-methanopyrrolo[3,2-b]pyridin-4(2H)-yl)-2-methoxyethanone) with 3-formyl benzamide. The reaction can further be performed in the presence of a reducing agent. For example, the reducing agent can be STAB.

The method can also include making the compound of Formula XXI. In an embodiment, the method of making the compound of Formula XXI includes removing the Boc group from a compound of Formula XX, and replacing it with hydrogen:

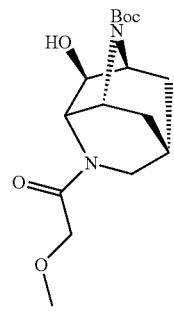 [SMILES: COCC(=O)N1C[C@@H]2C[C@@H]3C1[C@@H](O)[C@H](C2)N3C(=O)OC(C)(C)C]

((2S*,3S*,3aS*,6R*,7aR*)-tert-butyl 3-hydroxy-4-(2-methoxyacetyl)octahydro-1H-2,6-methanopyrrolo[3,2-b] pyridine-1-carboxylate). The Boc group can be removed with an acid. For example, the acid can be TFA.

The method can also include making the compound of Formula XX. In an embodiment, the method of making the compound of Formula XX includes removing the TBDPS group from a compound of Formula XIX, and replacing it with hydrogen:

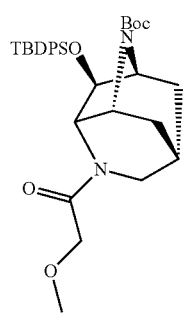

((2S*,3S*,6R*,7aR*)-tert-butyl 3-((tert-butyldiphenylsilyl) oxy)-4-(2-methoxyacetyl)octahydro-1H-2,6-methanopyrrolo[3,2-b]pyridine-1-carboxylate). For example, the TBPDS group can be removed with TBAF.

The method can also include making the compound of Formula XIX. In an embodiment, the method of making the compound of Formula XIX includes reacting a compound of Formula I.b, with 2-methoxyacetic acid. The reaction can further be performed with HATU and DIPEA.

BRIEF DESCRIPTION OF THE DRAWINGS

The preceding Summary, as well as the following Detailed Description of the invention, can be better understood when read in conjunction with the appended Figures. For the purpose of illustrating the invention, the Figures demonstrate embodiments of the present invention. However, it should be understood that the invention is not limited to the precise arrangements, examples, and instrumentalities shown.

FIG. 3A shows the results of a $^{1H}$NMR analysis of the compound of Formula X. FIG. 3B shows the results of a MS analysis of the compound of Formula X.

FIG. 8A shows the results of a MS analysis of the compound of Formula V. FIG. 8B shows the results of a $^{1H}$NMR analysis of the compound of Formula V.

FIG. 9A shows the results of a LCMS analysis of the compound of Formula IV. FIG. 9B shows the results of a $^{1H}$NMR analysis of the compound of Formula IV.

FIG. 11A shows the results of a $^{1H}$NMR analysis of the compound of Formula II. FIG. 11B shows the results of a LCMS analysis of the compound of Formula II.

FIG. 12A shows the results of a LCMS analysis of the compound of Formula I. FIG. 12B shows the results of a $^{1H}$NMR analysis of the compound of Formula I.

FIG. 17A shows the results of a LCMS analysis of the compound of Formula XVIII. FIG. 17B shows the results of a $^{1H}$NMR analysis of the compound of Formula XVIII.

FIG. 21A shows the results of a LCMS analysis of the compound of Formula XXII. FIG. 21B shows the results of a $^{1H}$NMR analysis of the compound of Formula XXII.

DETAILED DESCRIPTION

Figure 1:
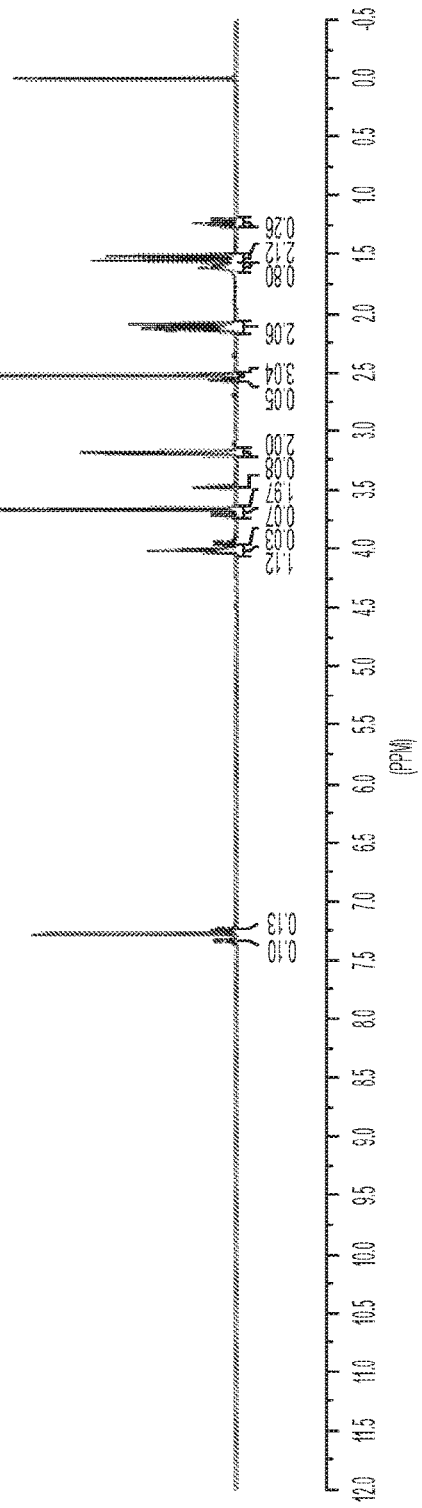
FIG. 1 shows the results of a $^{1H}$NMR analysis of the compound of Formula XII.

Embodiments of the invention are discussed in detail below. In describing these embodiments, specific terminology is employed for the sake of clarity. However, the invention is not intended to be limited to the specific terminology selected. A person skilled in the relevant art will recognize that other equivalent parts can be employed and other methods developed without parting from the spirit and scope of the invention.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

The term "halogen" represents chlorine, fluorine, bromine, or iodine. The term "halo" represents chloro, fluoro, bromo, or iodo.

The term "haloalkyl" refers to a straight- or branched-chain alkyl group having from 1 to 12 carbon atoms in the chain and having at least one of the hydrogens replaced with a halogen. In some embodiments, a haloalkyl group is a $C_1$-$C_6$ haloalkyl group. In some embodiments, a haloalkyl group is a $C_1$-$C_4$ haloalkyl group. One exemplary substituent is fluoro. Preferred substituted alkyl groups of the invention include trihalogenated alkyl groups such as trifluoromethyl groups. Haloalkyl includes and is not limited to CF$_3$, CH$_2$F, —CHF$_2$, —CH$_2$Cl, —CH$_2$—CF$_3$, and the like.

The term "alkoxy" includes a straight chain or branched alkyl group with a terminal oxygen linking the alkyl group to the rest of the molecule. In some embodiments, an alkoxy group is a $C_1$-$C_6$ alkoxy group. In some embodiments, an alkoxy group is a $C_1$-$C_4$ alkoxy group. Alkoxy includes methoxy, ethoxy, propoxy, isopropoxy, butoxy, t-butoxy, pentoxy and so on.

The term "heterocycle" represents a mono- or bi-cyclic hydrocarbon ring structure optionally containing heteroatoms selected from O, S, and N. Heterocyclyl rings can have 2 to 10 carbon atoms in the ring.

"Azacyclic" or "azacyclic ring" refers to a saturated, partially unsaturated, or aromatic 3-7 membered monocyclic ring or an 8-12 membered fused bicyclic ring system containing at least one nitrogen atom. Such azacyclic rings may optionally contain from 1-2 additional heteroatoms selected from N, O, and S as ring members, and may optionally be substituted to the extent such substitutions make chemical sense.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1] pentyl. In some embodiments, a cycloalkyl is a $C_3$-$C_6$cycloalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (═O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

A wavy line "⌇" indicates the point of attachment to the rest of the molecule.

"Benzyl" and —$CH_2$-phenyl are used interchangeably.

The term "acyl" is used herein as is conventional in the field of organic chemistry. For example, "acyl" can denote a carbonyl group with a bonded alkyl group.

The term "ester" is used herein as is conventional in the field of organic chemistry. For example, the term "ester" can denote a carbonyl group with a bonded oxygen and alkyl or an oxygen with a bonded carbonyl and alkyl.

The term "silyl" is used herein as is conventional in the field of organic chemistry. For example, the term "silyl" can denote a silicon atom to which hydrogen and/or alkyl groups can be bonded.

As used herein, the term "Boc-protection" denotes functionalization of a chemical compound with a tert-butyloxycarbonyl (Boc) group as a protecting group. This allows the chemical compound as a whole to be treated with reagents that would otherwise undesirably attack the unprotected group. The protected group can thereafter be deprotected to yield the desired original group.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

"Pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition.

Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

"Compounds of the present invention," and equivalent expressions, are meant to embrace compounds of the Formula as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

As used herein, the term "isotopic variant" refers to a compound that contains unnatural proportions of isotopes at one or more of the atoms that constitute such compound. For example, an "isotopic variant" of a compound can be radiolabeled, that is, contain one or more non-radioactive or radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. Radiolabeled compounds of the invention can be used in diagnostic methods such as Single-photon emission computed tomography (SPECT). The radioactive isotopes tritium, i.e. $^3$H, and carbon-14, i.e. $^{14}$C, are particularly useful for their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds of the invention, radioactive or not, are intended to be encompassed within the scope of the invention. In one aspect, provided herein are deuterated or tritiated analogs of compounds described.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

As used herein, the term "triturate" denotes a method of purifying a material in which the crude material is washed with a solvent. The solvent can be selected, so that the desired product is insoluble and the impurities are soluble, in which case, the purified product is left in solid form and the impurities are removed with the solvent. Conversely, the solvent can be selected, so that the desired product is soluble and the impurities are insoluble, in which case, the purified product is in solution and the impurities are removed as solids. The solvent can then be removed, for example, through evaporation, to obtain the purified product.

Compounds of the invention may also exist as "rotamers," that is, conformational isomers that occur when the rotation leading to different conformations is hindered, resulting a rotational energy barrier to be overcome to convert from one conformational isomer to another.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

As used herein, the term "localized delivery" denotes delivery of a pharmaceutical or therapeutic agent to a specific, limited region of the body.

As used herein, the term "systemic delivery" denotes delivery of a pharmaceutical or therapeutic agent throughout the body, for example, through administration to the circulatory system.

As used herein, the term "mass spectrometry (MS)" denotes an analytic technique that ionizes a chemical compound to generate charged molecules or molecule fragments and measures their abundance as a function of mass-to-charge (m/z) ratio (the mass spectrum). From the mass spectrum, conclusions as to the structure of the chemical compound can be drawn.

As used herein, the term "liquid chromatography-mass spectrometry (LCMS)" denotes an analytic technique that combines the physical separation capability of liquid chromatography with the analytic capability of mass spectrometry. In the liquid chromatography step, the sample is introduced into a column packed with a stationary phase, separating the chemical compounds of the sample by their retention time (Rt) in the column. The chemical compound or compounds associated with a retention time interval are then directed to a mass spectrometer, to obtain a mass spectrum that allows conclusions as to the structure of this chemical compound or compounds to be drawn.

As used herein, the term "thin-layer chromatography (TLC)" denotes an analytic technique that separates chemical compounds in a sample by the different rates in which they are drawn up a plate coated with a stationary phase material.

As used herein, the term "nuclear magnetic resonance spectroscopy (NMR)" denotes an analytic technique that measures the intensity of a resonance response of a set of nuclei to a radio frequency pulse to allow information as to the electronic environment of the nuclei to be obtained. From this, conclusions can be drawn as to the chemical structure of the compound in which the nuclei reside. A nuclear magnetic resonance spectroscopy technique that uses hydrogen nuclei (protons) is termed proton nuclear magnetic resonance spectroscopy ($^{1H}$NMR).

The present invention provides compounds of the Formula XXIII:

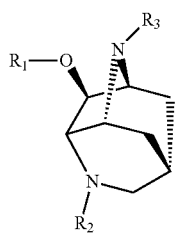

wherein $R_1$ is hydrogen, alkyl, acyl, or silyl;
$R_2$ is hydrogen, alkyl, benzyl, acyl, or ester; and
$R_3$ is hydrogen, alkyl, an aromatic group, azacyclic, carbocycle, aryl, cycloalkyl, heterocycloalkyl, heterocycle, heteroaryl, heteroalkyl, acyl, or ester, as well as derivatives and stereoisomers thereof.

In some embodiments, $R_1$ is optionally substituted with one or more substituents. In various embodiments, the optional substituents are selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, $R_2$ is optionally substituted with one or more substituents. In various embodiments, the optional substituents are selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

In some embodiments, $R_3$ is optionally substituted with one or more substituents. In various embodiments, the optional substituents are selected from halo, =O, =N—CN, =N—OR', =NR', OR', N(R')$_2$, SR', SO$_2$R', SO$_2$NR'$_2$, NR'SO$_2$R', NR'CONR'$_2$, NR'COOR', NR'COR', CN, COOR', CON(R')$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$ alkyl, $C_1$-$C_4$ heteroalkyl, $C_1$-$C_6$ acyl, $C_1$-$C_6$ heteroacyl, hydroxy, amino, and =O; wherein two R' can be linked to form a 3-7 membered ring optionally containing up to three heteroatoms selected from N, O and S.

The present invention provides a compound having the structure of Formula I:

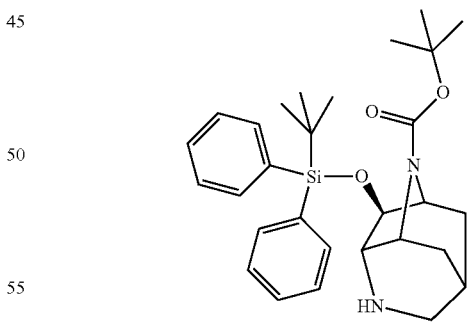

(2R,3S,6S,7aS)-tert-butyl 3-((tert-butyldiphenylsilyl)oxy) octahydro-1H-2,6-methanopyrrolo[3,2-b]pyridine-1-carboxylate, and stereoisomers thereof. This compound can be prepared by the reaction sequences described in Schemes 1-13 set forth in Example 1.

The present invention further provides therapeutic derivatives of the compound of Formula I, and methods for their synthesis. One such derivative is the compound of the Formula XVIII:

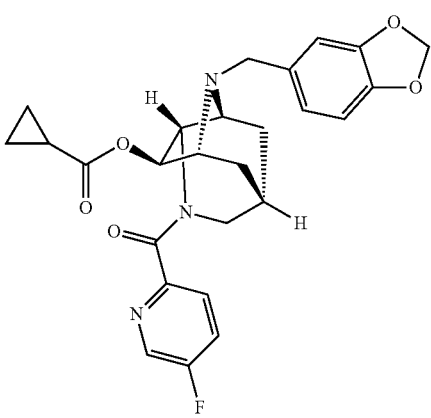 [SMILES: O=C(O[C@H]1[C@@H]2[C@@H]3C[C@@H](C[C@H]1N3Cc1ccc3c(c1)OCO3)CN2C(=O)c1ccc(F)cn1)C1CC1]

((2R*,3R*,3aS*,6S*,7aS*)-1-(benzo[d][1,3]dioxol-5-ylmethyl)-4-(5-fluoropicolinoyl)octahydro-1H-2,6-methanopyrrolo[3,2-b]pyridin-3-yl cyclopropanecarboxylate). This compound can be prepared by the reaction sequences described in Schemes 15-19 set forth in Example 2.

A second therapeutic derivative of the compound of Formula I is the compound of the Formula XXII:

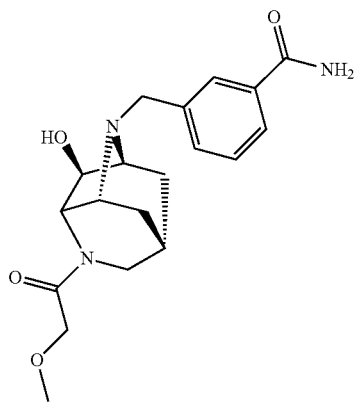 [SMILES: COCC(=O)N1C[C@@H]2C[C@@H]3C1[C@@H](O)[C@H](C2)N3Cc1cccc(C(N)=O)c1]

This compound can be prepared by the reaction sequences described in schemes 20-23 set forth in Example 3.

Pharmaceutical Compositions and Administration

The compounds of the present invention are useful as pharmaceutical agents and can be incorporated into pharmaceutical compositions comprising a therapeutically effective amount of a compound of the invention, as defined herein, and a pharmaceutically acceptable carrier or diluent.

The compounds of the invention can also be used in the manufacture of derivative compounds that are useful as pharmaceutical agents, and which can likewise be incorporated into pharmaceutical compositions prepared with a therapeutically effective amount of such a derivative compound and a pharmaceutically acceptable carrier or diluent.

The compounds of the invention, and such derivatives thereof, can be useful in the treatment of conditions, diseases, and disorders in humans and animals. Such compounds can be formulated as pharmaceutical compositions and administered to a subject in need of treatment, for example a mammal, such as a human patient, in a variety of forms adapted to the chosen route of administration. For example compounds of the invention may be formulated for administration, orally, nasally, intraperitoneally, or parenterally, by intravenous, intramuscular, topical, or subcutaneous routes, or by injection into tissue.

Thus, compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. The compounds may be combined with an inert powdered carrier and inhaled by the subject or insufflated. Such compositions and preparations should contain at least 0.1% of a compound of the present invention. The percentage of the compound of the invention present in such compositions and preparations may, of course, be varied and may conveniently be between about 2% to about 60% of the weight of a given unit dosage form. The amount of the compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or for otherwise modifying the physical form of the solid unit dosage form. For instance, tablets, pills, or capsules may be coated with gelatin, wax, shellac, or sugar, and the like. A syrup or elixir may contain the active compound, sucrose or fructose as a sweetening agent, methyl and propylparabens as preservatives, a dye, and flavoring such as cherry or orange flavor. Of course, any material used in preparing any unit dosage form should be pharmaceutically acceptable and substantially non-toxic in the amounts employed. In addition, the compounds may be incorporated into sustained-release preparations and devices. For example, the compounds may be incorporated into time release capsules, time release tablets, time release pills, and time release polymers or nanoparticles.

The compounds may also be administered intravenously or intraperitoneally by infusion or injection. Solutions of the compounds can be prepared in water, optionally mixed with a nontoxic surfactant. Dispersions can also be prepared in glycerol, liquid polyethylene glycols, triacetin, and mixtures thereof, and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are prepared by incorporating the compounds in the required amount in the appropriate solvent with various of the other ingredients enumerated above, as required, preferably followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the compounds may be applied in pure form. However, it may be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Other solid carriers include nontoxic polymeric nanoparticles or microparticles. Useful liquid carriers include water, alcohols, or glycols, or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

The concentration of the therapeutic compounds of the invention in such formulations can vary widely depending on the nature of the formulation and intended route of administration. For example, the concentration of the compounds in a liquid composition, such as a lotion, can preferably be from about 0.1-25% by weight, or, more preferably, from about 0.5-10% by weight. The concentration in a semi-solid or solid composition such as a gel or a powder can preferably be about 0.1-5% by weight, or, more preferably, about 0.5-2.5% by weight.

Effective dosages and routes of administration of agents of the invention are conventional. The exact amount (effective dose) of the agent will vary from subject to subject, depending on, for example, the species, age, weight, and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. Methods for the extrapolation of effective dosages in mice and other animals to humans are known to the art; for example, see U.S. Pat. No. 4,938,949, which is hereby incorporated by reference. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

The compounds are conveniently administered in unit dosage form; for example, containing about 0.05 to about 10000 mg, about 0.5 to about 10000 mg, about 5 to about 1000 mg, or about 50 to about 500 mg of active ingredient per unit dosage form.

The compounds can be administered to achieve peak plasma concentrations of, for example, from about 0.25 to about 200 µM, about 0.5 to about 75 µM, about 1 to about 50 µM, about 2 to about 30 µM, or about 5 to about 25 µM. Exemplary desirable plasma concentrations include at least 0.25, 0.5, 1, 5, 10, 25, 50, 75, 100 or 200 µM. For example, plasma levels may be from about 1 to about 100 micromolar or from about 10 to about 25 micromolar. This may be achieved, for example, by the intravenous injection of a 0.05 to 5% solution of the compounds, optionally in saline, or orally administered as a bolus containing about 1 to about 100 mg of the compounds. Desirable blood levels may be maintained by continuous or intermittent infusion.

The compounds may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations; such as multiple inhalations from an insufflator. All documents, references, and information, including, but not limited to, journal articles, patent applications, and patents, that are mentioned, cited, or referred to in this application are hereby incorporated by reference in their entirety as if each had been individually incorporated.

Example 1: Synthesis of a Compound of Formula I

A compound of Formula I was synthesized, from the compound of Formula XIII (Scopolamine [51-34-3]) ((2S)-

(1R,2R,4S,5S)-9-methyl-3-oxa-9-azatricyclo[3.3.1.02,4]nonan-7-yl-3-hydroxy-2-phenylpropanoate hydrobromide trihydrate) by the steps described below in Schemes 1 through 12.

A first step is illustrated in Scheme 1:

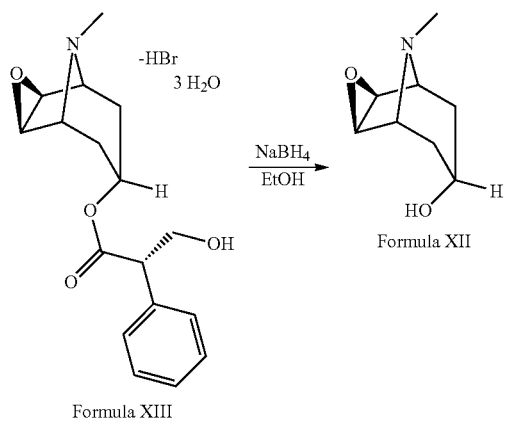

Formula XIII

Inside a 10 liter four necked round bottom flask, sodium borohydride (172 g, 4558 mmol) was added portion wise over about 2 hours to a mechanically stirred suspension of a compound of Formula XIII (333 g, 760 mmol) in 3 liters of absolute ethanol in an ice bath. During this time gas formation occurred and the suspension was stirred while being warmed to ambient temperature overnight. While being heated, at approximately 10° C., sudden additional gas formation and foaming occurred.

The milky suspension was then concentrated to about half of its original volume (i.e. from about 3 L to 1.5 L) with additional precipitate observed, which yielded the batch. Meanwhile, 5 M HCl in isopropyl alcohol (IPA) (5318 mmol, 1.064 L) was diluted with 2 L of technical diethyl ether (Et$_2$O). The obtained hydrochloric acid (HCl) solution was then added drop wise to the ice-chilled batch, while being stirred. The white suspension was allowed to be mechanically stirred overnight to allow for full hydrolysis of the borate salts.

The reaction mixture was filtered and the resulting solid was rinsed twice with 500 mL portions of Et$_2$O. The dried solid (which contained some Et$_2$O) was dissolved in a minimum amount of 10% aqueous potassium carbonate (K$_2$CO$_3$) solution (~1.5 L) until just a clear solution was obtained. 200 mL of brine and ~50 g solid NaCl was added to the solution. The aqueous phase was then thoroughly extracted with chloroform/methanol (MeOH)/[7N NH$_3$ in MeOH] (85:14:1). This procedure was performed 5 times with 1.0 L portions of this solvent mixture each. The combined organic extracts were dried (sodium sulphate (Na$_2$SO$_4$)), filtered and the solvent was removed under reduced pressure to give 102.2 g (659 mmol) of a compound of Formula XII ((1R,2R,4S,5S)-9-methyl-3-oxa-9-azatricyclo[3.3.1.02,4]nonan-7-ol) as a slightly tan oil at 87% yield. $^{1H}$NMR (CDCl$_3$) (FIG. 1) showed structural agreement with the compound of Formula XII with minor amounts of impurities. $^{1H}$NMR (400 MHz, Chloroform-d) δ 4.03-4.00 (m, 1H), 3.67 (s, 2H), 3.20-3.18 (m, 2H), 2.52 (s, 3H), 2.14-2.08 (m, 2H), 1.69-1.37 (m, 3H).

The next step proceeded as illustrated by Scheme 2:

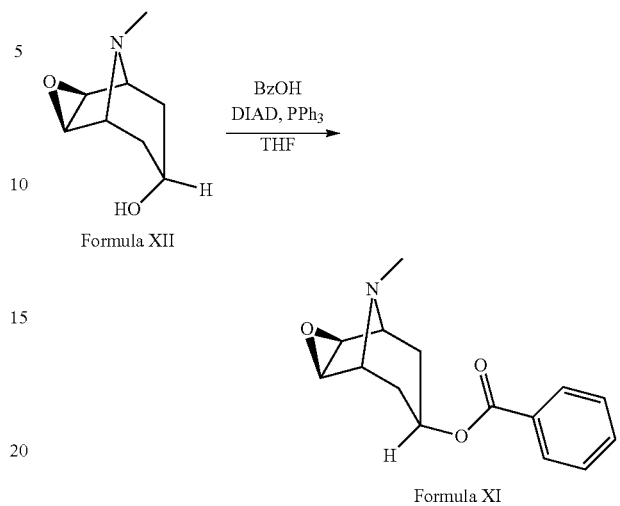

To a solution of the compound of Formula XII (102.2 g, 659 mmol), benzoic acid (BzOH) (97 g, 790 mmol) and triphenylphosphine (PPh$_3$) (207 g, 790 mmol) in 1000 mL of dry tetrahydrofuran (THF) a solution of diisopropyl azodicaboxylate (DIAD) (160 g, 790 mmol, 154 mL) in 100 mL of dry THF was added drop wise over a period of 4 hours. During the addition the solution was kept between −35 and −25° C. using acetone/dry ice. The clear, colorless solution was then removed from the ice bath and stirred at room temperature overnight.

Figure 2:
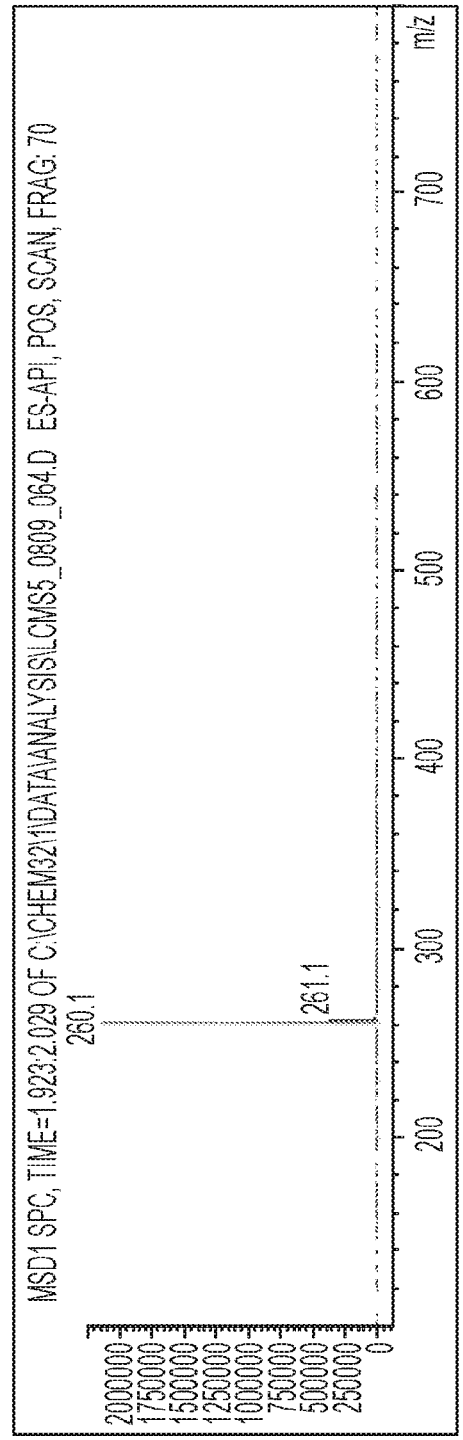
FIG. 2 shows the results of a MS analysis of the compound of Formula XI.

Samples were taken and analyzed, and the analysis showed the reaction went to completion. The reaction mixture was concentrated, dissolved in 1 L of ethyl acetate (EtOAc), extracted with 1 L of saturated sodium bicarbonate (NaHCO$_3$), and subsequently with aqueous 2 M HCl (1×1 L, 2×0.5 L). The combined acidic aqueous fractions were washed once more with 1 L of EtOAc. Approximately 400 g of potassium carbonate (K$_2$CO$_3$) was added portionwise to the acidic aqueous layer, while being stirred, until no more gas formation was observed. The pH of the resulting solution was slightly basic and slightly turbid and yellow. The aqueous phase was then extracted with a dichloromethane (DCM)/MeOH 9:1 (3×, 1 L each) solution and the combined organic fractions were dried with sodium sulfate (Na$_2$SO$_4$), filtered and concentrated to afford 118.3 g (447 mmol) of a compound of Formula XI ((1R,2R,4S,5S,7r)-9-methyl-3-oxa-9-azatricyclo[3.3.1.02,4]nonan-7-yl benzoate), which was then confirmed by MS (FIG. 2) to have 98% purity at 67.9% yield. $^{1H}$NMR (400 MHz, Chloroform-d) δ 8.07-7.93 (m, 2H), 7.59-7.48 (m, 1H), 7.44-7.40 (m, 2H), 5.39-5.30 (m, 1H), 3.63 (s, 2H), 3.42-3.25 (m, 2H), 2.57 (s, 3H), 2.10-2.04 (m, 2H), 1.92-1.86 (m, 2H).

The next step proceeded as illustrated in Scheme 3:

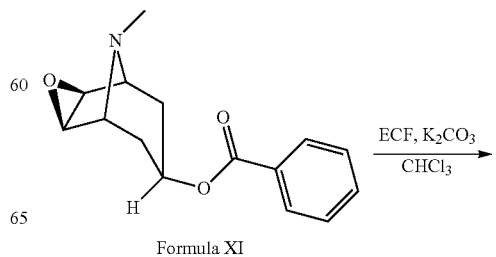

Formula XI

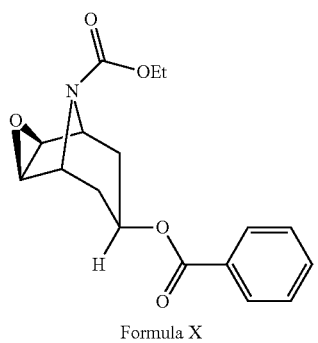

Formula X

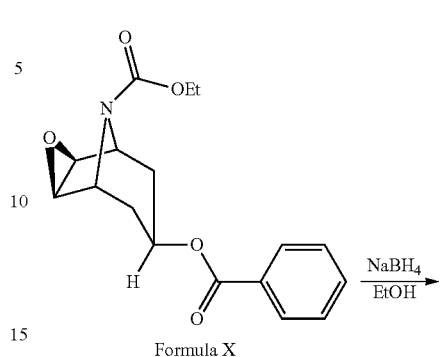

Formula X

To a solution of the compound of Formula XI (201.9 g, 779 mmol) in chloroform (350 mL) under a nitrogen atmosphere (not a stream), K$_2$CO$_3$ (452 g, 3270 mmol) and ethyl chloroformate (279 g, 2569 mmol, 247 mL) were added to form a light yellow suspension which was then stirred under reflux overnight.

A sample was then taken and analyzed to show that the reaction had reached a 74% conversion to the product, a compound of Formula X (1R,2R,4S,5S,7r)-ethyl 7-(benzoyloxy)-3-oxa-9-azatricyclo[3.3.1.02,4] nonane-9-carboxylate). The mixture was further stirred at reflux temperature for another 24 hours.

Another sample was then taken and analyzed which showed that the reaction had reached a 75% conversion to product. In order to drive the reaction toward completion, additional K$_2$CO$_3$ (53.8 g, 389 mmol) and ethyl chloroformate (85 g, 779 mmol, 74.8 mL) were added to the reaction solution and the mixture was stirred at reflux temperature overnight.

After being stirred and refluxed overnight, another sample was taken which was analyzed to show that the reaction had reached a 81% conversion to the compound of Formula X.

The reaction mixture was then diluted with 500 mL of DCM and the organic layer was washed with 750 mL of a half saturated aqueous NaHCO$_3$ solution, 750 mL of 0.4 M aqueous HCl, and 750 mL of brine. The mixture next dried over Na$_2$SO$_4$, then filtered and concentrated under reduced pressure which then afforded a yellow oil. 300 mL of Heptane was added and the mixture was vigorously stirred overnight.

Figure 3A:
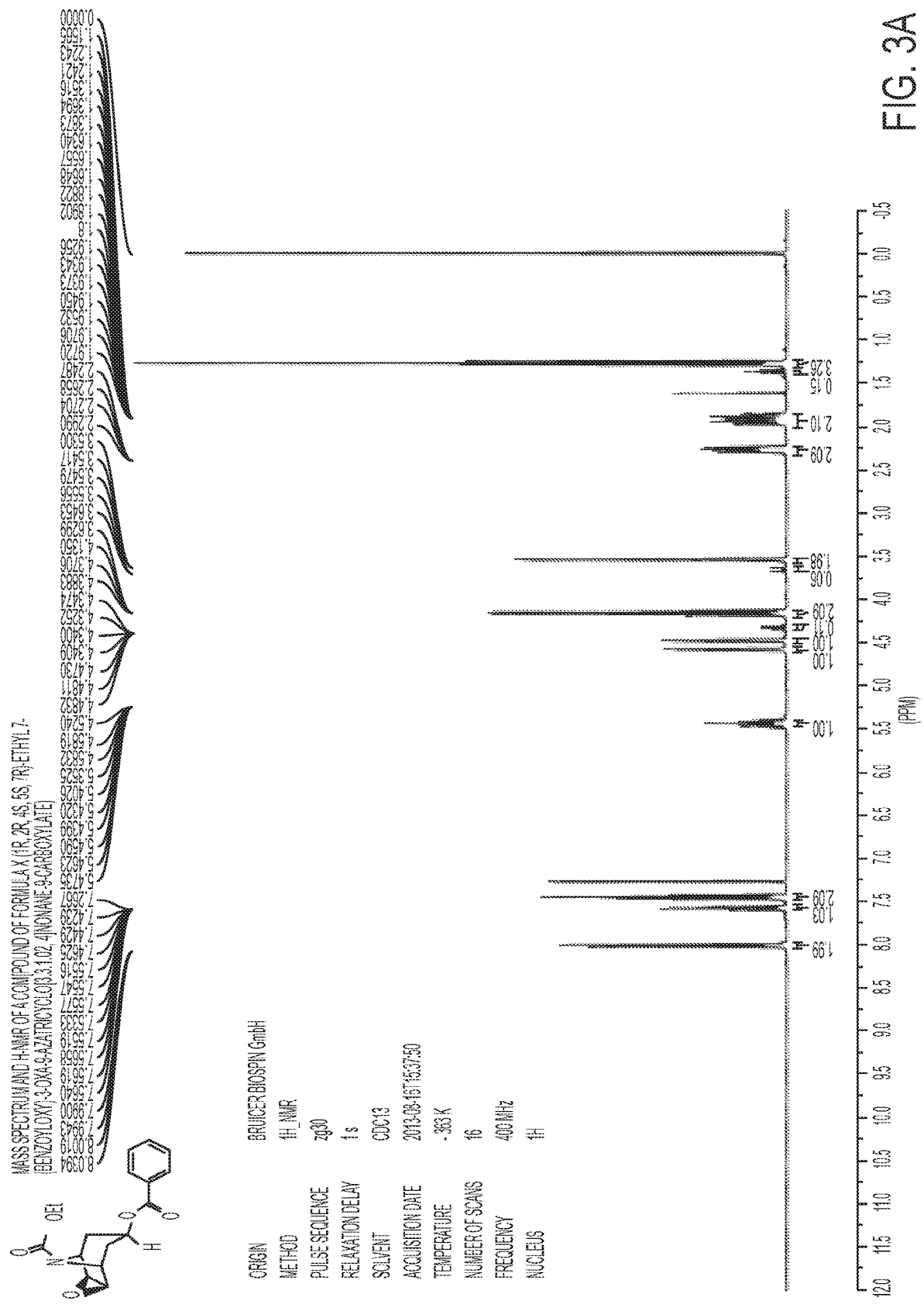
FIGS. 3A and 3B show the results of a structural analysis of the compound of Formula X.
Figure 3B:
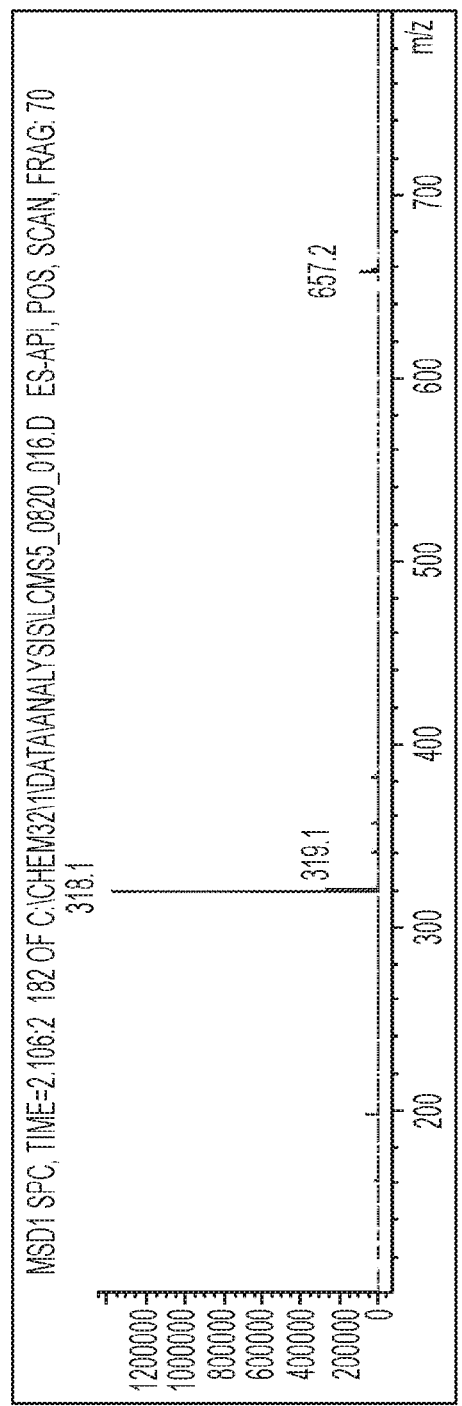

A white suspension had formed which contained big white lumps which were crushed with a spatula. The suspension was filtered over a glass filter, rinsed with approximately 250 mL of heptane and approximately 200 mL of pentane. The suspension was then dried using a vacuum oven for 3 hours yielding the compound of Formula X as a white solid (219.6 g, 692 mmol, 89% yield). LCMS of the product showed a percent yield greater than 95%, with a mass and structure agreement with the desired product as shown in the MS (FIG. 3B) and $^{1H}$NMR (FIG. 3A)). $^{1H}$NMR (400 MHz, Chloroform-d) δ 8.01-7.97 (m, 2H), 7.61-7.53 (m, 1H), 7.48-7.42 (m, 2H), 5.48-5.39 (m, 1H), 4.58 (m, 1H), 4.48 (m, 1H), 4.16 (q, J=7.1 Hz, 2H), 3.56-3.53 (m, 2H), 2.34-2.21 (m, 2H), 1.98-1.86 (m, 2H), 1.27 (t, J=7.1 Hz, 3H).

The next step proceeded as illustrated in Scheme 4:

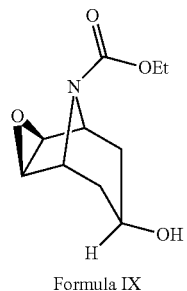

Formula IX

In a 6 L three necked flask, sodium borohydride (157 g, 4152 mmol) was added to a suspension of the compound of Formula X (219.6 g, 692 mmol) in 1.5 L of absolute ethanol at room temperature. The reaction was exothermic, and had an internal temperature greater than 60° C. over a period of approximately 4 hours, during the reaction extreme gas/foam formation was observed. The suspension was magnetically stirred at 50° C. overnight.

A sample was then taken and analyzed by TLC to show that the reaction had gone to completion. The resulting product was a white solid which stopped the magnetic stirrer during the night. The mixture was concentrated under reduced pressure and the white solid residue was partitioned between 1 L of chloroform and 3.5 L of half-saturated aqueous NaHCO$_3$ solution. The layers were next separated and the aqueous layer was extracted with additional chloroform (2×, 1 L each). The combined organic layers were washed with 1 L of brine, dried over Na$_2$SO$_4$, and filtered and concentrated under reduced pressure to afford approximately 220 g of the product as a white solid which was stirred in 0.6 L of heptane overnight with a magnetic stirrer.

The mixture was then filtered off, the product had formed spheres which were crushed and had 500 mL of heptane added to them. The mixture was stirred vigorously overnight with a magnetic stirrer.

Figure 4:
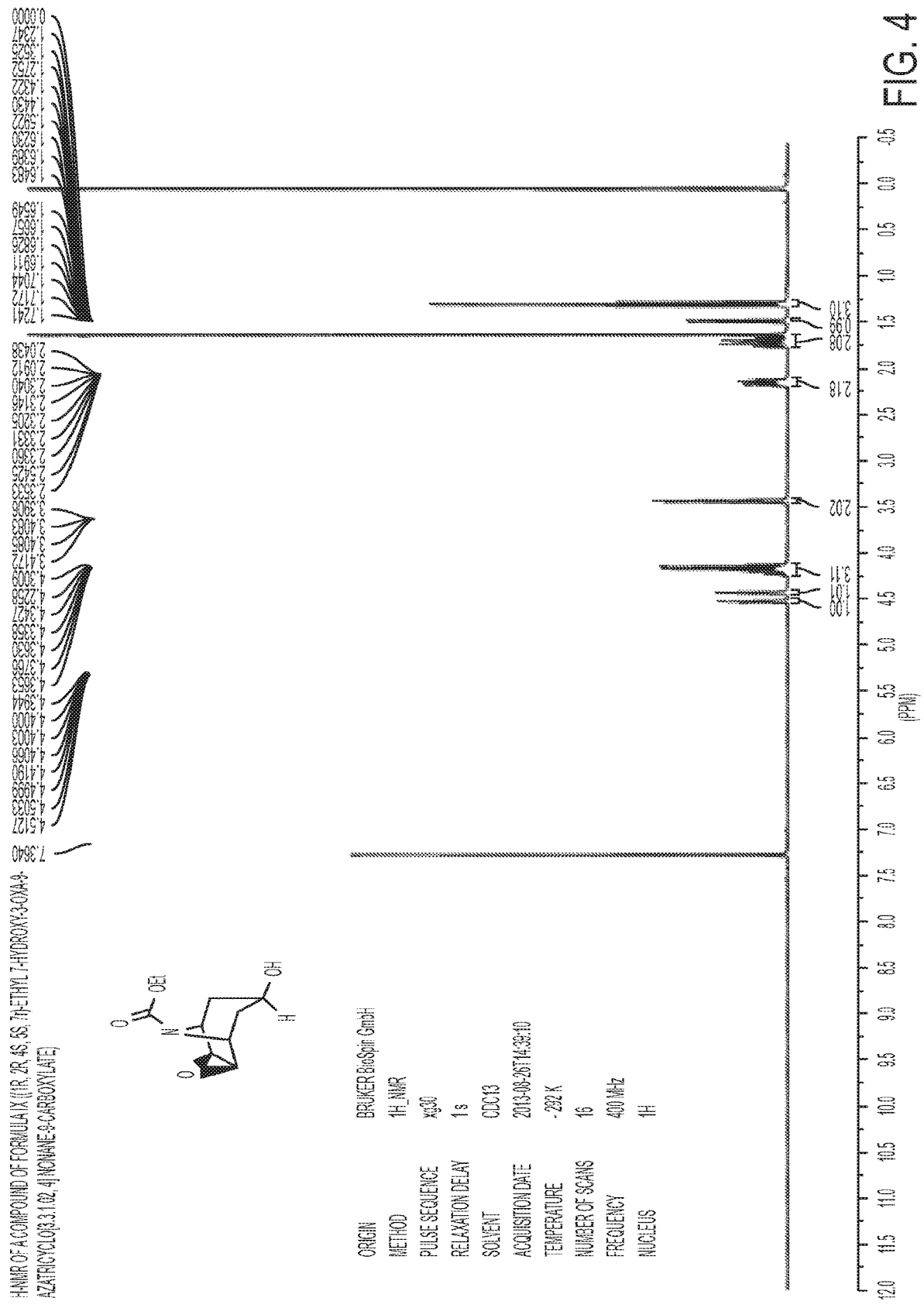
FIG. 4 shows the results of a $^{1H}$NMR analysis of the compound of Formula IX.

After stirring the mixture overnight, the off-white suspension still contained spheres which then were crushed with a spatula. The suspension was filtered and the residue was rinsed with approximately 300 mL heptane and dried by vacuum which yielded approximately 148 g of the product. A sample was taken and analysed by $^{1H}$NMR to show the structure was in agreement with the compound of Formula IX (1R,2R,4S,5S,7r)-ethyl 7-hydroxy-3-oxa-9-azatricyclo [3.3.1.02,4]nonane-9-carboxylate), (FIG. 4).

The residue was stirred in approximately 300 mL of Et$_2$O for 1 hour. The white suspension was filtered; and the residue was rinsed again with approximately 300 mL of Et$_2$O and then dried by vacuum (under N$_2$-flow) to yield the compound of Formula IX (122 g, 572 mmol, 82% yield). $^{1H}$NMR (400 MHz, Chloroform-d) δ 4.50 (m, 1H), 4.41 (m, 1H), 4.23-4.09 (m, 3H), 3.42-3.39 (m, 2H), 2.15-2.08 (m, 2H), 1.73-1.62 (m, 2H), 1.44 (d, J=5.9 Hz, 1H), 1.26 (t, J=7.1 Hz, 3H).

The next step proceeded as illustrated in Scheme 5:

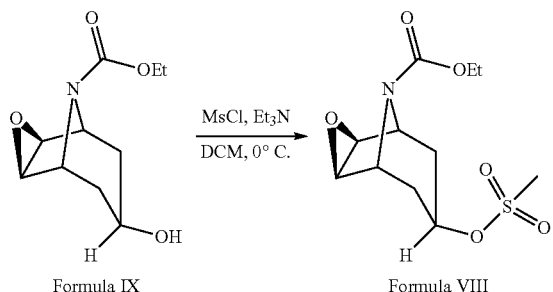 [SMILES: CCOC(=O)N1C2CC(O)CC1[C@@H]1O[C@H]21 ; CCOC(=O)N1C2CC(OS(C)(=O)=O)CC1[C@@H]1O[C@H]21]

Formula IX → Formula VIII

Triethylamine (22.78 g, 225 mmol, 31.4 mL) and mesyl-Cl (23.64 g, 206 mmol, 16.08 mL) was added drop wise to a solution of the compound of Formula IX (40 g, 188 mmol) in DCM (500 mL) at 0° C. Once the addition was complete, the ice bath was removed and the slightly milky suspension was stirred while warming to room temperature.

After 1 hour a sample was taken and analyzed by TLC which showed full conversion had occurred. The reaction mixture was then washed twice with 500 mL of water. The DCM layer appeared milky and was dried over Na$_2$SO$_4$ (which made the layer clearer), and then filtered and concentrated under reduced pressure to afford a thick oil. The oil was stripped twice with toluene to afford 54.2 g of a light tan solid which contained 21 w % toluene.

Figure 5:
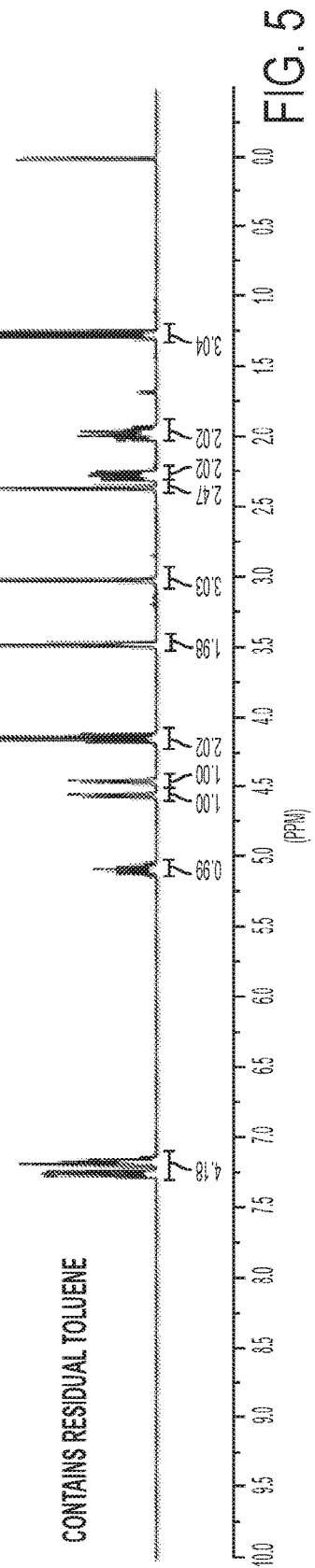
FIG. 5 shows the results of a $^{1H}$NMR analysis of the compound of Formula VIII.

The solid was further dried under vacuum at 50° C. until the weight remained constant at 43.2 g (148 mmol; 78.9% yield) yielding a compound of Formula VIII ((1R,2R,4S,5S,7r)-ethyl 7-((methylsulfonyl)oxy)-3-oxa-9-azatricyclo [3.3.1.02,4]nonane-9-carboxylate). A sample was taken and the structure was confirmed by $^{1H}$NMR (FIG. 5). $^{1H}$NMR (400 MHz, Chloroform-d) δ 5.11-5.02 (m, 1H), 4.54-4.53 (m, 1H), 4.44-4.43 (m, 1H), 4.13 (q, J=7.1 Hz, 2H), 3.47-3.45 (m, 2H), 3.00 (s, 3H), 2.28-2.23 (m, 2H), 2.00-1.90 (m, 2H), 1.25 (t, J=7.1 Hz, 3H).

The next step proceeded as illustrated in Scheme 6:

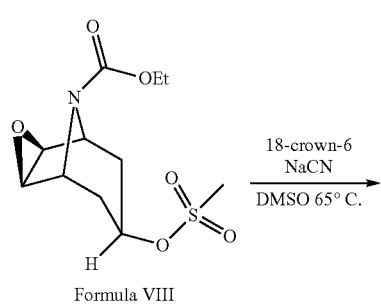

Formula VIII

-continued

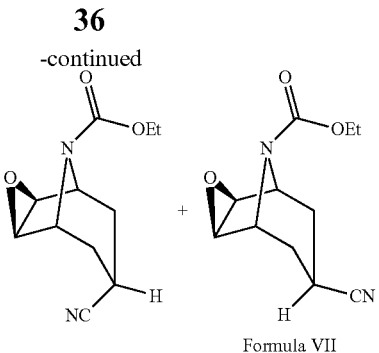

Formula VII

Potassium cyanide (12.14 g, 186 mmol) and 18-crown-6 (1,4,7,10,13,16-hexaoxacyclooctadecane) (0.493 g, 1.864 mmol) were added to a solution of the compound of Formula VIII (19.89 g, 62.1 mmol, 91%) in 300 mL of dry Dimethyl sulfoxide to form a pale yellow solution which was stirred at 65° C. for two and a half days, or approximately 65 hours, to yield a light brown solution. A sample was taken and analyzed by TLC (heptane/DME 1:1, molybdate staining required), which showed a clean conversion to the desired product (no exo-epimeric sideproduct observed), however, the reaction had not run to completion as starting material was also observed.

The stirring was continued for a total of 118 hours, after which the brown solution was allowed to cool to room temperature, and combined with an additional batch before being partitioned between 2 L of EtOAc and 2 L of water. The layers were separated and the organic layer was washed twice with 1 L of brine, dried over Na$_2$SO$_4$, and filtered and concentrated under reduced pressure to afford the crude product, a compound of Formula VII ((1R,2R,4S,5S,7s)-ethyl 7-cyano-3-oxa-9-azatricyclo [3.3.1.02,4]nonane-9-carboxylate).

Figure 6:
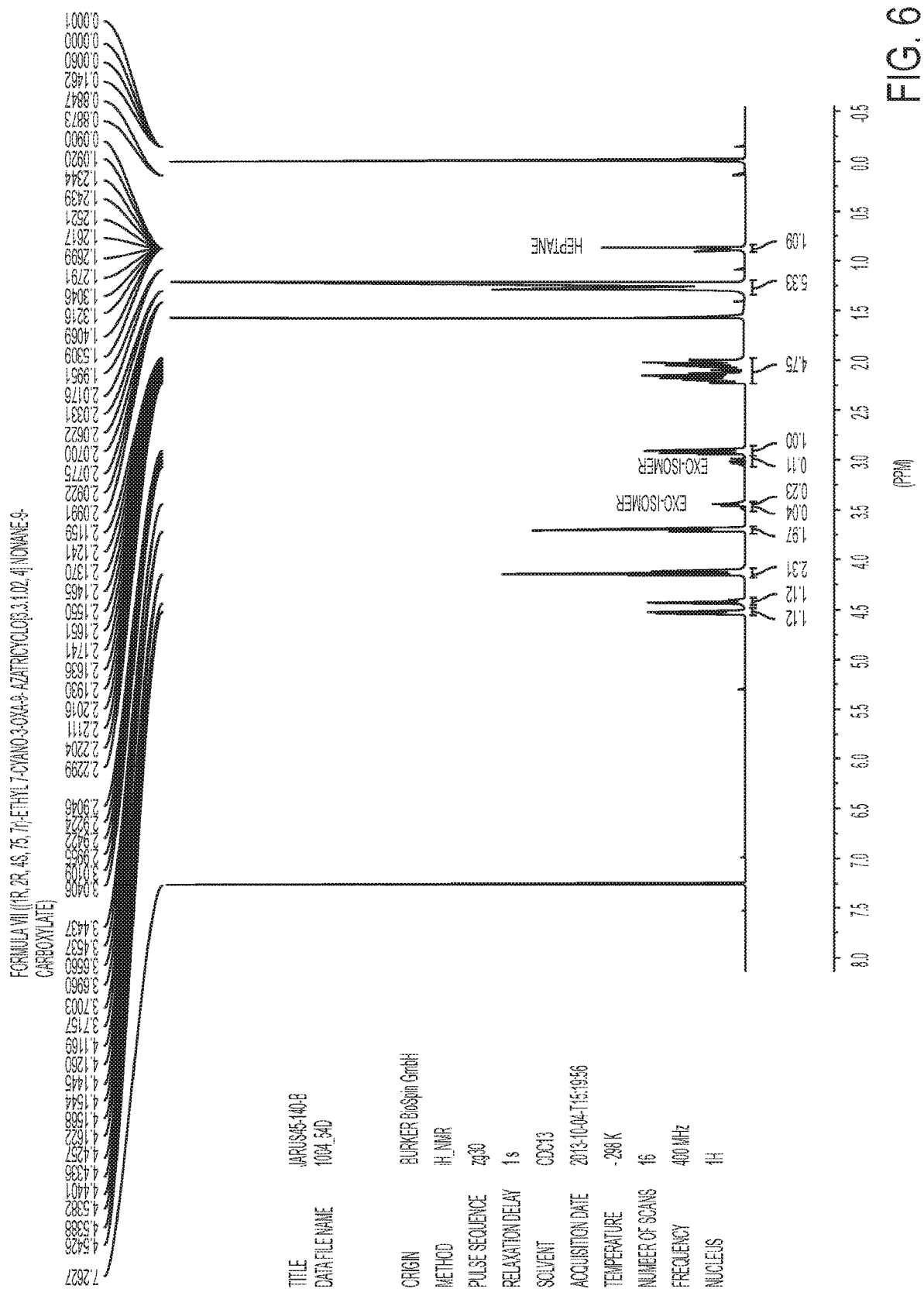
FIG. 6 shows the results of a $^{1H}$NMR analysis of the compound of Formula VII

The resulting product was purified by gravity column chromatography (750 g silica, heptane/[5->50% EtOAc]) to afford 15.1 g of a white solid, or a compound of Formula VII. A sample was taken and analyzed by $^{1H}$NMR (FIG. 6) which demonstrated the product was in agreement with the structure of Formula VII, although the product did contain 10 w % of the exo-sideproduct (which was not problematic for the follow-up reactions) and 7.5 w % of heptane. The combined yield from all experiments was 7.55 g, or 45% yield, after correction for solvent and side product content. $^{1H}$NMR (400 MHz, Chloroform-d) δ 4.53-4.52 (m, 1H), 4.43-4.41 (m, 1H), 4.12 (q, J=7.1 Hz, 2H), 3.70-3.68 (m, 2H), 2.93-2.89 (m, 1H), 2.22-2.12 (m, 2H), 2.04-1.98 (m, 2H), 1.24 (t, J=7.1 Hz, 3H).

The next step proceeded as illustrated in Scheme 7:

Formula VII

1) H$_2$, Ra—Ni, NH$_3$, MeOH
2) EtOH, reflux

-continued

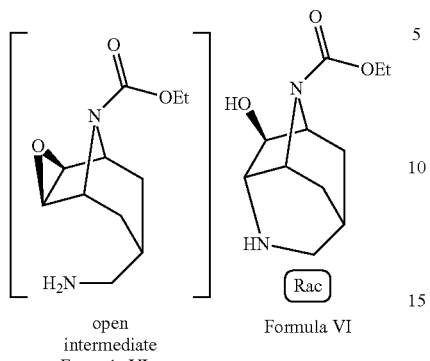

open intermediate
Formula VI.a

Formula VI

A 50% slurry of Raney-nickel in water was added to a solution of the compound of Formula VII (18.20 g, 82 mmol) in 350 mL of MeOH/200 mL of ammonia (7N in MeOH). The solution was kept under a nitrogen atmosphere and the Raney-nickel slurry was added until a dark black suspension was obtained while being stirred vigorously. The reaction vessel was evacuated and refilled with $H_2$ balloons, which was repeated twice, and then stirred at 45° C. under a $H_2$ atmosphere created by the balloons. After 3 hours, a sample was taken and analyzed by TLC using heptane/dimethoxyethane (DME) 1:1, which demonstrated the reaction was complete.

The reaction mixture was filtered over a short pad of celite which was pre-rinsed with MeOH. The residue was also rinsed with additional MeOH. The filtrate was concentrated under reduced pressure to give a light yellow oil. This crude product consisted mainly of the open amines of a compound of Formula VI.a (1R,2R,4S,5S,7s)-ethyl 7-(aminomethyl)-3-oxa-9-azatricyclo[3.3.1.02,4]nonane-9-carboxylate and to a lesser extent the (desired) cyclized amine a compound of Formula VI (rac-(2R,3S,6S,7aS)-ethyl 3-hydroxyoctahydro-1H-2,6-methanopyrrolo[3,2-b]pyridine-1-carboxylate).

Figure 7:
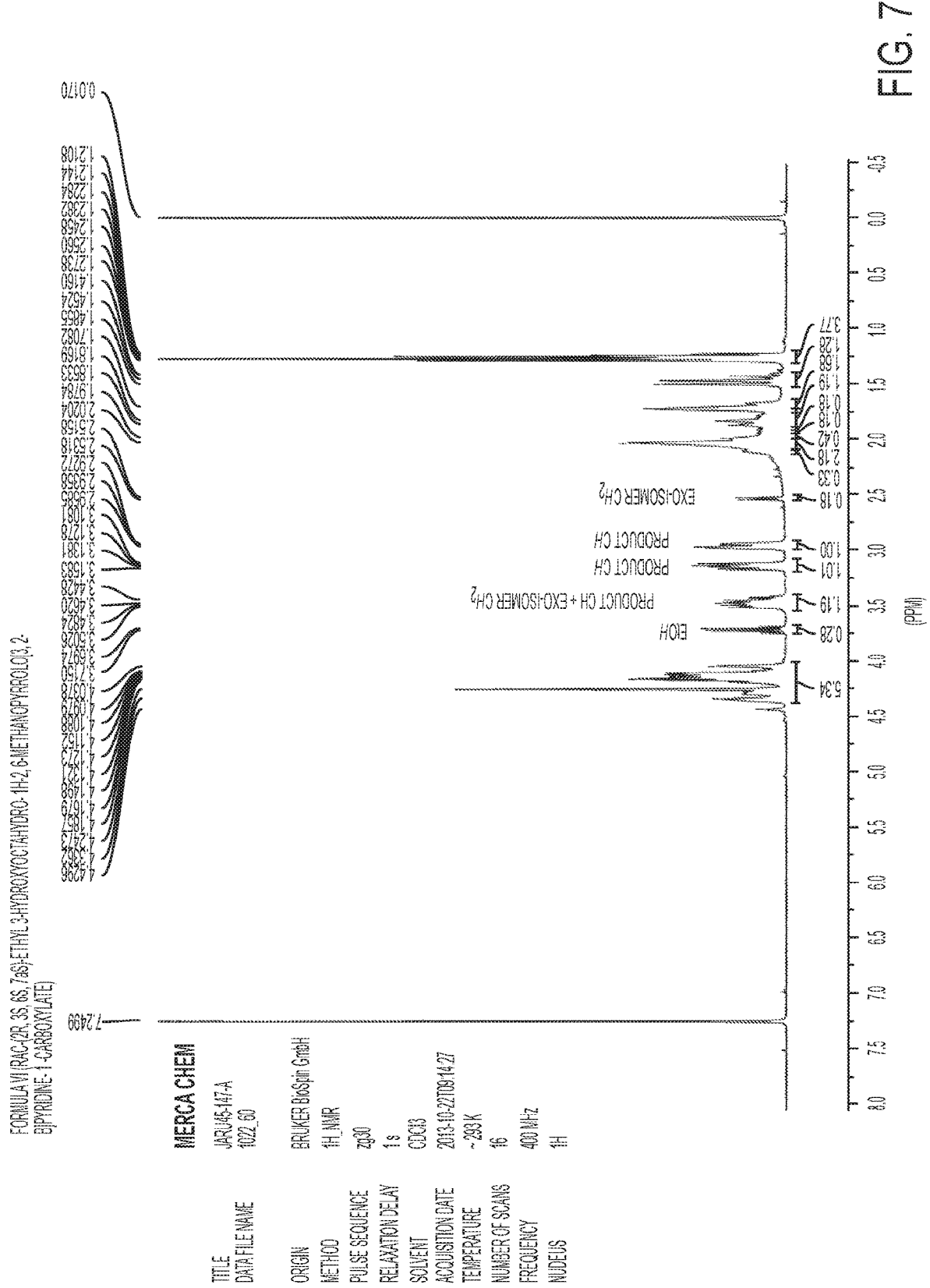
FIG. 7 shows the results of a $^{1H}$NMR analysis of the compound of Formula VI.

To drive cyclization of the main endo-isomer to completion, the intermediate was dissolved in 500 mL of absolute ethanol, which created a light yellow solution, which was then stirred and refluxed overnight. A sample was taken, concentrated under reduced pressure, dissolved in $CDCl_3$, and analyzed by $^{1H}$NMR (FIG. 7) which showed the intermediate, open endo-isomer, had cyclized. It was further shown that approximately 9% of the product was open exo-amine, and some solvent remained. $^{1H}$NMR (400 MHz, Chloroform-d) δ 4.46-4.01 (m, 5H), 3.50-3.44 (m, 1H), 3.16-3.11 (m, 1H), 3.96-2.93 (m, 1H), 2.10-1.66 (m, 5H), 1.47 (d, J=13.3 Hz, 1H), 1.26 (t, J=7.1 Hz, 3H).

The main batch, a yellow solution, was concentrated under reduced pressure and the residue was redissolved in 500 mL of $CHCl_3$ and dried over $Na_2SO_4$. The solution was filtered and concentrated to give 21.7 g of a compound of Formula VI as a thick yellow oil which contained solvent and the open exo-amine which was used in the next step.

The next step proceeded as illustrated in Scheme 8:

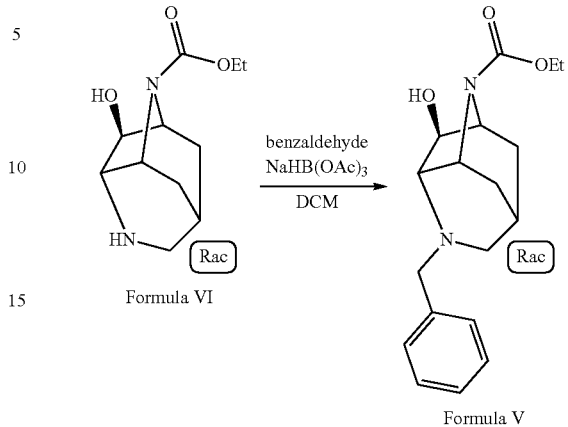

Formula VI

Formula V

Benzaldehyde (22.74 g, 214 mmol, 21.72 mL) was added to a solution of the compound of Formula VI (37.3 g, 165 mmol) in 1000 mL of dichloromethane. After 15 minutes STAB (55.9 g, 264 mmol) was added. The suspension was then stirred at room temperature overnight.

Figure 8A:
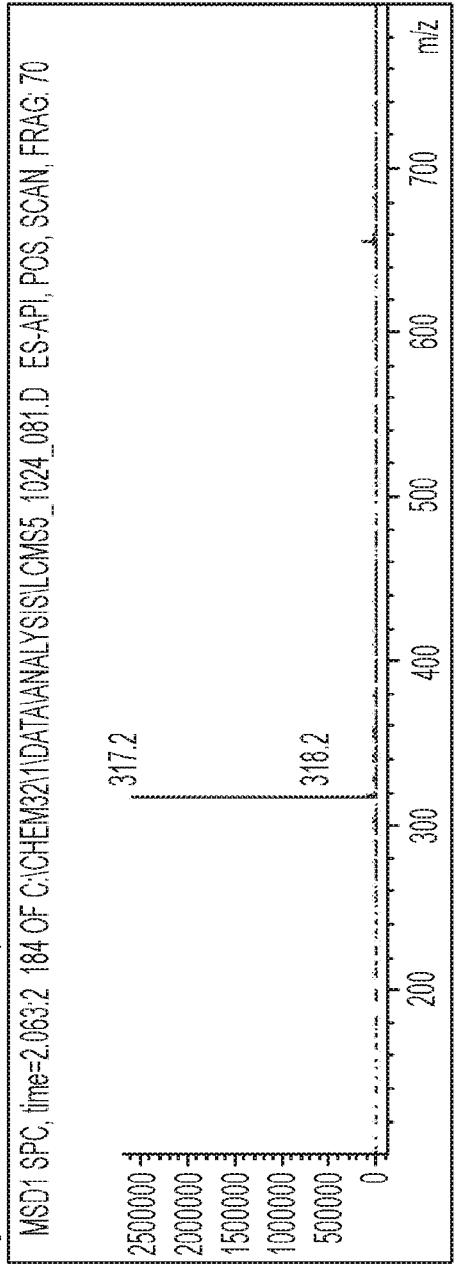
FIGS. 8A and 8B show the results of a structural analysis of the compound of Formula V.
Figure 8B:
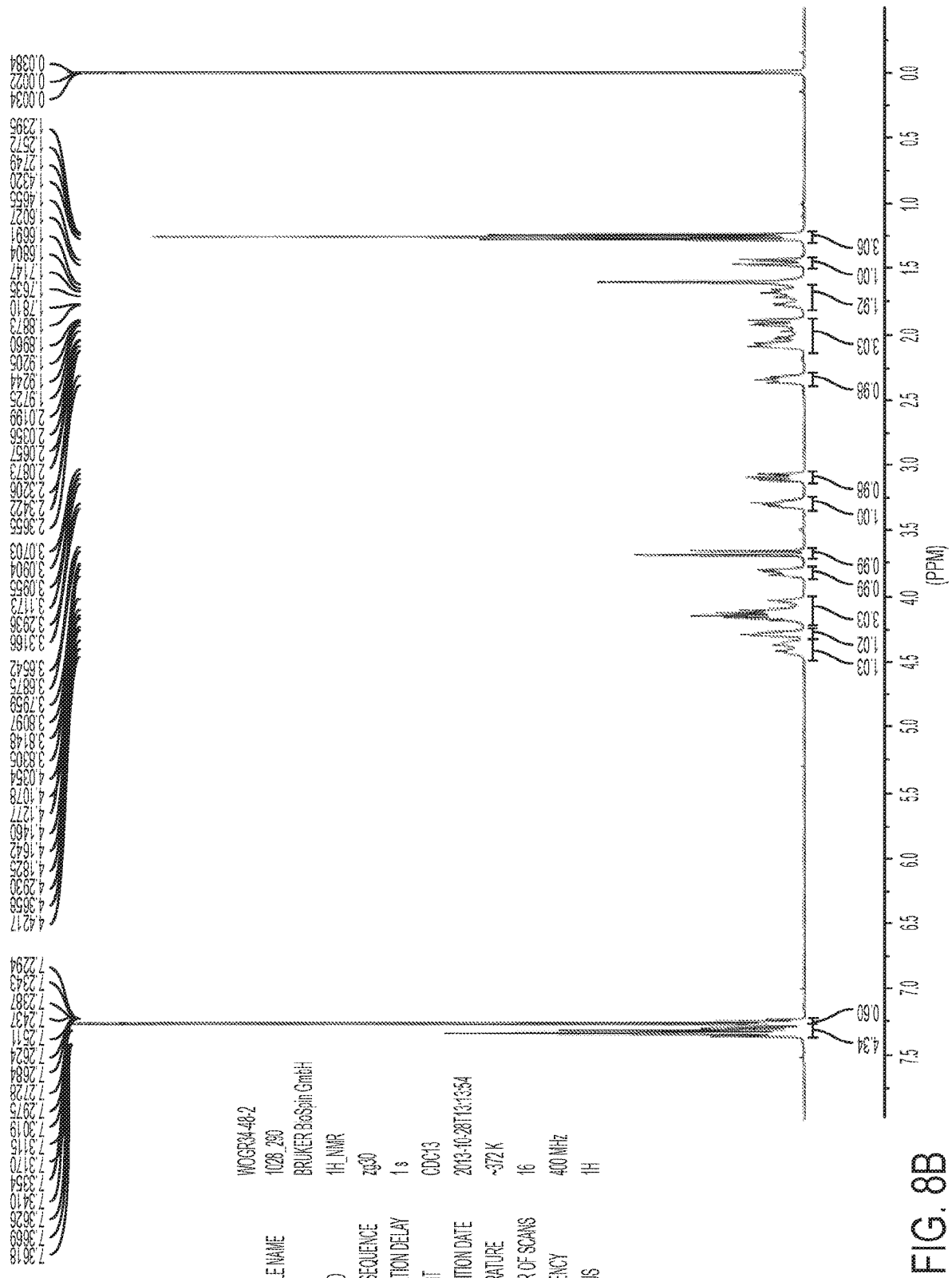

The reaction mixture was washed with 1 L of water and 1 L $NaHCO_3$. The organic layer was dried with $Na_2SO4_2$ and concentrated to dryness to afford 55 g of the reacted product, which was next purified by gravity column chromatography ("600 g, Hep/5-60% ETOAc) affording: 2.2 g of exo-Bn2N-adduct; and 35.3 g of a compound of Formula V (rac-(2R,3S,6S,7aS)-ethyl 3-hydroxyoctahydro-1H-2,6-methanopyrrolo[3,2-b]pyridine-1-carboxylate) as analyzed and confirmed by $^{1H}$NMR (FIG. 8B) and MS (FIG. 8A). $^{1H}$NMR (400 MHz, Chloroform-d) δ 7.35-7.30 (m, 4H), 7.26-7.22 (m, 2H), 4.41-4.02 (m, 5H), 3.83-3.78 (m, 1H), 3.66 (d, J=13.3 Hz, 1H), 3.30-3.26 (m, 1H), 3.11-3.06 (m, 1H), 2.35-2.31 (m, 1H), 2.07-1.88 (m, 3H), 1.77-1.65 (m, 2H), 1.44 (d, J=13.9 Hz, 1H), 1.25 (t, J=7.1 Hz, 3H).

The next step proceeded as illustrated in Scheme 9:

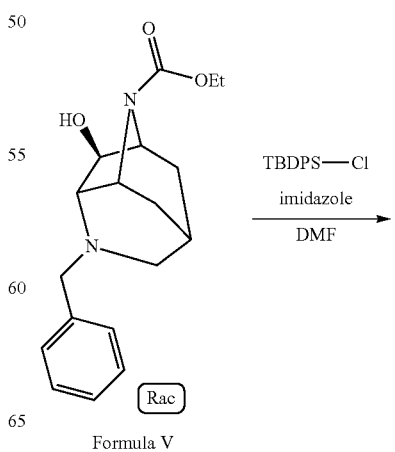

Formula V

TBDPS—Cl
imidazole
DMF

-continued

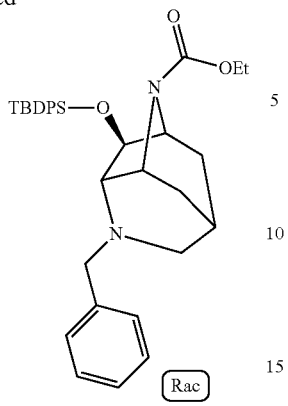

Formula IV

Imidazole (15.19 g, 223 mmol) and tert-butyldiphenylchlorosilane (30.7 g, 112 mmol, 28.7 mL) were added to a solution of the compound of Formula V (35.3 g, 112 mmol) in 100 mL of dry N,N-dimethylformamide to form a pale yellow solution which was stirred at room temperature overnight.

After the stirring was complete a sample was taken and analyzed by LCMS which showed the reaction was complete.

The solution was then concentrated under reduced pressure to yield an oily residue which was diluted with 750 mL of DCM and washed with 750 mL of 1:1 saturated aqueous $NaHCO_3$ solution and water. Next the solution was washed with 750 mL of brine. The organic layer was dried over $Na_2SO_4$, filtered, and concentrated to afford approximately 65 g of the reacted product as confirmed by TLC.

Figure 9A:
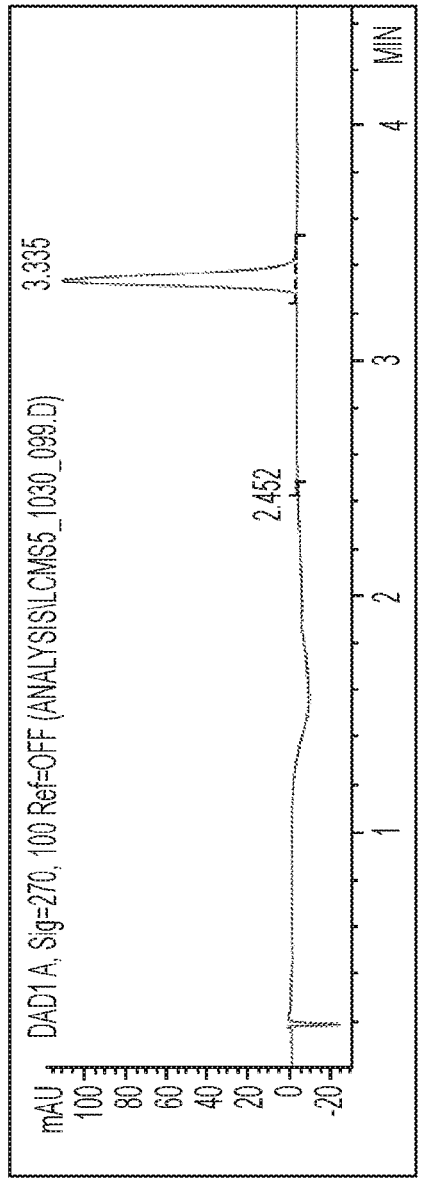
FIGS. 9A and 9B show the results of a structural analysis of the compound of Formula IV.
Figure 9A:
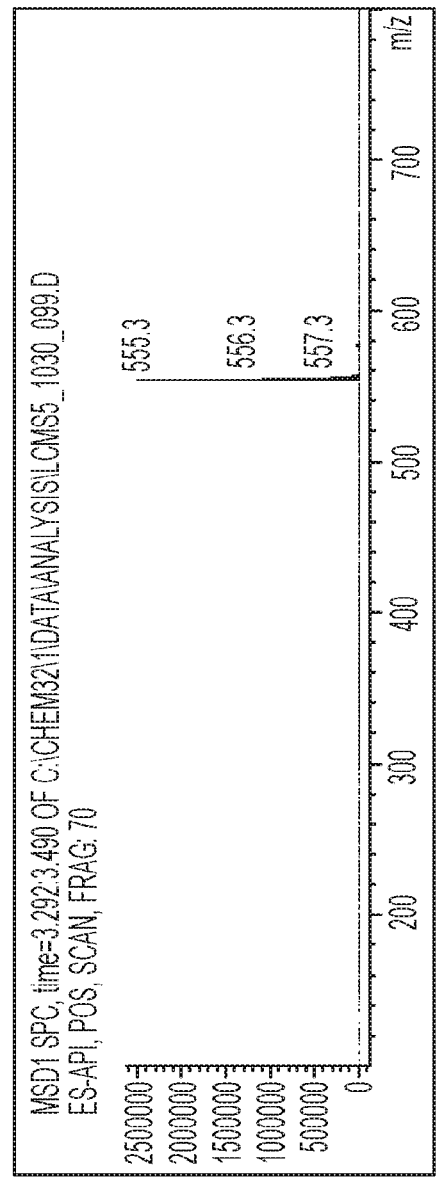
Figure 9B:
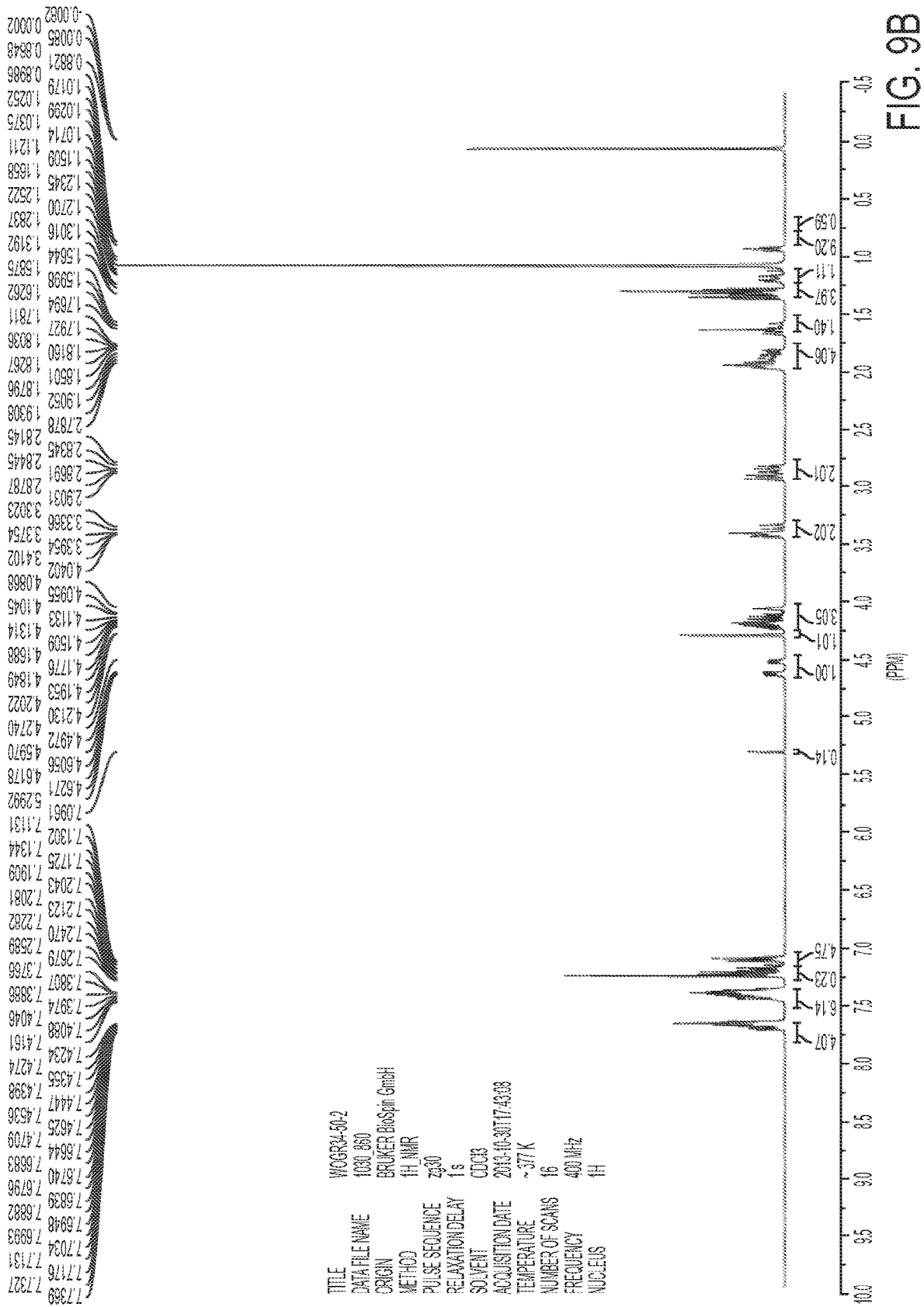

The reacted product was purified by gravity column chromatography (approximately 600 g, Hep/5-15% EtOAc) which afforded 59.5 g, or a 90% yield, of a compound of Formula IV (rac-(2R,3R,6S,7aS)-ethyl 4-benzyl-3-((tert-butyldiphenylsilyl)oxy)octahydro-1H-2,6-methanopyrrolo[3,2-b]pyridine-1-carboxylate) as a very thick colorless oil. A sample was taken and analyzed by $^{1H}$NMR (FIG. 9B) and LCMS (FIG. 9A), which showed the product was in agreement with the structure of Formula IV and contained 6 w/w % heptane. $^{1H}$NMR (400 MHz, Chloroform-d) δ 7.72-7.66 (m, 4H), 7.47-7.36 (m, 6H), 7.26-7.16 (m, 3H), 7.12-7.09 (m, 2H), 4.62-4.48 (m, 1H), 4.26 (s, 1H), 4.22-4.03 (m, 3H), 3.40-3.29 (m, 2H), 2.89-2.78 (m, 2H), 1.92-1.76 (m, 4H), 1.62-1.52 (m, 1H), 1.31-1.23 (m, 3H), 1.17-1.11 (m, 1H), 1.02 (s, 9H).

The next step proceeded as illustrated in Scheme 10:

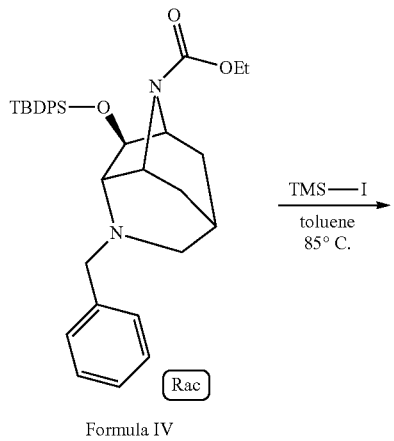

Formula IV

-continued

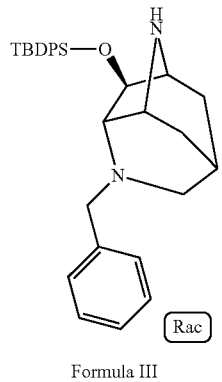

Formula III

Iodotrimethylsilane (75.0 g, 375 mmol, 51 ml) was added to a solution of the compound of Formula IV (73.9 g, 124 mmol, 93%) in 1.2 L of dry toluene to create a yellow reaction mixture which was stirred at 85° C. overnight.

A sample taken then taken and analyzed by TLC, which showed the reaction had gone to completion. The resulting reaction mixture was a dark solution, and was allowed to cool to room temperature (suspension) and quenched with 250 mL of MeOH. The mixture was next concentrated to approximately 250 mL. After which 750 mL of DCM was added and the mixture was washed with 750 mL of 1:1 saturated aqueous $NaHCO_3$ solution/$H_2O$. The organic layer was then washed with 750 mL of brine, dried over $Na_2SO_4$, filtered, and concentrated under reduced pressure to afford approximately 72 g, or a 92% yield, of a compound of Formula III (rac-(2R,3R,6S,7aS)-4-benzyl-3-((tert-butyldiphenylsilyl)oxy) octahydro-1H-2,6-methanopyrrolo [3,2-b] pyridine) as a dark yellow/orange oil.

Figure 10:
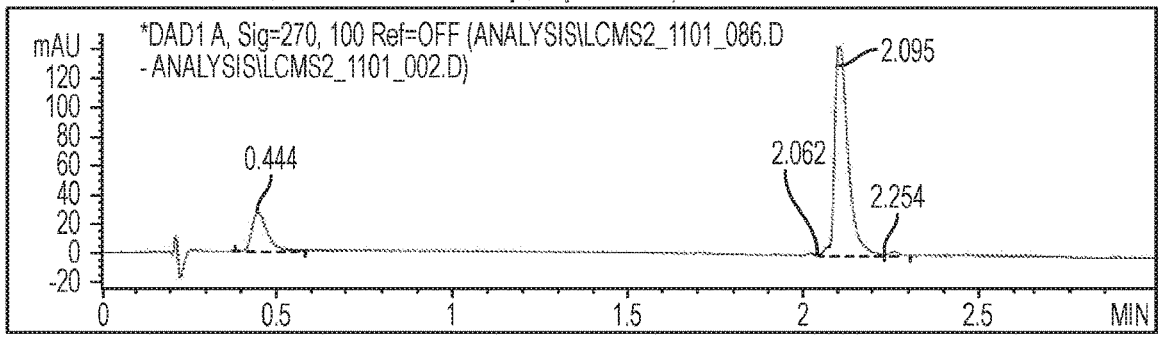
FIG. 10 shows the results of a LCMS analysis of the compound of Formula III.
Figure 10:
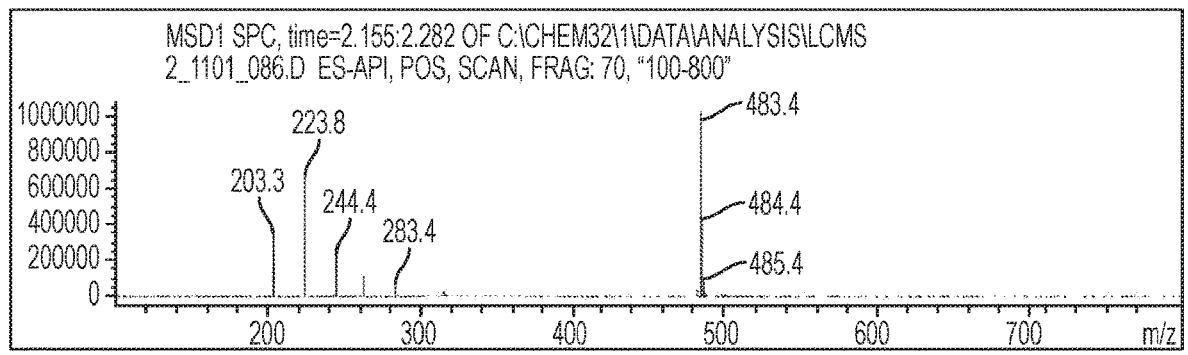
Figure 10:
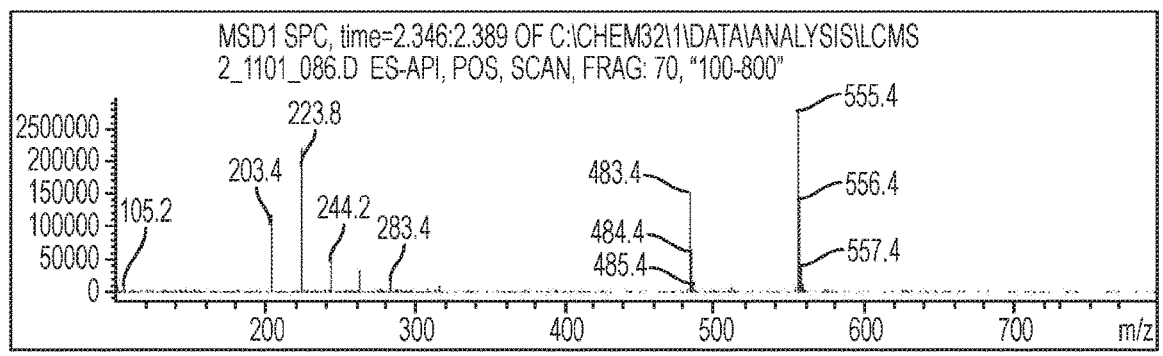

A sample was taken and analyzed by LCMS (FIG. 10) which showed the correct mass, and that the product had a purity of about 80%, with the peak at 0.448 being toluene. $^{1H}$NMR (400 MHz, Chloroform-d) δ 7.69-7.63 (m, 4H), 7.47-7.37 (m, 6H), 7.26-7.12 (m, 5H), 4.36 (s, 1H), 3.73-3.70 (m, 1H), 3.39 (d, J=13.7 Hz, 1H), 3.26 (d, J=7.6 Hz, 1H), 3.06 (s, 1H), 2.90 (d, J=13.7 Hz, 1H), 2.79-2.74 (m, 1H), 2.41 (bs, 1H), 1.90-1.80 (m, 4H), 1.67-1.64 (m, 1H), 1.11-0.99 (m, 10H).

The next step proceeded as illustrated in Scheme 11:

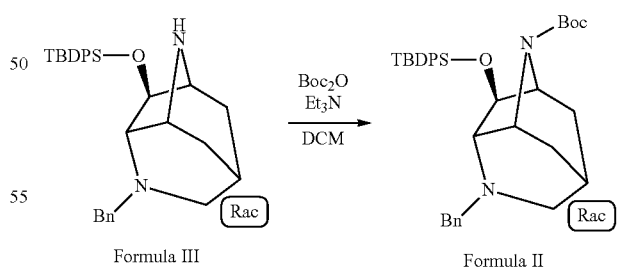

Formula III          Formula II $Et_3N$ (48.3 g, 477 mmol, 0.067 L) and di-tert-butyl dicarbonate ($Boc_2O$) (39.1 g, 179 mmol) was added to a solution of the compound of Formula III (72 g, 119 mmol, 80%) in 1 L of dichloromethane to form a light yellow solution which was stirred at room temperature over the weekend.

Figure 11A:
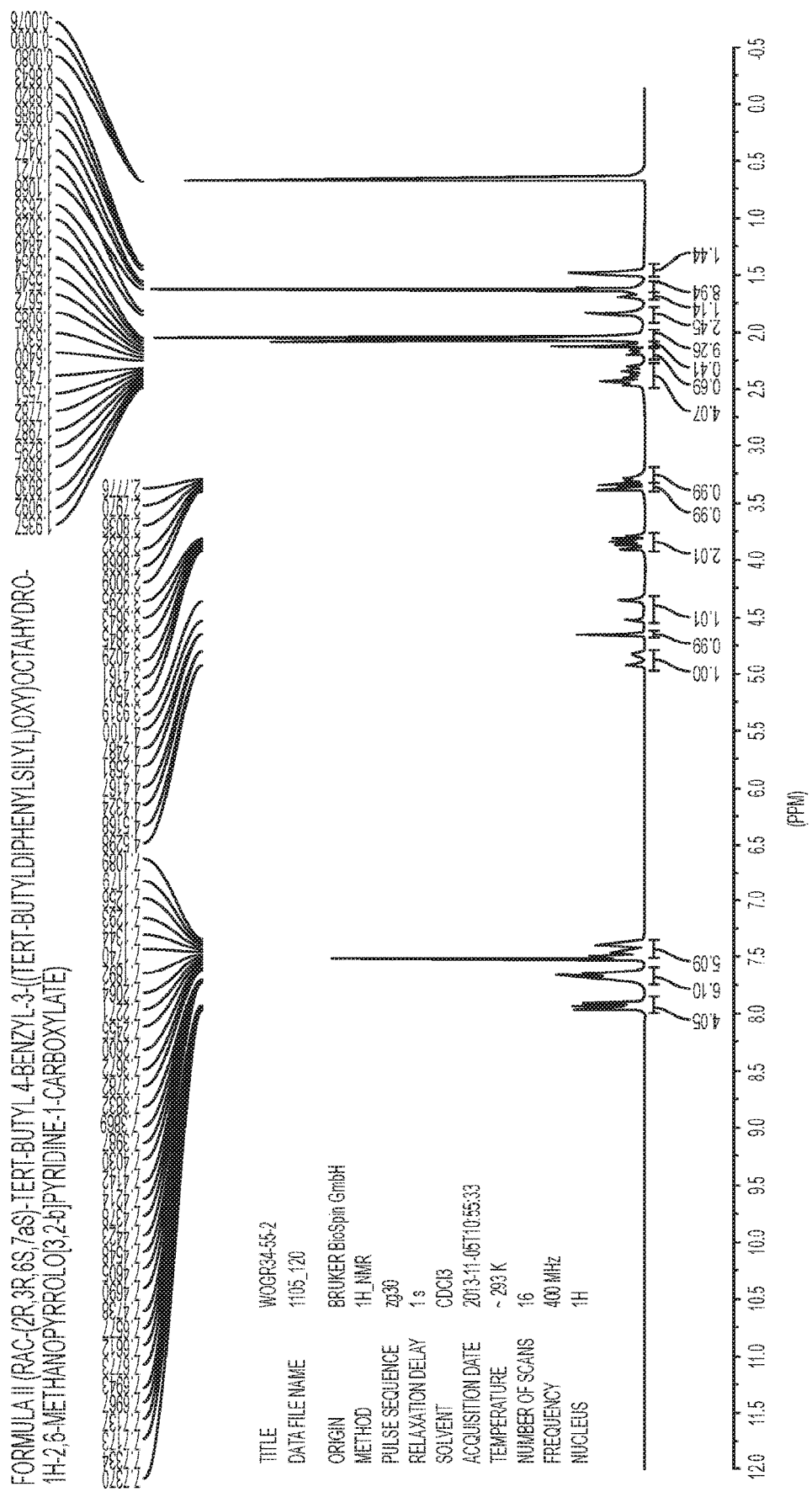
FIGS. 11A and 11B show the results of a structural analysis of the compound of Formula II.
Figure 11B:
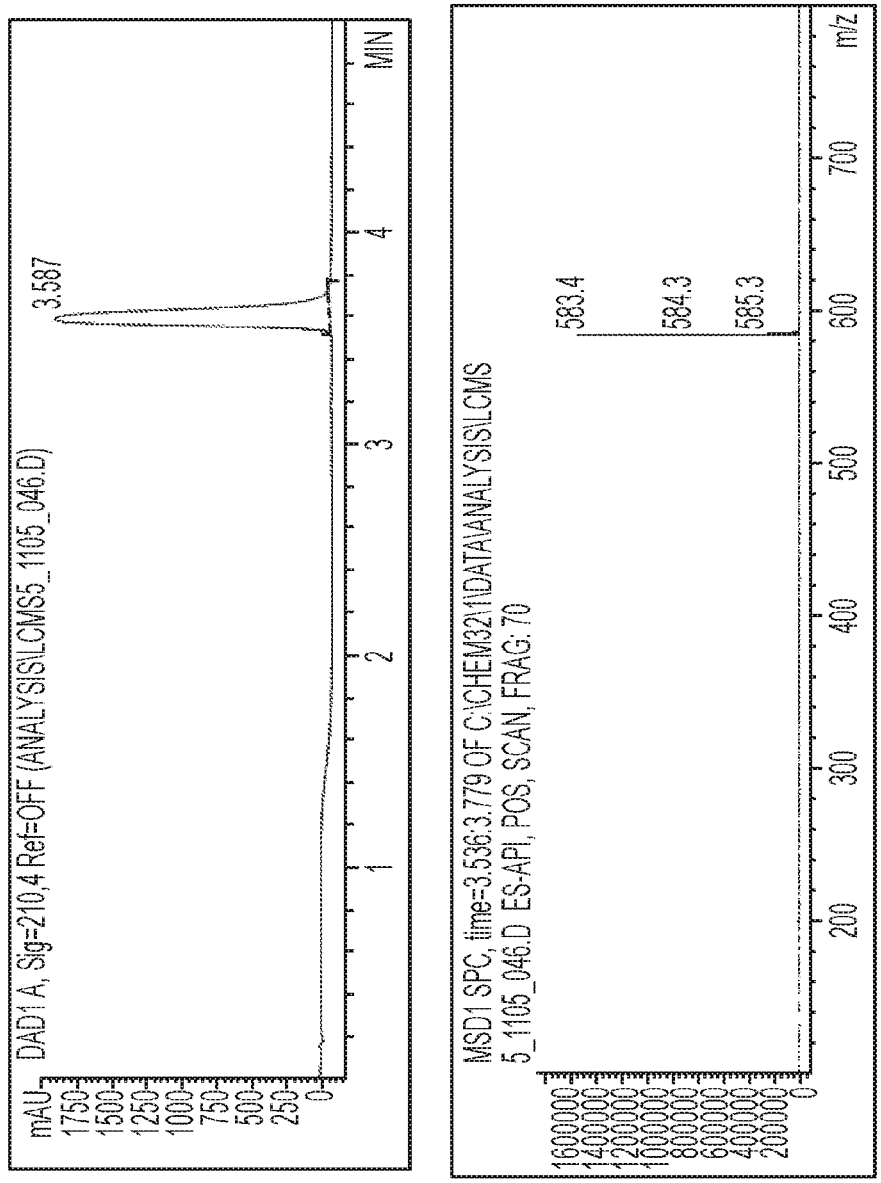

A sample taken and analyzed by TLC which showed the reaction was complete. The solution was diluted with 250 mL of DCM and washed with 1 L of saturated aqueous NaHCO$_3$ solution and 1 L of brine. The organic layer was then dried over Na$_2$SO$_4$, filtered, and concentrated to afford approximately 80 g of the crude product. Purification by gravity column chromatography (800 g, heptane/[EtOAc 1->10%]) afforded 68.4 g, or a 94% yield, of a compound of the Formula II (rac-(2R,3R,6S,7aS)-tert-butyl 4-benzyl-3-((tert-butyldiphenylsilyl)oxy)octahydro-1H-2, 6-methanopyrrolo[3,2-b]pyridine-1-carboxylate) as a colorless glass. A sample was taken and analyzed by $^{1H}$NMR (FIG. 11A) and LCMS (FIG. 11B) which showed agreement between the product and the structure of Formula II, and further showing that the product contained 4 w/w % heptane. $^{1H}$NMR (400 MHz, Chloroform-d) δ 7.73-7.65 (m, 4H), 7.47-7.35 (m, 6H), 7.24-7.10 (m, 5H), 4.53-4.40 (m, 1H), 4.24 (d, J=3.8 Hz, 1H), 4.10-3.92 (m, 1H), 3.44-3.32 (m, 2H), 2.87 (d, J=13.6 Hz, 1H), 2.33-2.77 (m, 1H), 1.93-1.72 (m, 4H), 1.65-1.54 (m, 1H), 1.50-1.47 (m, 9H), 1.10-1.02 (m, 10H).

Figure 12A:
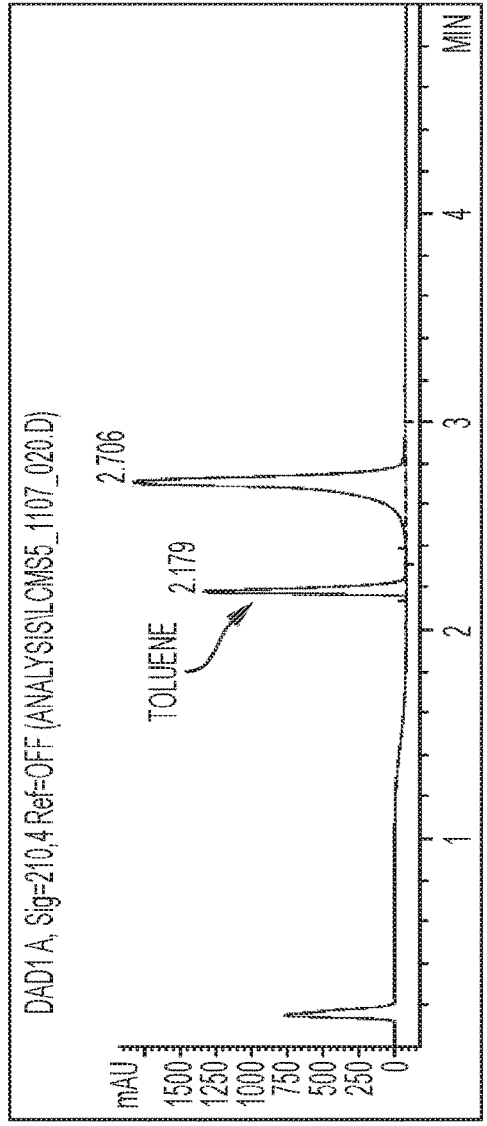
FIGS. 12A and 12B show the results of a structural analysis of the compound of Formula I.
Figure 12A:
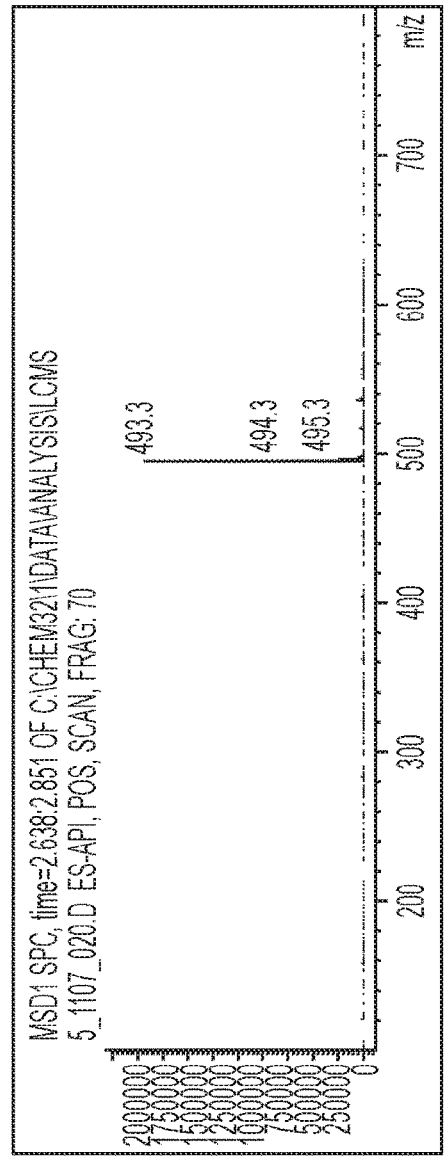
Figure 12B:
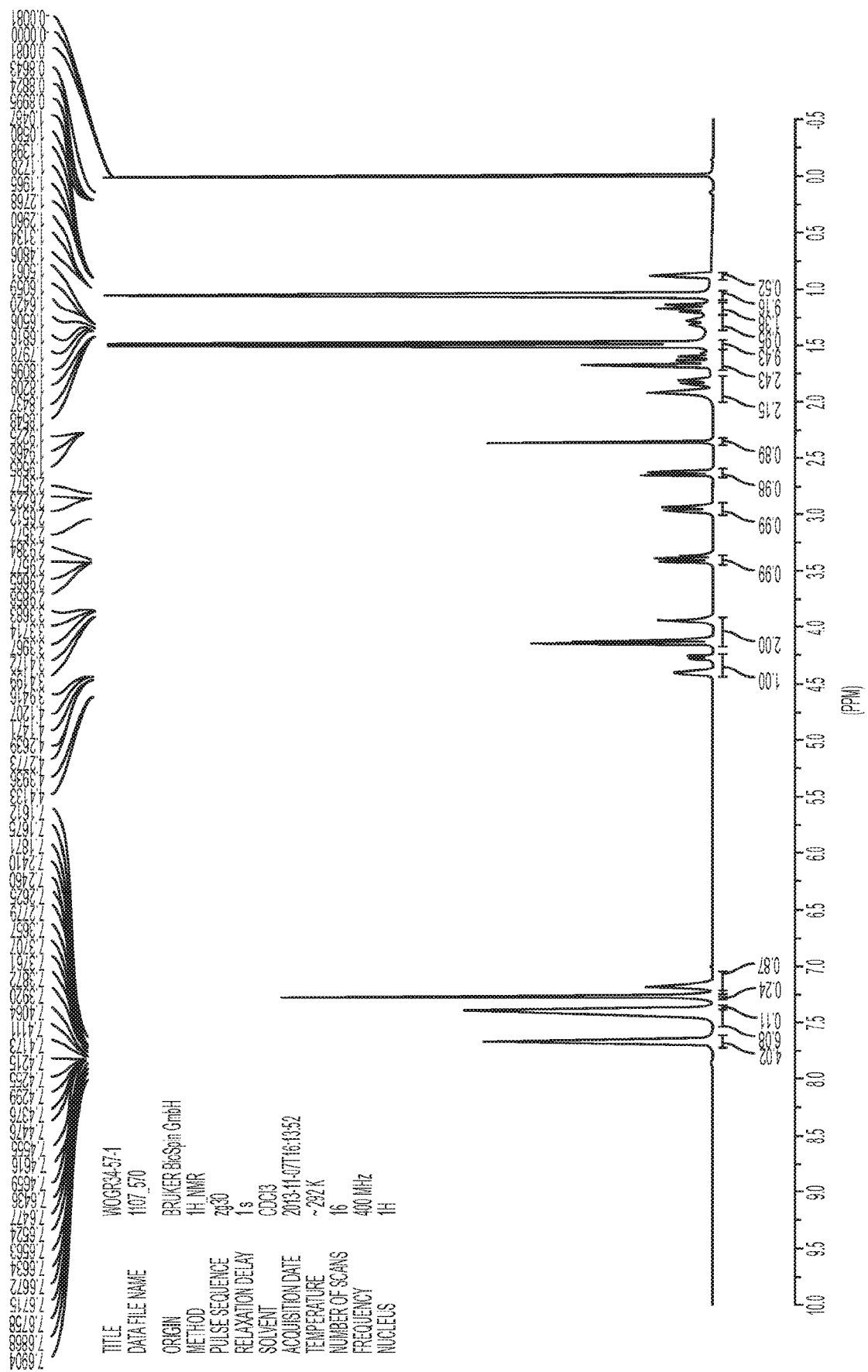

The next step proceeded as illustrated in Scheme 12:

1 L of brine, dried over Na$_2$SO$_4$, filtered, and concentrated under reduced pressure before being stripped again with pentane to afford 58.5 g of a thick tan syrup, a compound of Formula I (rac-(2R,3S,6S,7aS)-tert-butyl 3-((tert-butyldiphenylsilyl)oxy)octahydro-1H-2,6-methanopyrrolo [3,2-b] pyridine-1-carboxylate). A sample was taken and analyzed by $^{1H}$NMR (FIG. 12B) and LCMS (FIG. 12A) which showed the product was in agreement with structure of Formula I and contained 5.1 weight % of toluene and 1.3 weight % of n-pentane. $^{1H}$NMR (400 MHz, Chloroform-d) δ 7.68-7.63 (m, 4H), 7.45-7.35 (m, 6H), 4.40-4.25 (m, 1H), 4.13-3.93 (m, 2H), 3.41-3.36 (m, 1H), 2.97-2.92 (m, 1H), 2.62 (d, J=11.5 Hz, 1H), 1.96-1.78 (m, 2H), 1.67 (s, 1H), 1.64-1.56 (m, 1H), 1.49-1.47 (m, 9H), 1.16-1.13 (m, 1H), 1.05-1.04 (m, 9H).

The compound of Formula I was separated into its respective enantiomers via supercritical fluid chromatography (SFC) on a Welkho-1 column with 90/10 scCO$_2$/iPrOH+ 0.2% isopropylamine eluent as as illustrated in Scheme 13:

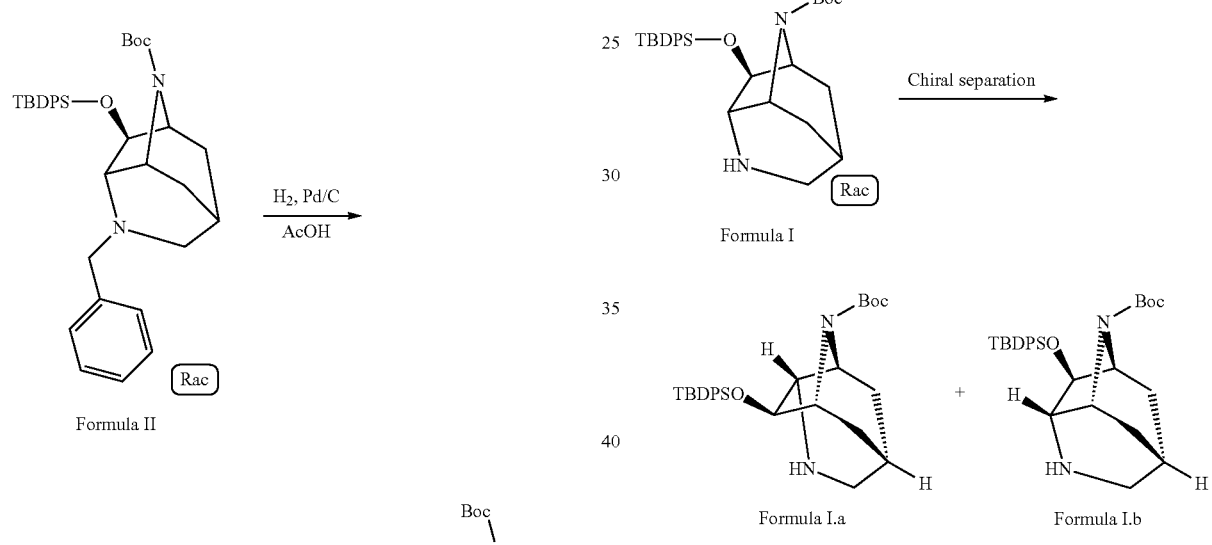

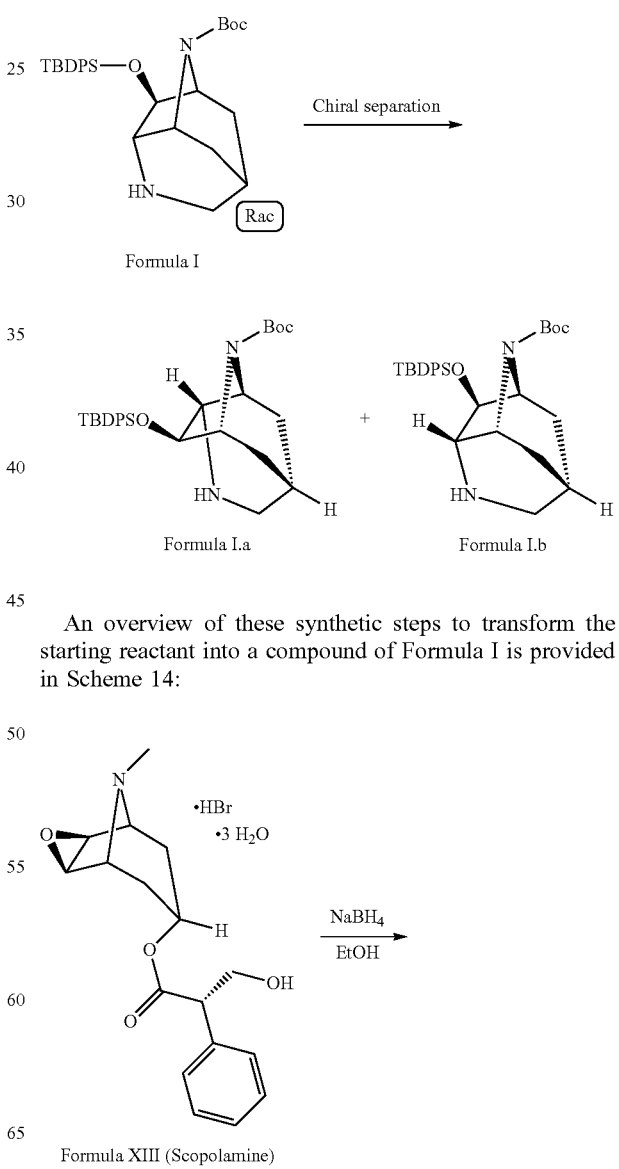

Under a nitrogen flow, Palladium, 10% on activated carbon (7 g, 125 mmol) was added to a solution of the compound of Formula II (72.9 g, 125 mmol) in 600 mL of acetic acid. The vessel was closed and the resulting mixture was stirred at 50° C. for 2 hours under a hydrogen atmosphere created by a balloon.

The mixture was then stirred at 50° C. overnight. The black suspension was filtered over EtOH rinsed celite and the filtrate was concentrated under reduced pressure. The residue was stripped twice with 0.5 L of toluene, after which it was dissolved in 1 L of diethyl ether. The organic layer was washed with 1 L of 10% (w/v) aqueous K$_2$CO$_3$ solution, An overview of these synthetic steps to transform the starting reactant into a compound of Formula I is provided in Scheme 14:

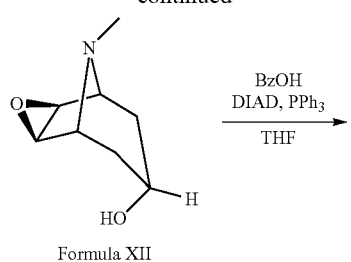
Formula XII
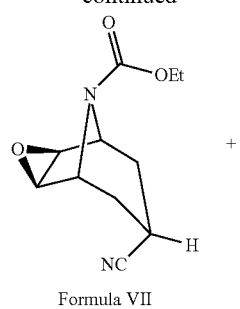
Formula VII
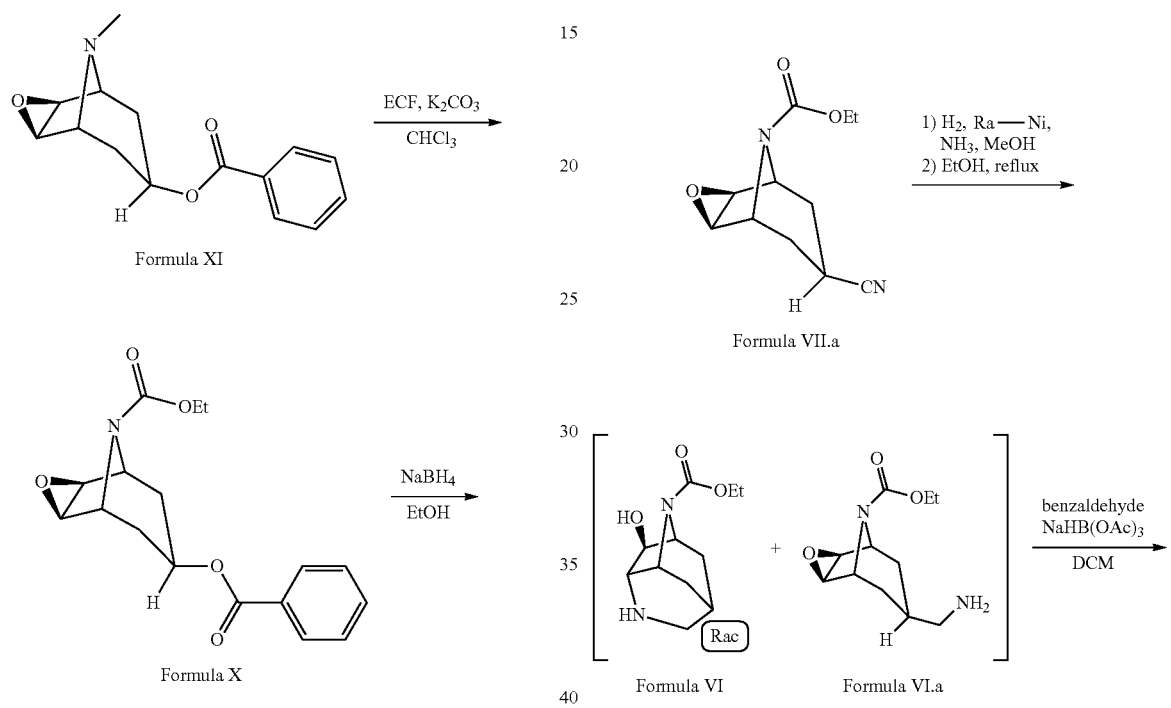
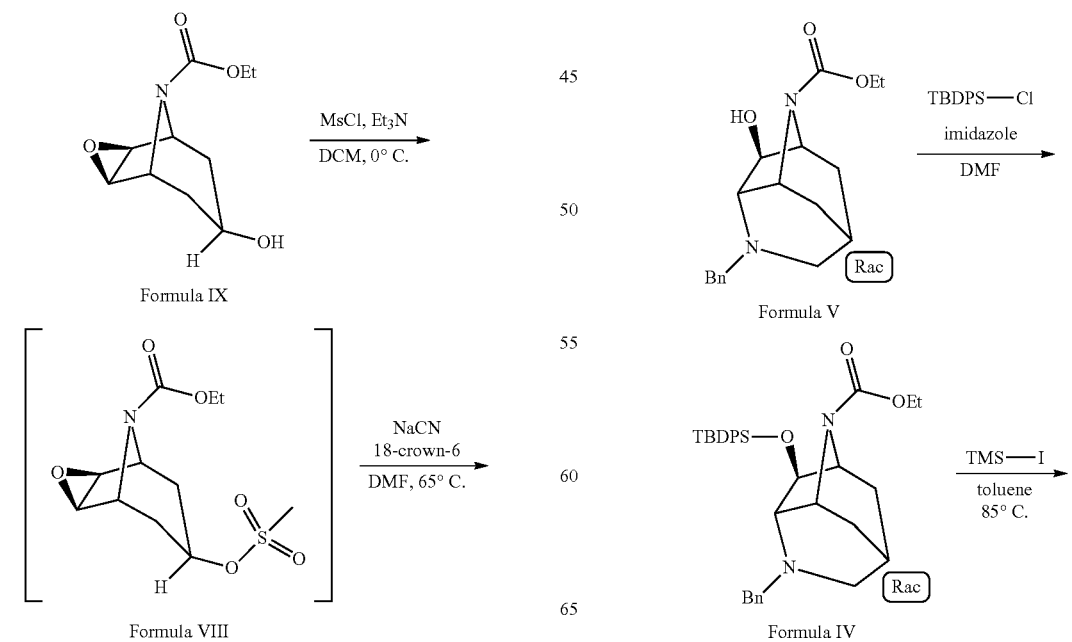

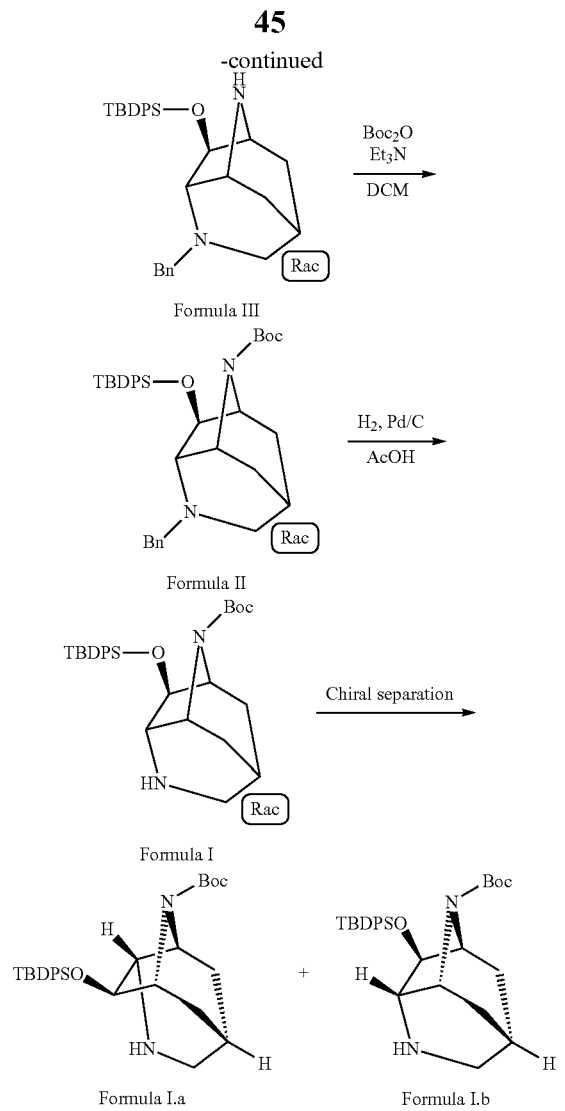

Example 2: Synthesis of a Therapeutic Derivative of a Compound of Formula I

The following describes steps for synthesizing a compound of Formula XVIII from a compound of Formula I.a.

As illustrated below in Scheme 15, first the compound of Formula XIV ((2R*,3R*,3aS*,6S*,7aS*)-tert-butyl 3-((tert-butyldiphenylsilyl)oxy)-4-(5-fluoropicolinoyl) octahydro-1H-2,6-methanopyrrolo[3,2-b]pyridine-1-carboxylate), was synthesized from the compound of Formula I.a.

Scheme 15

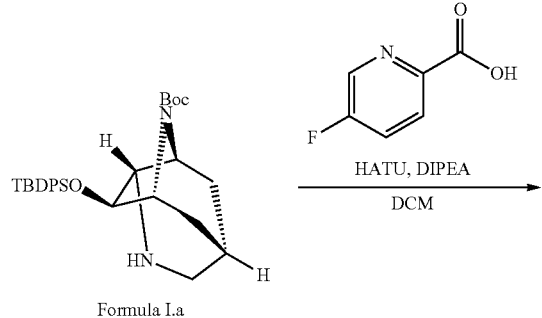

11.58 g (30.4 mmol) of 1-[Bis(dimethylamino)methylene]-1H-1,2,3-triazolo[4,5-b]pyridinium 3-oxid hexafluorophosphate (HATU) was added to a solution of 5-fluoropicolinic acid (4.30 g, 30.4 mmol) and diisopropylethylamine (DIPEA) (3.93 g, 30.4 mmol, 5.32 mL) in 125 mL of DCM. The reaction mixture was stirred then for 2 hours at room temperature. A solution of the compound of Formula I.a (12.5 g, 25.4 mmol) in 125 mL of DCM was added, and the reaction mixture was stirred overnight at room temperature.

Figure 13:
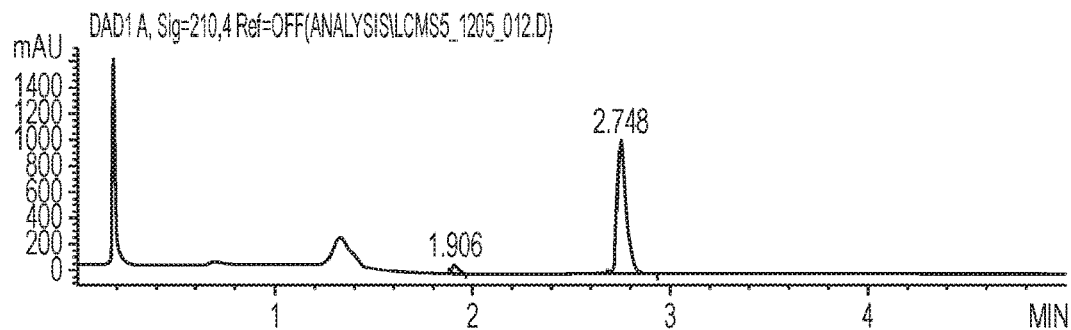
FIG. 13 shows the results of a LCMS analysis of the compound of Formula XIV.
Figure 13:
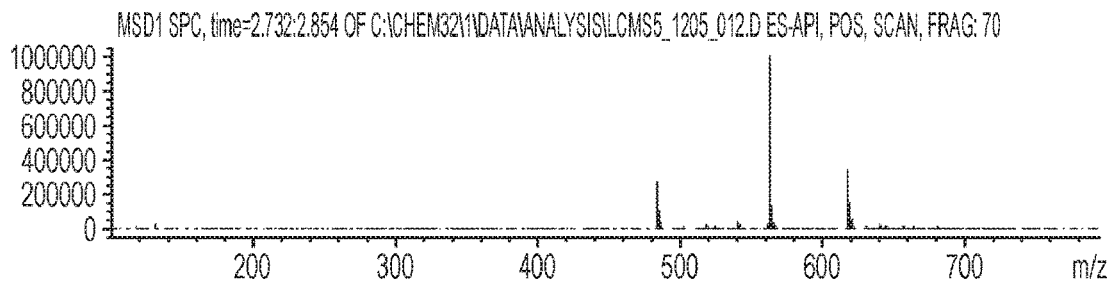

The reaction mixture was diluted with 200 mL of DCM, washed with aqueous saturated NaHCO$_3$ (300 mL), 1 M KHSO$_4$ (300 mL) and brine (400 mL). The organic layer was dried with sodium sulfate and concentrated to yield 22.0 g, (141%) of the compound of Formula XIV, as confirmed by LCMS (FIG. 13).

As illustrated below in Scheme 16, a compound of Formula XV ((2R*,3R*,3aS*,6S*,7aS*)-tert-butyl 4-(5-fluoropicolinoyl)-3-hydroxyoctahydro-1H-2,6-methanopyrrolo[3,2-b]pyridine-1-carboxylate) was then synthesized from the compound of Formula XIV.

Scheme 16

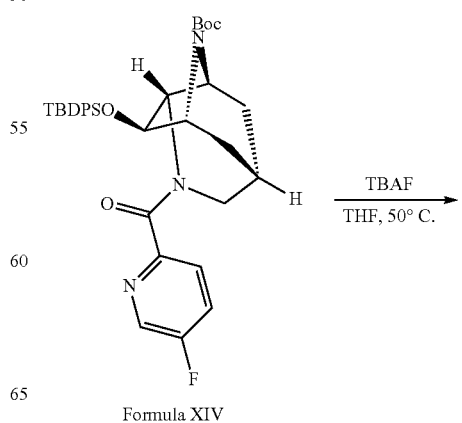

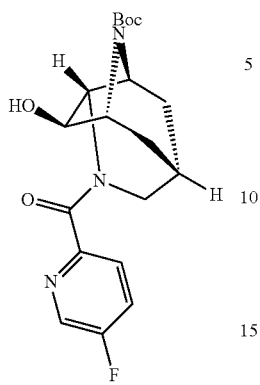

Formula XV

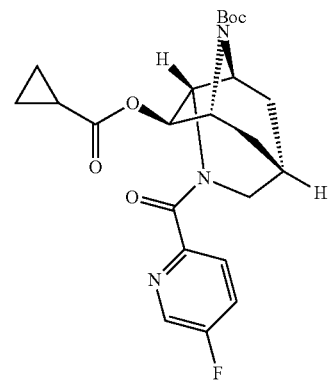

Formula XVI

Figure 14:
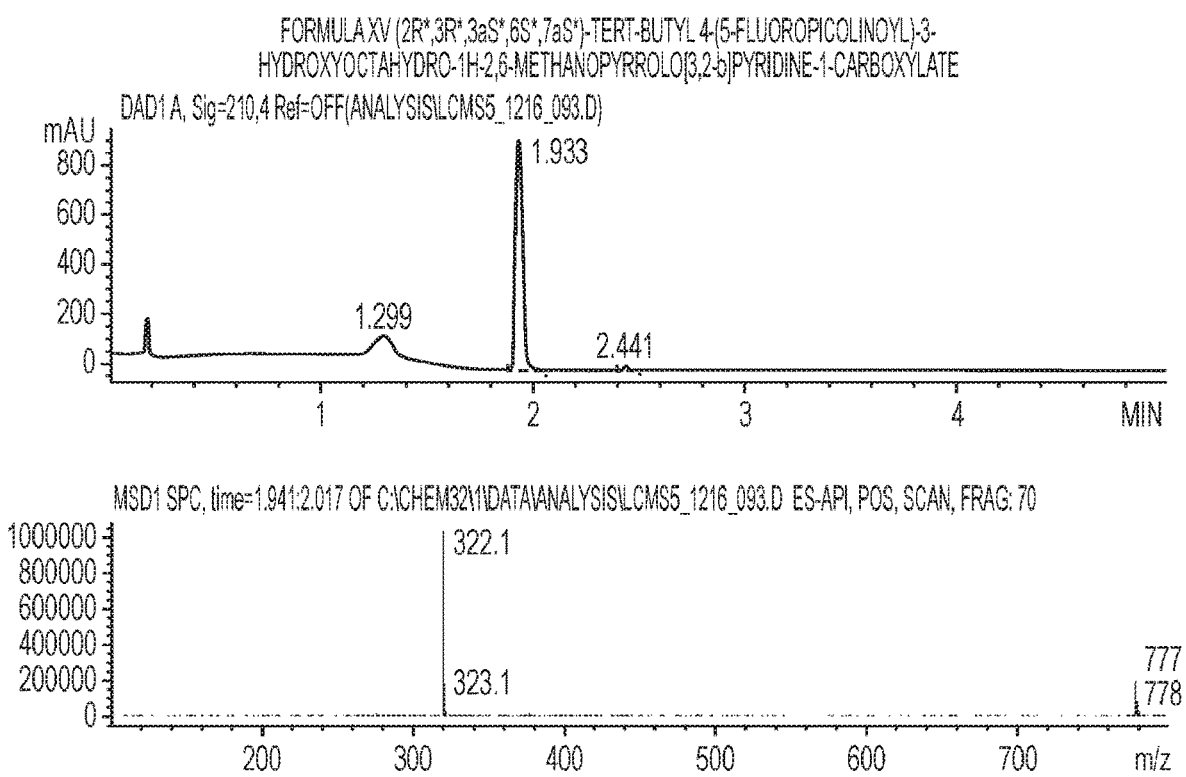
FIG. 14 shows the results of a LCMS analysis of the compound of Formula XV.

To a solution of the compound of Formula XIV (15.64 g, 25.4 mmol) in 100 mL of dry tetrahydrofuran was added 76 mL (76 mmol) tetrabutylammonium fluoride (TBAF) and the reaction mixture was stirred at 50° C. overnight. The reaction mixture was concentrated to dryness and purified by gravity column chromatography (500 mL silica, DCM to 5% MeOH/DCM) to yield 11.4 g of desired material, contaminated with side products. The residue was dissolved in 0.25 L of EtOAc and washed twice with 0.5 L of brine to yield 9.50 g (99%) of the compound of Formula XV, contaminated with an unidentified impurity, as indicated by LCMS Analysis (FIG. 14). The material was used as such in the next reaction.

As illustrated below in Scheme 17, a compound of Formula XVI ((2R*,3R*,3aS*,6S*,7aS*)-tert-butyl 3-((cyclopropanecarbonyl)oxy)-4-(5-fluoropicolinoyl)octahydro-1H-2,6-methanopyrrolo[3,2-b]pyridine-1-carboxylate) was then synthesized from the compound of Formula XV.

Figure 15:
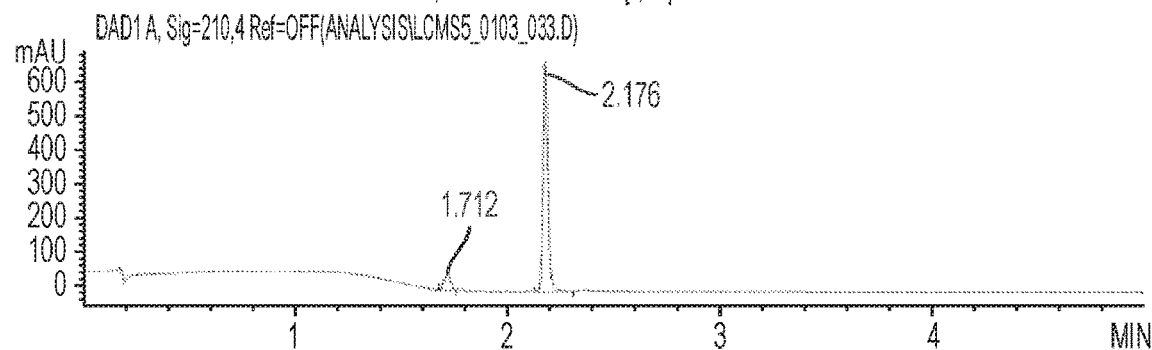
FIG. 15 shows the results of a LCMS analysis of the compound of Formula XVI.
Figure 15:
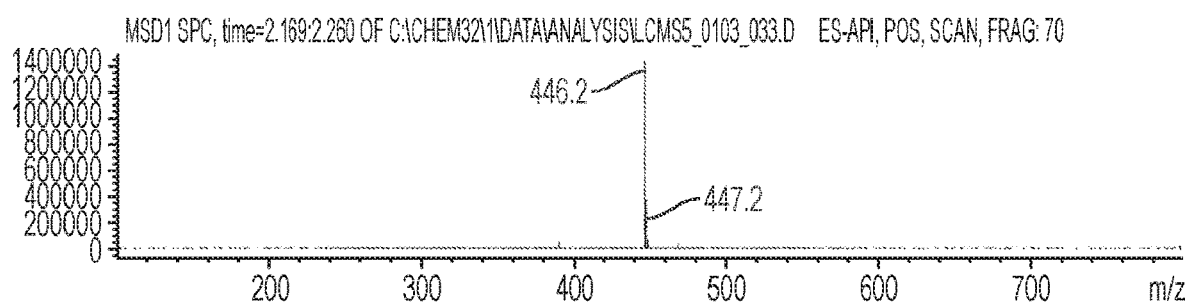

The compound of Formula XV (3.5 g, 9.27 mmol) was dissolved in 40 mL of pyridine, followed by the addition of 1.133 g (9.27 mmol) of 4-dimethylaminopyridine (DMAP) and 20.16 mL (23.18 mmol) of cyclopropanecarbonyl chloride. The reaction mixture was stirred at 60° C. for 3 hours. Afterwards, the reaction mixture was diluted with 250 mL of ethyl acetate and washed with KHSO$_4$ (0.5M, 200 mL), NaHCO$_3$. (sat., aq., 200 mL) and brine (200 mL). The organic phase was dried with sodium sulfate, filtered and the solvent evaporated. The crude residue was purified by gravity column chromatography (silica, 50% EtOAc/heptane to 100% EtOAc) to yield 3.40 g (82%) of the compound of Formula XVI, as confirmed by LCMS (FIG. 15).

As illustrated below in Scheme 18, a compound of Formula XVII ((2R*,3R*,3aS*,6S*,7aS*)-4-(5-fluoropicolinoyl)octahydro-1H-2,6-methanopyrrolo[3,2-b]pyridin-3-yl cyclopropanecarboxylate) was then synthesized from the compound of Formula XVI.

Scheme 17

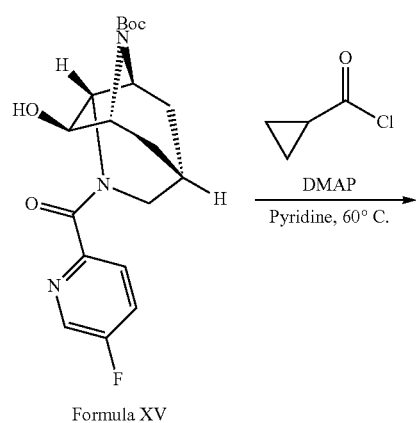

Formula XV

Scheme 18

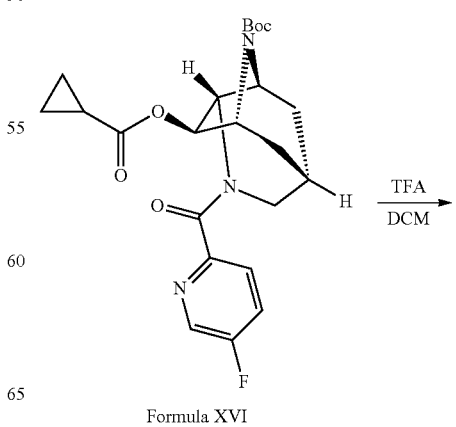

Formula XVI

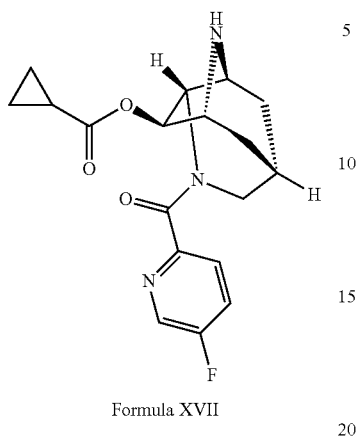

Formula XVII

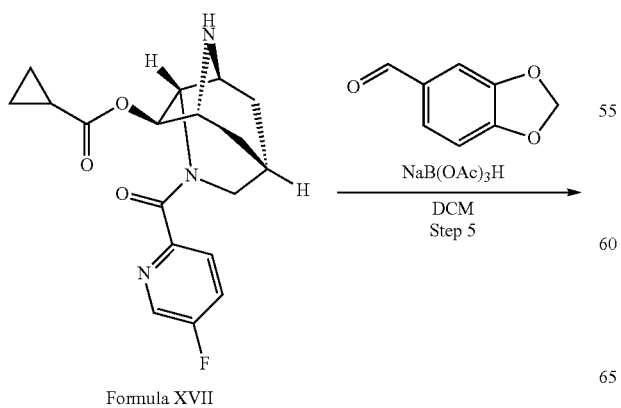

Formula XVIII

Figure 16:
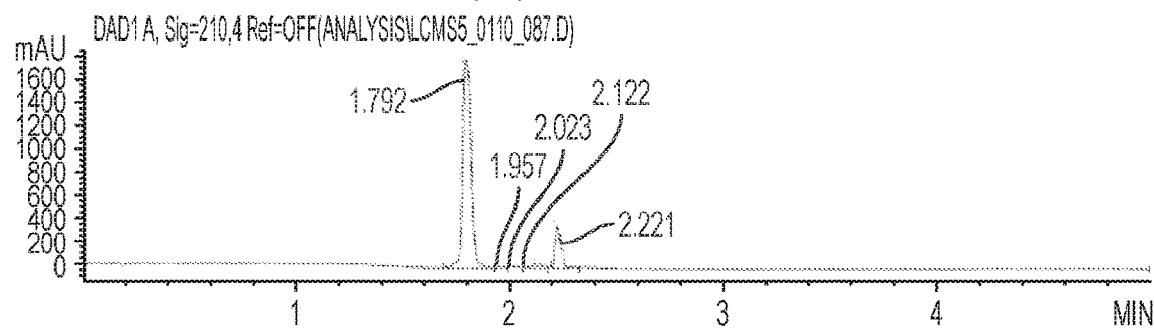
FIG. 16 shows the results of a LCMS analysis of the compound of Formula XVII.
Figure 16:
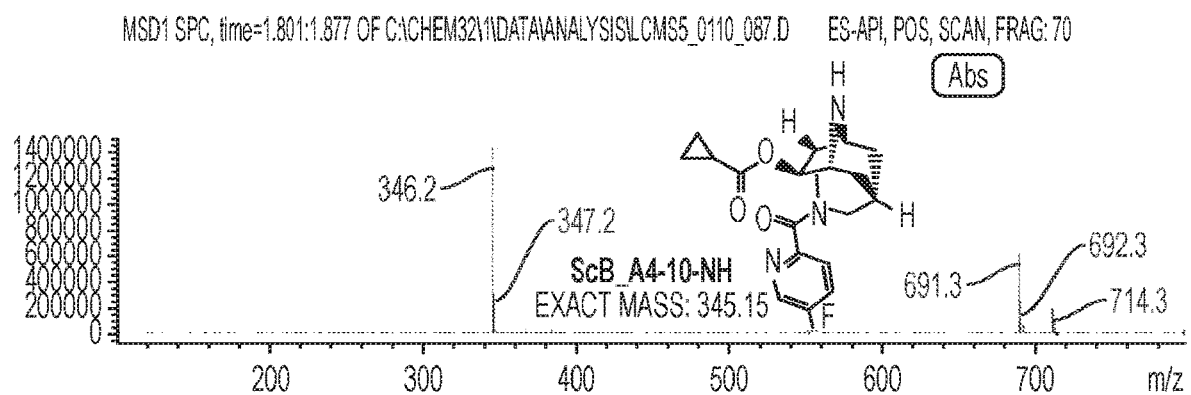

In a 250 mL round-bottomed flask, 3.40 g (7.63 mmol) of the compound of Formula XVI was dissolved in 30 mL of DCM. Trifluoroacetic acid (46.1 g, 404 mmol, 30 ml) was added and the reaction mixture was stirred at room temperature for 90 minutes. The reaction mixture was evaporated to dryness and co-evaporated twice with toluene. This residue was partitioned between 150 mL of $CHCl_3$ and 150 mL of saturated $Na_2CO_3$(aq), and the organic phase was separated. The aqueous layer was extracted twice with 100 mL of $CHCl_3$. The combined organic layers were washed with 100 mL of brine, dried over $Na_2SO_4$, filtrated, evaporated to dryness and co-evaporated with DCM once to yield 2.791 g (106%) of the compound of Formula XVII, as confirmed by LCMS analysis (FIG. 16)

As illustrated below in Scheme 19, a compound of Formula XVIII was synthesized from the compound of Formula XVII.

Figure 17A:
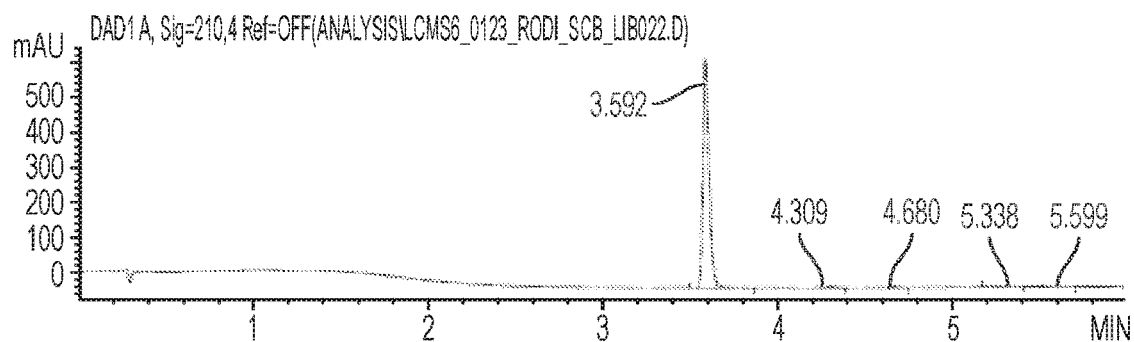
FIGS. 17A and 17B show the results of a structural analysis of the compound of Formula XVIII.
Figure 17A:
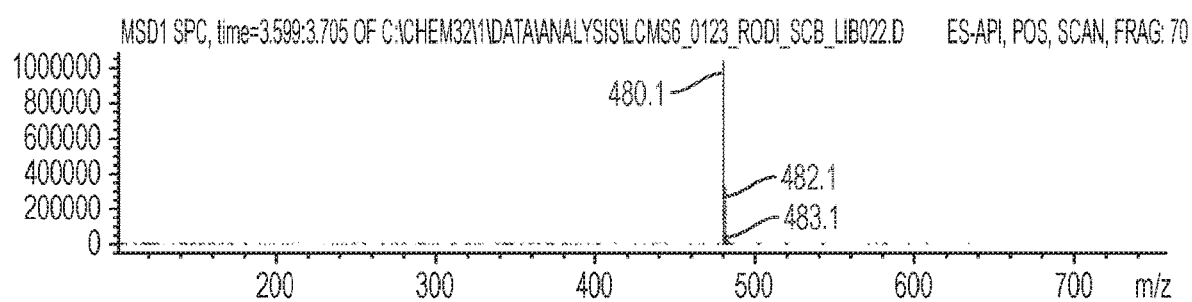
Figure 17B:
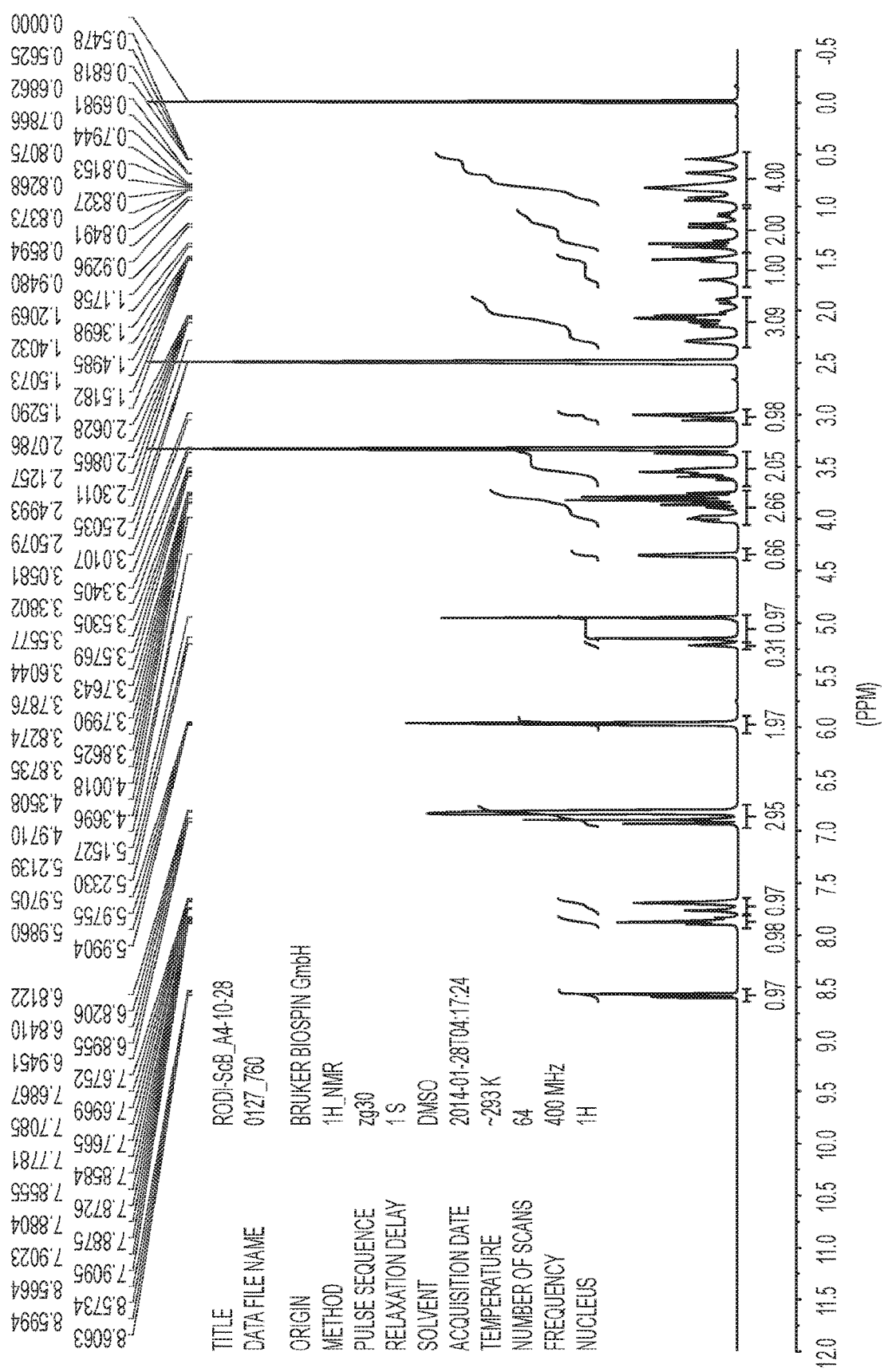

The compound of Formula XVII was dissolved in 2 mL of DCM, followed by the addition of piperonal (1.3 eq: 36.17 mg; 0.24 mmol). After stirring for 2 hours at room temperature, 64.80 mg (0.31 mmol) of STAB was added. The reaction mixture was stirred overnight at room temperature, evaporated to dryness, and purified by preparative HPLC to yield 68.4 mg (77%) of the compound of Formula XVIII, as confirmed by LCMS (FIG. 17A) and $^{1H}$NMR (FIG. 17B).

Example 3: Synthesis of a Second Therapeutic Derivative of a Compound of Formula I The following describes steps for synthesizing a compound of Formula XXII from a compound of Formula I.b.

As illustrated below bin Scheme 20, first the compound of Formula XIX ((2S*,3S*,6R*,7aR*)-tert-butyl 3-((tert-butyldiphenylsilyl)oxy)-4-(2-methoxyacetyl)octahydro-1H-2, 6-methanopyrrolo[3,2-b]pyridine-1-carboxylate) was synthesized from the compound of Formula I.b.

Scheme 19

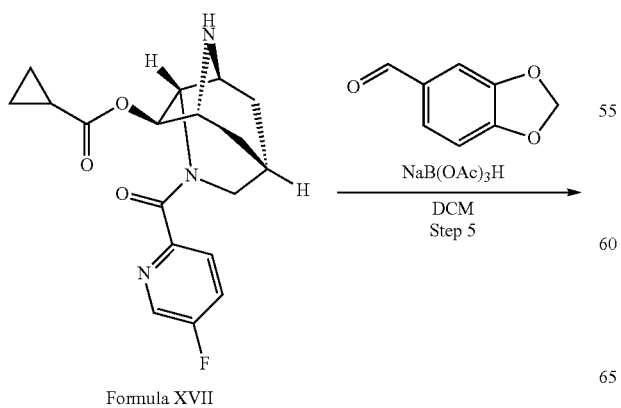

Formula XVII

Scheme 20

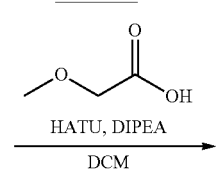

Formula I.b

-continued

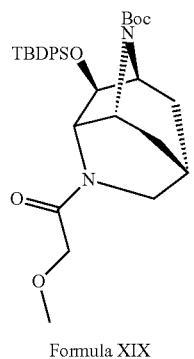

Formula XIX 3.17 g (35.2 mmol, 2.70 mL) of 2-methoxyacetic acid was dissolved in 124 mL of DCM and 4.55 g (35.2 mmol, 6.14 mL) of DIPEA. Then 13.40 g (35.2 mmol) of HATU was added and the mixture was stirred at ambient temperature for 2 hours. A solution of 12.4 g (25.2 mmol) of the compound of Formula I.b in 125 mL of DCM was added and stirred at ambient temperature overnight.

Figure 18:
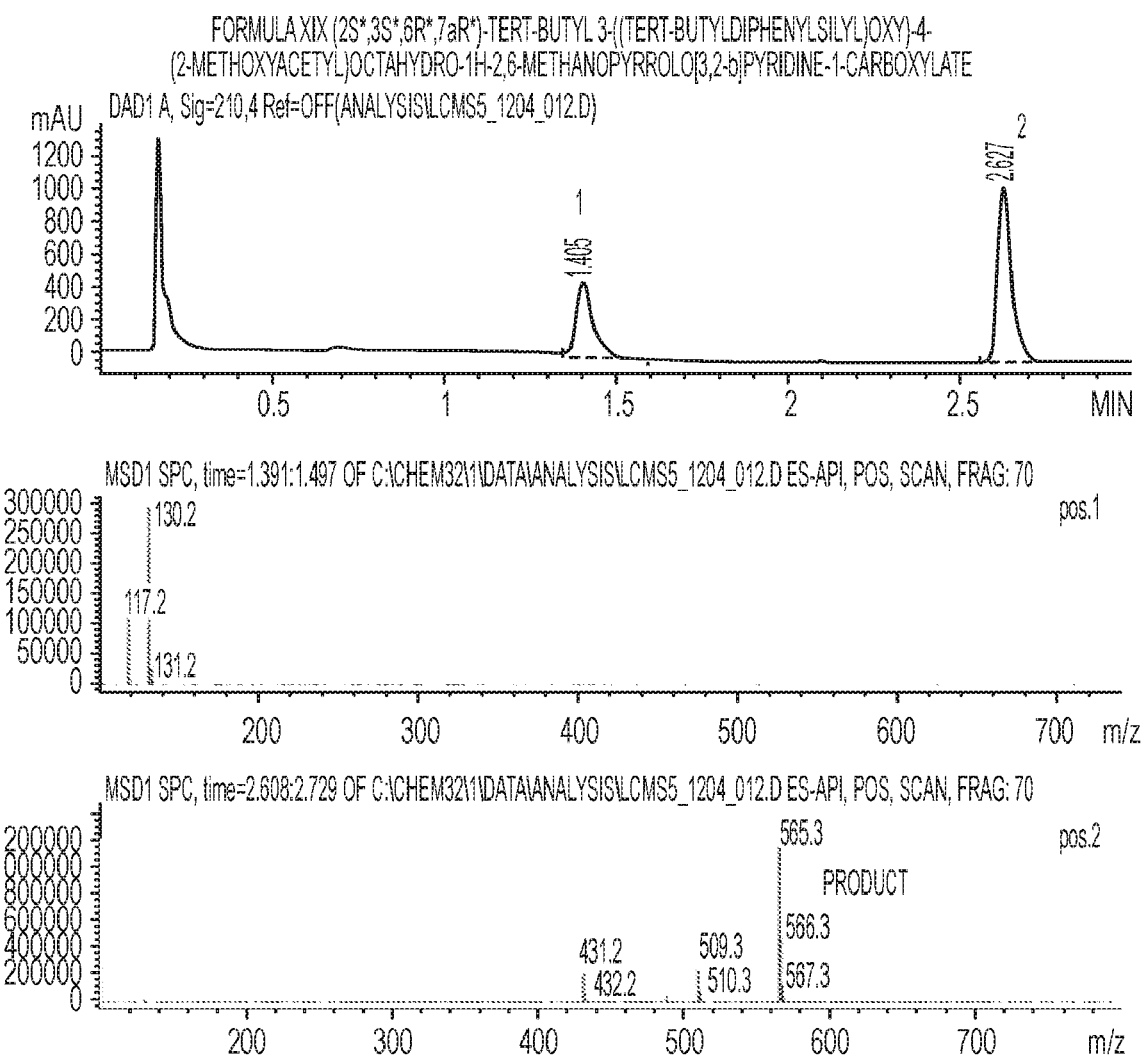
FIG. 18 shows the results of a LCMS analysis of the compound of Formula XIX.

The reaction mixture was washed with aqueous saturated NaHCO$_3$ (200 mL), 1M aqueous KHSO$_4$ (200 mL), water (200 mL) and brine (200 mL), the organic phase was dried with Na$_2$SO$_4$, filtered and the solvent evaporated to yield 23.40 g of the crude product, the compound of formula XIX. HPLC/MS analysis (FIG. 18) indicates that the desired material was contaminated with residual DIPEA.

As illustrated below in Scheme 21, a compound of Formula XX ((2S*,3S*,3aS*,6R*,7aR*)-tert-butyl 3-hydroxy-4-(2-methoxyacetyl)octahydro-1H-2,6-methanopyrrolo[3,2-b]pyridine-1-carboxylate) was then synthesized from the compound of Formula XIX.

Scheme 21

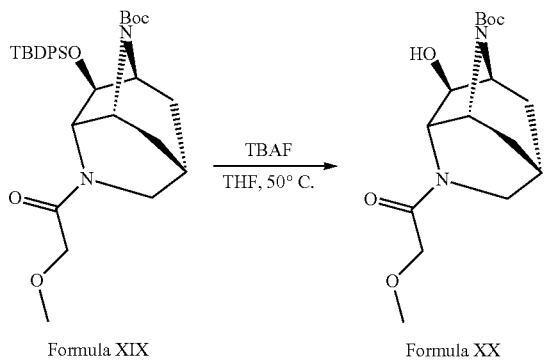

Formula XIX          Formula XX

Figure 19:
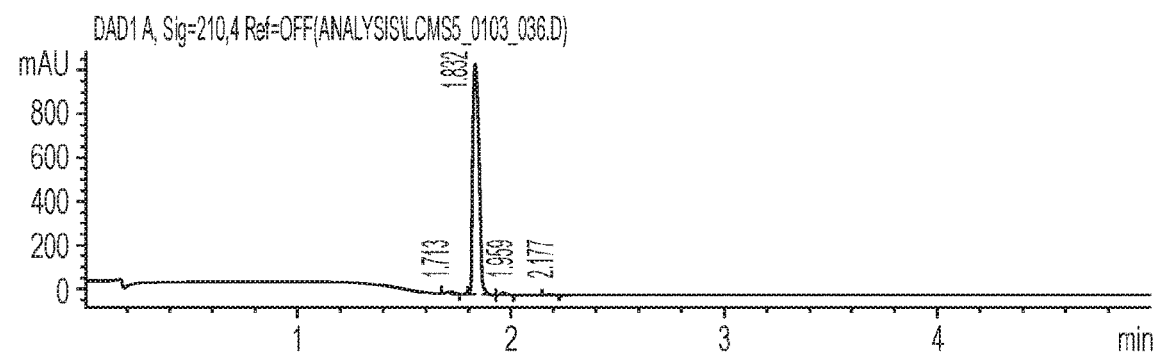
FIG. 19 shows the results of a LCMS analysis of the compound of Formula XX.
Figure 19:
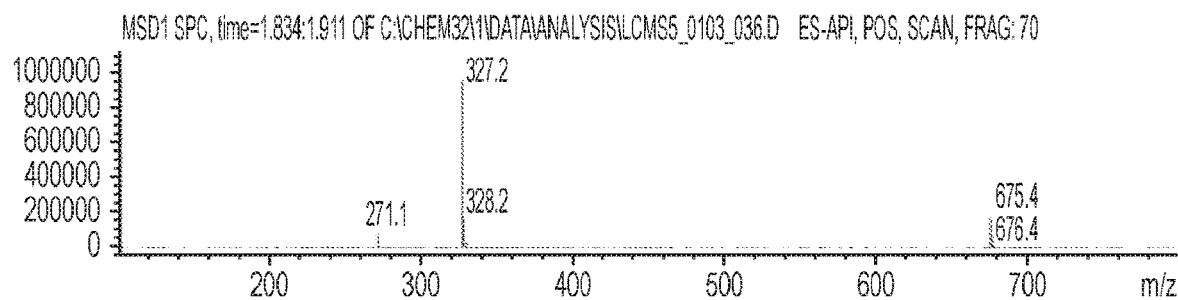

To a solution of the compound of Formula XIX (14.23 g, 25.2 mmol) in 100 mL of dry tetrahydrofuran (THF), at ambient temperature, a 1.0 M solution of tetrabutylammonium fluoride (TBAF) in THF (76 mmol, 76 mL) was added to the solution. The reaction mixture was then heated to 50° C. and stirred overnight. The crude reaction mixture was concentrated to dryness, and stripped twice with a 1:1 solution of ethylacetate/heptane to yield 23.40 g of the crude material. Purification by gravity column chromatography 50~100% ethylacetate in heptane yielded 8.21 g (quantitatively) of the compound of formula XX, as confirmed by LCMS analysis (FIG. 19).

As illustrated below in Scheme 22, a compound of Formula XXI (1-((2S*,3S*,3aS*,6R*,7aR*)-3-hydroxy-hexahydro-1H-2,6-methanopyrrolo[3,2-b]pyridin-4(2H)-yl)-2-methoxyethanone) was then synthesized from the compound of Formula XX.

Scheme 22

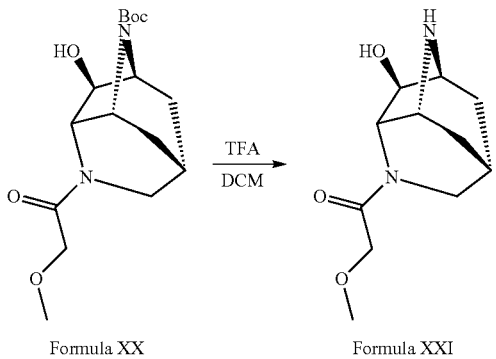

Formula XX          Formula XXI

To a solution of the compound of Formula XX (1.89 g, 5.79 mmol) in 35 mL of DCM was added to 51.8 g (454 mmol, 35 mL) trifluoroacetic acid (TFA) and the reaction mixture was stirred at room temperature for 1.5 hours. The reaction mixture was evaporated to dryness under reduced pressure and coevaporated twice with toluene. The resulting sticky oil was dissolved in 35 mL of chloroform and washed with aqueous saturated Na$_2$CO$_3$. Attempts to isolate the desired material in the organic phase were not successful. The aqueous phase was then evaporated to dryness under reduced pressure.

Figure 20:
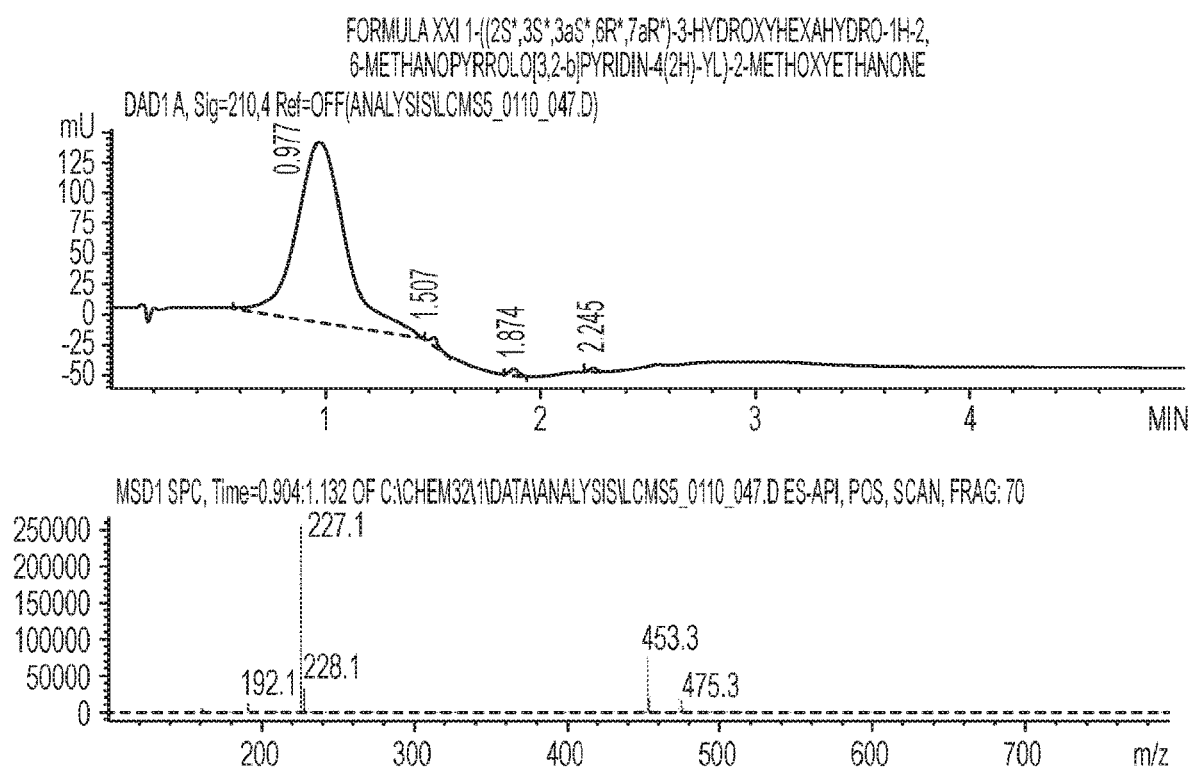
FIG. 20 shows the results of a LCMS analysis of the compound of Formula XXI.

To the solid was added a 9:1 mixture of chloroform/MeOH and the suspension was stirred overnight at room temperature. After filtration, the filtrate was evaporated to dryness under reduced pressure. The resulting solid was dissolved in chloroform, filtered (using a 40 micron LCMS filter) and evaporated to dryness under reduced pressure to afford 0.91 g, or 69.5% yield, of the compound of Formula XXI as a white foam, which was confirmed by LCMS (FIG. 20). The product was then used as such in the next reaction.

As illustrated in Scheme 23, a compound of Formula XXII (3-(((2S*,3S*,6R*,7aR*)-3-hydroxy-4-(2-methoxyacetyl)octahydro-1H-2,6-methanopyrrolo[3,2-b]pyridin-1-yl)methyl)benzamide) was synthesized from the compound of Formula XXI.

Scheme 23

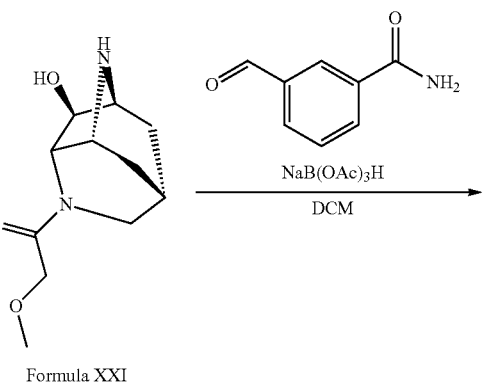

Formula XXI

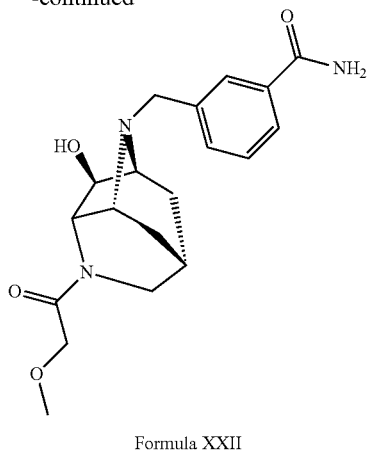

Formula XXII

Figure 21A:
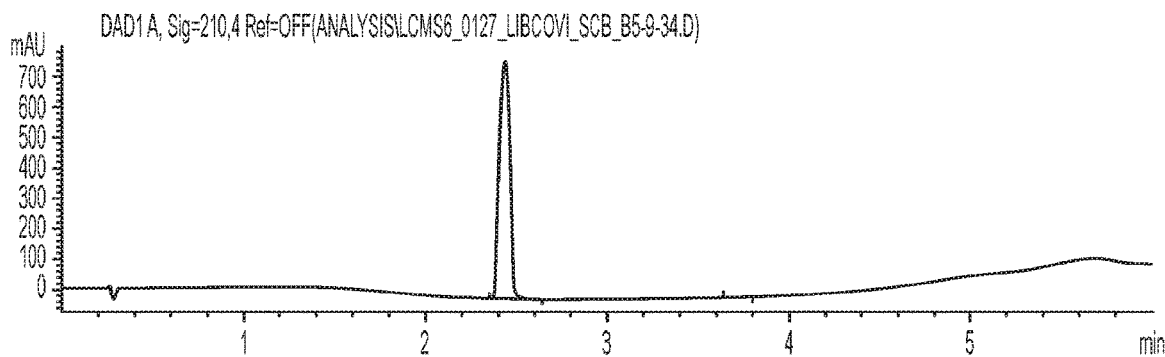
FIGS. 21A and 21B show the results of a structural analysis of the compound of Formula XXII.
Figure 21A:
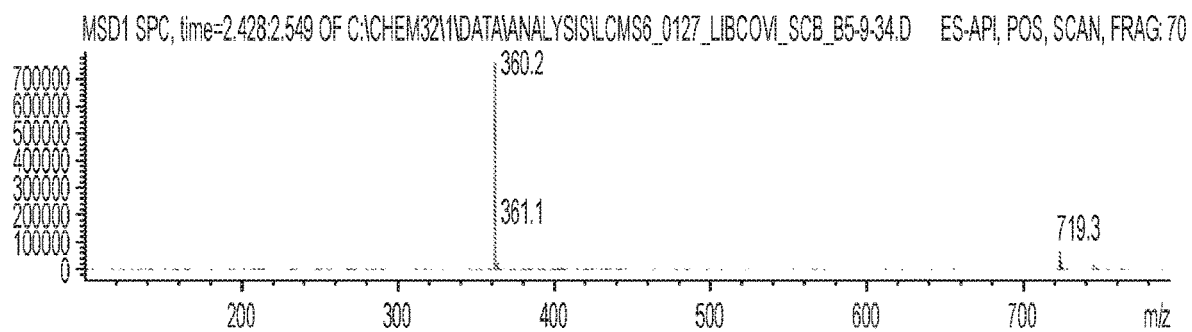
Figure 21B:
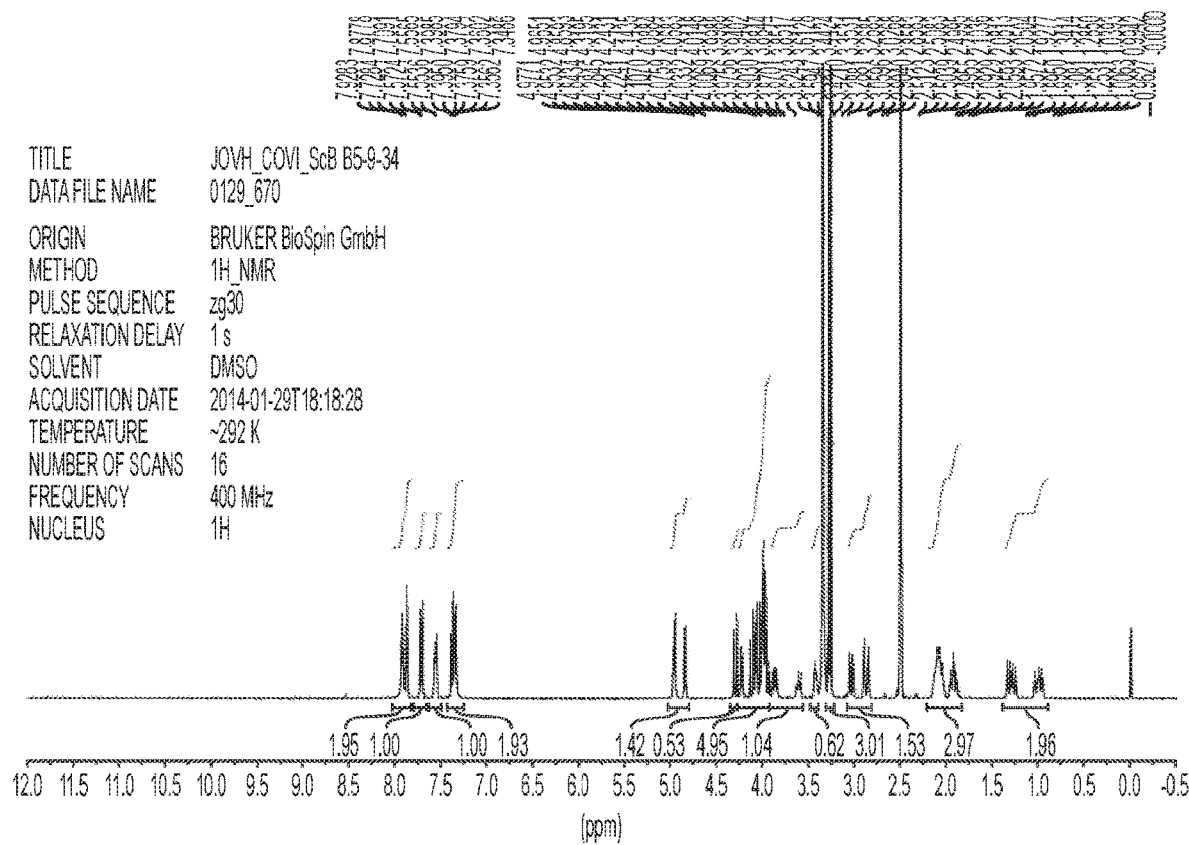

To a solution of the compound of Formula XXI (193 mg; 0.85 mmol) in 2 mL of DCM was added 165.4 mg (1.11 mmol) of 3-formyl benzamide and the reaction mixture was stirred overnight. Next, to the reaction mixture was added 298.3 mg (1.141 mmol) sodium triacetoxyborohydride and the reaction mixture was stirred at room temperature overnight. The reaction mixture was evaporated to dryness under reduced pressure using a Genevac. Purification by prep LCMS followed by evaporation of the solvents under reduced pressure (Genevac) afforded 244 mg, a 79.6% yield, of the desired product, the compound of Formula XXII, as confirmed by LCMS (FIG. 21A) and $^{1H}$NMR (FIG. 21B).

Example 4: Therapeutic Evaluation of Compounds of Formula XVIII and XXII

Intra plantar injection of 1% β-carrageenan may be used to induce local inflammation to the paws of test subject mice. In general, local inflammation is expressed as paw swelling and increased sensitivity to heat stimuli. Therefore, the effect of a test item on changes in heat hypersensitivity can be assessed. Using the protocol set forth, the therapeutic effect of the compounds of Formula XVIII and XXII were evaluated.

Animals were dosed with a test compound at time zero (control where given vehicle only) at 10 mg/kg ip (test item was dissolved in a 20% λ-hydroxypropyl cyclodextrin solution). After 30 minutes the animals were slightly anesthetized with isoflurane, and 0.1 ml of a 1% λ-carrageenan suspension in Distilled Water was injected into the plantar side of the right hind paws of the mice. After 3.5 hours after the λ-carrageenan administration, the animals were placed on a hotplate apparatus maintained at 57° C., and the time until the first response was recorded.

When the compound of Formula XVIII and the compound Formula XXII were tested as described above (n=5 animals), the average response time exceeded the pretreatment baseline response time as shown below.

In contrast, vehicle-treated animals displayed reduced response times over pre-treatment.

|  | Animal # | Pretreatment response time at (−24 h) (in sec) | Response time at 3.5 h (in sec) |
| --- | --- | --- | --- |
| Vehicle 20% CD | 1 | 9 | 3 |
|  | 2 | 7 | 4 |
|  | 3 | 8 | 4 |
|  | 4 | 7 | 6 |
|  | 5 | 10 | 5 |
|  | avg | 8.2 | 4.4 |
| Compound of Formula XXII | 1 | 6 | 12 |
|  | 2 | 8 | 14 |
|  | 3 | 8 | 13 |
|  | 4 | 6 | 10 |
|  | 5 | 9 | 12 |
|  | avg | 7.4 | 12.2 |
| Compound of Formula XVIII | 1 | 7 | 16 |
|  | 2 | 9 | 14 |
|  | 3 | 8 | 16 |
|  | 4 | 9 | 12 |
|  | 5 | 7 | 15 |
|  | avg | 8 | 14.6 |

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

It should be understood that although the compounds of Formulas II-XXIII may be drawn with specific chirality for the sake of simplicity, one skilled in the art would recognize how to create and separate these various isomers. Accordingly, all isomers of the compounds of Formulas II-XXIII may be understood to be within the scope of the present application.

What is claimed is:

1. A compound of Formula XXIII(A):

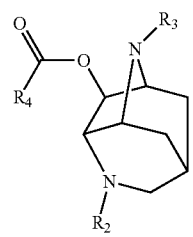

wherein $R_2$ is selected from the group consisting of hydrogen, C(O)R' wherein R' is $CH_2OCH_3$, or pyridine optionally substituted with halo;

wherein $R_3$ is selected from the group consisting of hydrogen, BOC, optionally substituted phenyl, or methylbenzodioxole; and wherein $R_4$ is hydrogen, alkyl, or cycloalkyl, or a stereoisomer, pharmaceutically acceptable salt, or mixture thereof.

2. The compound of claim 1, wherein $R_4$ is $C_3$cycloalkyl.

3. A compound of Formula XXIII(B):

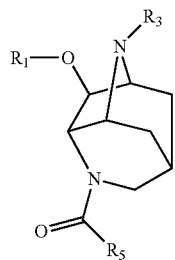

wherein R$_1$ is selected from the group consisting of hydrogen, benzyl, tert-butyldiphenylsilyl, or C=OR$_4$, wherein R$_4$ is alkyl;

wherein R$_3$ is selected from the group consisting of hydrogen, BOC, phenyl substituted with CON(R')$_2$ wherein R' is H, or; and wherein R$_5$ is hydrogen, alkyl, alkyl substituted with OCH$_3$, optionally substituted pyridine, or a stereoisomer, pharmaceutically acceptable salt, or mixture, thereof.

4. The compound of claim 3, wherein R$_5$ is CH$_2$OCH$_3$ or pyridine substituted with F.

5. The compound of claim 3, having the Formula XXIII (C):

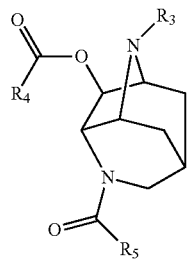

wherein R$_4$ is alkyl or cycloalkyl, or a stereoisomer, pharmaceutically acceptable salt, or mixture thereof.

6. The compound of claim 5, wherein R$_4$ is C$_3$cyloalkyl.

7. The compound of claim 5, having the Formula XXIII (E):

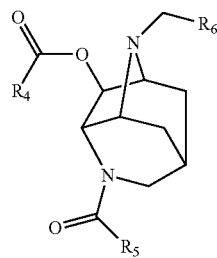

wherein R$_6$ is methylbenzodioxole, or phenyl substituted with CON(R')$_2$ wherein R' is H or a stereoisomer, pharmaceutically acceptable salt, or mixture thereof.

8. The compound of claim 7, wherein R$_6$ is methylbenzodioxole.

9. A compound of Formula XXIII(D):

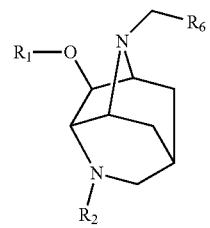

wherein R$_1$ is hydrogen, C=Oalkyl, or C=O cycloalkyl;
wherein R$_2$ is C=O optionally substituted pyridine or COCH$_2$OCH$_3$; and
wherein R$_6$ is phenyl substituted with CON(R')$_2$ wherein R' is H, methylbenzodioxole, azacyclic, pharmaceutically acceptable salt, or mixture thereof.

10. The compound of claim 9, wherein R$_6$ is methylbenzodioxol, or phenyl substituted with CON(R')$_2$ wherein R' is H.

11. A pharmaceutical composition comprising a compound of claim 1, and a pharmaceutically acceptable carrier or diluent.

12. A method for treating pain in a subject, comprising administering to the subject an effective amount of the compound of claim 1.

13. The method of claim 12, wherein the compound is administered to effect localized delivery to the subject.

14. The method of claim 12, wherein the compound is administered to effect systemic delivery to the subject.

15. The method of claim 12, wherein the pain is chronic pain.

16. The method of claim 12, wherein the pain is neuropathic pain.

17. A compound having the

Formula XIV

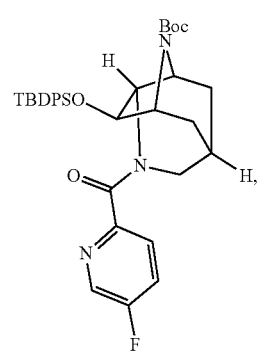

Formula XVI

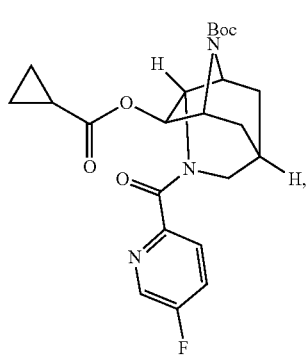

-continued

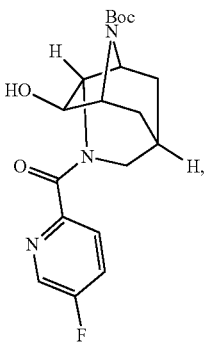
Formula XV

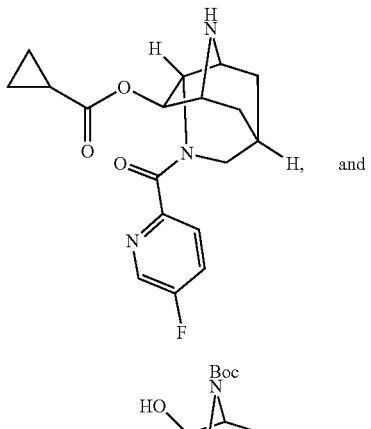
Formula XVII and

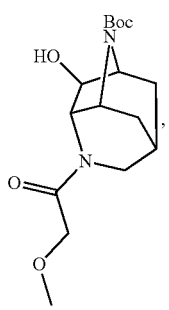
Formula XX or pharmaceutically acceptable salt, or stereoisomer thereof.

18. A method of producing a compound of

Formula XXIII(A)
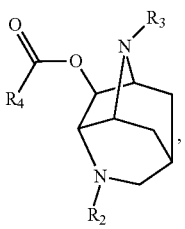

Formula XXIII(B)
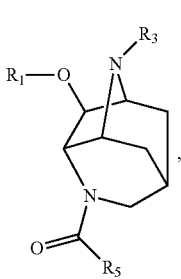

or

Formula XXIIII(D)
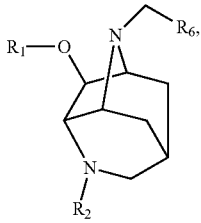

wherein R₁ is hydrogen, tert-butyldiphenylsiyl, or COC₃cyloakyl;
wherein R₂ is C═O optionally substituted pyridine, or COCH₂OCH₃;
wherein R₅ is fluoropyridine or CH₂COCH₃; and
wherein R₃ or R₆ is hydrogen, BOC, methylbenzodioxole, or phenyl substituted with CON(R')₂ wherein R' is H,
or a stereoisomer, or pharmaceutically acceptable salt thereof, by reacting scopolamine or a derivative thereof.

19. A compound of Formula XVIII:

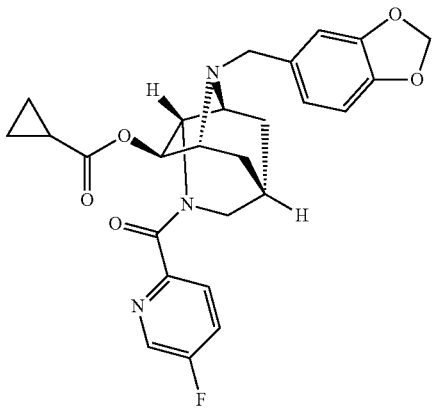 [SMILES: O=C(O[C@H]1[C@@H]2[C@@H]3C[C@@H](C[C@H]1N3Cc1ccc3c(c1)OCO3)CN2C(=O)c1ccc(F)cn1)C1CC1]

or a stereoisomer, pharmaceutically acceptable salt, or mixture thereof.

20. A pharmaceutical composition comprising a compound of claim 17, and a pharmaceutically acceptable carrier or diluent.

21. A pharmaceutical composition comprising a compound of claim 19, and a pharmaceutically acceptable carrier or diluent.

22. A method of producing a compound of claim 19, wherein the method comprises reacting a compound of Formula XIV
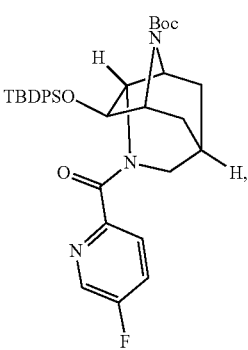

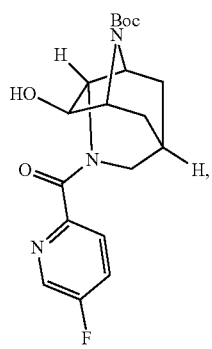

Formula XV

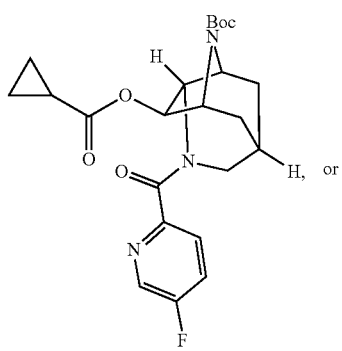

Formula XVI

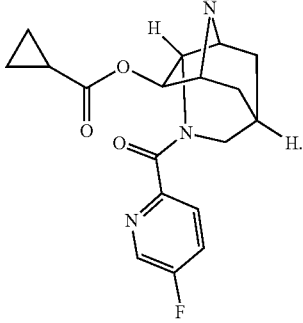

Formula XVII

23. A pharmaceutical composition comprising a compound of claim 3, and a pharmaceutically acceptable carrier or diluent.

24. A pharmaceutical composition comprising a compound of claim 9, and a pharmaceutically acceptable carrier or diluent.

25. A method for treating pain in a subject, comprising administering to the subject an effective amount of the compound of claim 3.

26. The method of claim 25, wherein the pain is neuropathic pain or chronic pain.

27. A method for treating pain in a subject, comprising administering to the subject an effective amount of the compound of claim 9.

28. The method of claim 27, wherein the pain is neuropathic pain or chronic pain.

* * * * *